US007345034B2

(12) United States Patent
Zhao et al.

(10) Patent No.: US 7,345,034 B2
(45) Date of Patent: Mar. 18, 2008

(54) AZACYCLOSTEROID HISTAMINE-3 RECEPTOR LIGANDS

(75) Inventors: Chen Zhao, Libertyville, IL (US);
Minghua Sun, Libertyville, IL (US);
Marlon D. Cowart, Round Lake Beach, IL (US); Youssef L. Bennani, Shaker Heights, OH (US)

(73) Assignee: Abbott Laboratories, Abbott Park, IL (US)

( * ) Notice: Subject to any disclaimer, the term of this patent is extended or adjusted under 35 U.S.C. 154(b) by 207 days.

(21) Appl. No.: 11/096,382

(22) Filed: Apr. 1, 2005

(65) Prior Publication Data

US 2005/0227953 A1 Oct. 13, 2005

Related U.S. Application Data

(60) Provisional application No. 60/560,151, filed on Apr. 7, 2004.

(51) Int. Cl.
*A61K 31/58* (2006.01)
*A61K 31/40* (2006.01)
*C07J 71/00* (2006.01)
*C07J 73/00* (2006.01)

(52) U.S. Cl. .................. 514/176; 514/410; 540/58; 548/426

(58) Field of Classification Search .............. 514/176, 514/410; 540/58, 426
See application file for complete search history.

(56) References Cited

U.S. PATENT DOCUMENTS

| 3,063,987 A | * | 11/1962 | Pappo | .................. 540/58 |
| 3,152,120 A | * | 10/1964 | Vlasios et al. | ............. 540/58 |
| 3,485,825 A |   | 12/1969 | Marx et al. | |
| 6,143,749 A |   | 11/2000 | Bhagwat et al. | ............. 514/258 |

FOREIGN PATENT DOCUMENTS

| GB | 1 170945 A | 11/1969 |
| GB | 1 230 681 A | 5/1971 |

OTHER PUBLICATIONS

Salimuzzaman Siddiqui, Proceedings of the Pakistan Acad. of Sciences, 18(2): 89-108, 1981, English Abstract Only.*
Bjenning et al., "Peripherally Administered Ciproxifan Elevates Hypothalamic Histamine Levels And Potently Reduces Food Intake in the Sprague Dawley Rat," Histamine Research In The New Mellennium, Proceedings Of The International Sendai Histamine Symposium Held In Sendai, Japan, Nov. 22-25, 2000, p. 449-450.
De Almeida et al., "Memory Facilitation by Histamine," Arch. Int. Pharmacodyn., 283:193-198 (1986).
Delaunois et al., "Modulation Of Acetylcholine, Capsaicin and Substance P Effects by Histamine $H_3$ Receptors in Isolated Perfused Rabbit Lungs," European Journal Of Pharmacology, 277:243-250 (1995).
Dimitriadou et al., "Functional Relationship Between Mast Cells and C-Sensitive Nerve Fibres Evidenced by Histamine $H_3$-Receptor Modulation in Rat Lung and Spleen," Clinical Science, 87:151-163 (1994).
Duméry et al., "Development of Amygdaloid Cholinergic Mediation of Passive Avoidance Learning in the Rat," Exp. Brain. Res., 67:61-69 (1987).
Fitzsimons et al., "Histamine Receptors Signalling in Epidermal Tumor Cell Lines With H-*ras* Gene Alterations," Inflamm. Res., 47, Supplement 1, S50-S51 (1998).
Fox et al., "Effects of Histamine $H_3$ Receptor Ligands GT-2331 And Ciproxifan in a Repeated Acquisition Response in the Spontaneously Hypertensive Rat Pup," Behavioural Brain Research 131:151-161 (2002).
Haas et al., Subcortical Modulation of Synaptic Plasticity in the Hippocampus, Behavioural Brain Research, 66:41-44 (1995).
Hatta et al., "Activation of Histamine $H_3$ Receptors Inhibits Carrier-Mediated Norepinephrine Release in a Human Model of Protracted Myocardial Ischemia[1,2]," The Journal Of Pharmacology And Experimental Therapeutics, 283(2):494-500 (1997).
Imamura et al., "Activation Of Histamine $H_3$-Receptors Inhibits Carrier-Mediated Norepinephrine Release During Protracted Myocardial Ischemia," Circulation Research, 78(3):475-481 (1996).
Imamura et al., "Histamine $H_3$-Receptor-Mediated Inhibition Of Calcitonin Gene-Related Peptide Release From Cardiac C Fibers," Circulation Research, 78(5):863-869 (1996).
Itoh et al., "Thioperamide, A Histamine $H_3$ Receptor Antagonist, Powerfully Suppresses Peptide YY-Induced Food Intake In Rats," Biol. Psychiatry 45:475-481 (1999).
Kamei et al., "Influence Of Certain $H_1$-Blockers On The Step-Through Active Avoidance Response In Rats,"Psychopharmacology, 102:312-318 (1990).
Kamei et al., "Participation Of Histamine In The Step-Through Active Avoidance Response And Its Inhibition By $H_1$-Blockers," Japan J. Pharmacol., 57:473-482 (1991).
Leurs et al., "The Histamine $H_3$-Receptor: A Target For Developing New Drugs," Progress In Drug Research, 39:127-165 (1992).
Leurs et al., "The Medicinal Chemistry And Therapeutic Potentials Of Ligands Of The Histamine $H_3$ Receptor," Progress In Drug Research, 45:107-165 (1995).
Leurs et al., "Therapeutic Potential Of Histamine $H_3$ Receptor Agonists And Antagonists," Trends In Pharm. Sci, 19:177-183 (1998).
Levi et al., "Histamine $H_3$-Receptors: A New Frontier In Myocardial Ischemia," The Journal Of Pharmacology And Experimental Therapeutics, 292(3):825-830 (2000).
Lin et al., "Involvement Of Histaminergic Neurons In Arousal Mechanisms Demonstrated With $H_3$-Receptor Ligands In The Cat," Brain Research, 523:325-330 (1990).

(Continued)

Primary Examiner—Barbara P. Badio
(74) Attorney, Agent, or Firm—Portia Chen

(57) ABSTRACT

Azacyclosteroid histamine-3 receptor ligands, pharmaceutical compositions comprising such compounds, and methods for using such compounds and compositions are described herein.

6 Claims, No Drawings

OTHER PUBLICATIONS

Matsubara et al., "UK-14,304, R(—) ∀-Methyl-Histamine And SMS 201-995 Block Plasma Protein Leakage Within Dura Mater By Prejunctional Mechanisms," European Journal Of Pharmacology, 224:145-150 (1992).

Mazurkiewicz-Kwilecki et al., "Changes In The Regional Brain Histamine And Histidine Levels In Postmortem Brains Of Alzheimer Patients," Can. J. Physiol. Pharmacol, 67: 75-78 (1989).

McLeod et al., "Histamine $H_3$ Antagonists," Progress In Resp. Research 31:133-134 (2001).

Monti et al., "Effects Of Selective Activation Or Blockade Of The Histamine $H_3$ Receptor On Sleep And Wakefulness," European Journal Of Pharmacology, 205:283-287 (1991).

Monti et al., "Sleep And Waking During Acute Histamine $H_3$ Agonist BP2.94 Or $H_3$ Antagonist Carboperamide (MR 16155) Administration In Rats," Neuropsychopharmacology, 15(1):31-35 (1996).

Murakami et al., "AQ-0145, A Newly Developed Histamine $H_3$ Antagonist, Decreased Seizure Susceptibility Of Electrically Induced Convulsions In Mice," Meth. Find. Exp. Clin. Pharmacol. 17(C):70-73 (1995).

Onodera et al., "Neuropharmacology Of The Histaminergic Neuron System In The Brain And Its Relationship With Behavioral Disorders," Progress In Neurobiology, 42:685-702 (1994).

Perez-Garcia et al., "Effects Of Histamine $H_3$ Receptor Ligands In Experimental Models Of Anxiety And Depression," Psychopharmacology 142:215-220 (1999).

Phillips et al., "Recent Advances In Histamine $H_3$Receptor Agents," Annual Reports In Medicinal Chemistry, 33:31-40 (1998).

Rouleau, "Bioavailability, Antinociceptive And Antiiflammatory Properties Of BP 2-94, A Histamine $H_3$ Receptor Agonist Prodrug," The Journal Of Pharmacology And Experimental Therapeutics, 281(3):1085-1094 (1997).

Sakai et al., "Effects Of Thioperamide, A Histamine $H_3$ Receptor Antagonist, On Locomotor Activity And Brain Histamine Content In Mast Cell-Deficient $W/W^V$ Mice," Life Sciences, 48:2397-2404 (1991).

Schwartz et al., "Histaminergic Transmission in the Mammalian Brain," Physiological Reviews 71(1):1-51 (1991).

Schwartz et al., "Histamine," Psychopharmacology: The Fourth Generation Of Progress, 397-405 (1995).

Shaywitz et al., "Dopaminergic But Not Noradrenergic Mediation Of Hyperactivity And Performance Deficits In The Developing Rat Pup," Psychopharmacology, 82:73-77 (1984).

Szelag, "Role Of Histamine $H_3$-Receptors In The Proliferation Of Neoplastic Cells In Vitro," Med. Sci. Monit., 4(5):747-755 (1998).

Tedford et al., "Cognition And Locomotor Activity In The Developing Rat: Comparisons Of Histamine $H_3$ Receptor Antagonists And ADHD Therapeutics," Society For Neuroscience Abstr., 22:22 (1996).

Tedford et al., "Pharmacological Characterization Of GT-2016, A Non-Thiourea-Containing Histamine $H_3$ Receptor Antagonist: In Vitro And In Vivo Studies," The Journal Of Pharmacology And Experimental Therapeutics, 275(2):598-604 (1995).

Tedford, "Clinical Applications Of HA $H_3$ Receptor Antagonists In Learning And Memory Disorders," The Histamine $H_3$ Receptor 269-286 (1998).

Van de Woude et al, "Amino steroids-Conanine and heteroconanine derivatives" Bulletin des Societes Chimiques Belges, 82: 49-62 (1973).

Wada et al., Is The Histaminergic Neuron System A Regulatory Center For Whole-Brain Activity?, Trends In Neurosciences, 14(9):415-418 (1991).

Yates et al., "Effects Of A Novel Histamine $H_3$ Receptor Antagonist, GT-2394, On Food Intake And Weight Gain In Sprague-Dawley Rats," Abstracts, Society For Neuroscience, 102.10:219 (Nov. 2000).

Yokoyama et al., "Effect Of Thioperamide, A Histamine $H_3$ Receptor Antagonist, On Electrically Induced Convulsions In Mice," Journal Of Pharmacology, 234:129-133 (1993).

Yokoyama et al., "Histamine And Seizures Implications For The Treatment Of Epilepsy," CNS Drugs, 5(5):321-330 (1996).

Salimuzzaman et al, "Some extension of von Braun BrCN reaction on organic bases" XP002340726, Proceedings of the Pakistan Acad. of Sciences, 18(2): 89-108 (1981), abstract only.

Cardell et al., "Characterization of the histamine receptors in the guinea-pig lung: evidence for relaxant histamine H3 receptors in the trachea" British Journal of Pharmacology 111(2): 445-54 (1994) XP002340727, abstract only.

Bakhsh, Ilahi, "Pharmacological action of conessine and isoconessing" J. Pharmacol. 58: 373-92 (1936) XP002340728, abstract only.

Chopra et al. "Pharmacological action of conessine, the alkaloid of Holarrhena anti-dysenterica", Indian Medical Gazette, 62:132-40 (1927), abstract only.

Burn et al. "The action of conessine and holarrhenine, the alkaloids of Holarrhena congolensis, and also of oxyconessine", J. Pharmacol. 6: 305-21 (1915), abstract only.

Auffret et al., "Distribution and fixing of conessine in organs of the monkey", Medicine Tropicale (Marseille) 10:530-6 (1950), abstract only.

Stark H, "Recent advances in histamine H3/H4 receptor ligands" Expert Opinion on Therapeutic Patents, 13(6):853-865 (Jun. 1, 2003).

Panula et al., "Neuronal Histamine Deficit in Alzheimer's Disease", Neuroscience, 82(4): 993-997 (1998).

Panula et al., "Brain histamine in pathophysiological conditions and brain diseases", The Histamine H3 Receptor, pp. 243-253 (1998 Elsevier Science).

* cited by examiner

AZACYCLOSTEROID HISTAMINE-3 RECEPTOR LIGANDS

This application claims priority from U.S. Provisional Patent Application Ser. No. 60/560,151, filed Apr. 7, 2004, incorporated herein by reference.

BACKGROUND OF THE INVENTION

1. Technical Field

The invention relates to azacyclosteroid compounds, compositions comprising such compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (Nature, 302:832-837 (1983)), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists ((Nature, 327:117-123 (1987); Leurs and Timmerman, ed. "The History of $H_3$ Receptor: a Target for New Drugs," Elsevier (1998)).

The activity at the $H_3$ receptors can be modified or regulated by the administration of $H_3$ receptor ligands. The ligands can exhibit antagonist, agonist, partial agonist, or inverse agonist properties. For example, $H_3$ receptors have been linked to conditions and disorders related to memory and cognition processes, neurological processes, cardiovascular function, and regulation of blood sugar, among other systemic activities. Although various classes of compounds demonstrating $H_3$ receptor-modulating activity exist, it would be beneficial to provide additional compounds demonstrating activity at the $H_3$ receptors that can be incorporated into pharmaceutical compositions useful for therapeutic methods.

SUMMARY OF THE INVENTION

The invention is directed to azacyclosteroid compounds, compositions comprising the compounds, and methods of using such compounds and compositions. The compounds of the invention have the formula:

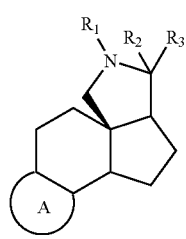

(IA)

or a pharmaceutically acceptable salt, ester, amide, or prodrug thereof, wherein $R_1$ is selected from the group consisting of hydrogen, acetyl, alkyl, fluoroalkyl, and cycloalkyl;

$R_2$ and $R_3$ are each independently selected from the group consisting of hydrogen and alkyl, or $R_2$ and $R_3$ taken together form a 3- to 6-membered ring;

Ring A of the formula:

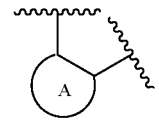

is selected from the following:

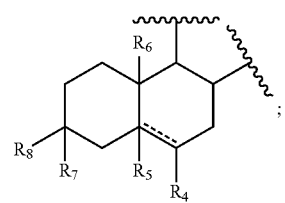

(a)

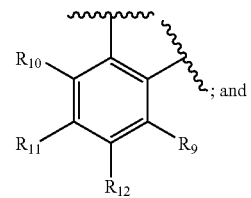

(b)

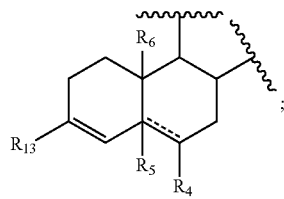

(c)

wherein:

the dotted line represents an optional bond;

$R_4$ and $R_5$ are each independently selected from the group consisting of hydrogen and fluorine, provided that $R_5$ is present only when the bond represented by the dotted line is absent;

$R_6$ is selected from the group consisting of hydrogen, alkyl, and fluorine;

one of $R_7$ and $R_8$ is hydrogen; and the other of $R_7$ and $R_8$ is selected from the group consisting of:

a) $NR_{18}R_{19}$;

b) $OR_{20}$, $SR_{20}$, $O(C=O)OR_{20}$, $O(C=O)N(R_{20})(R_{21})$, $O(C=O)C(R_{23})(R_{24})(R_{24b})$, or $O(C=O)CH(NR_{28}R_{29})R_{25}$; and c) $NR_{22}(C=O)R_{25}$, $NR_{22}(C=O)NR_{26}R_{27}$, $NR_{22}(C=O)CH(NR_{28}R_{29})R_{30}$, $N(R_{22})(C=O)OR_{20}$, or $NR_{22}(C=O)C(OR_{23})R_{30}R_{30b}$; and d) $NR_{22}SO_2R_{31}$ or $NR_{22}SO_2N(R_{22})(R_{23})$;

or $R_7$ and $R_8$ taken together with the carbon atom to which each is attached forms a group of the formula $-C=C(R_a)(R_b)$, wherein $R_a$ and $R_b$ are each independently selected from the group consisting of hydrogen, alkyl, and cycloalkyl;

$R_9$ and $R_{10}$ are each independently selected from the group consisting of hydrogen, halogen, alkyl, and cyano;

$R_{11}$ and $R_{12}$ are each independently selected from the group consisting of hydrogen, heteroaryl, heterocycle, aryl arylalkyl, aryloxy, arylcarbonyl, arylcarbonyloxy, arylalkoxy, alkylsulfonyl, arylsulfonyl, and trifluoromethylsulfonyl; or one of $R_{10}$ and $R_{11}$ or $R_{11}$ and $R_{12}$ taken together with the atoms to which each is attached form a 5- to 6-membered aromatic or heteroaromatic ring;

$R_{13}$ is selected from the group consisting of alkyl, cycloalkyl, aryl, and heteroaryl;

$R_{18}$ is hydrogen or $C_1$-$C_6$ alkyl and $R_{19}$ is selected from the group consisting of aryl and heteroaryl, or $R_{18}$ and $R_{19}$ at each occurrence is taken together form a 3- to 8-membered heterocycle;

$R_{20}$ and $R_{21}$ at each occurrence are each independently selected from the group consisting of hydrogen, alkyl, cycloalkyl, alkoxyalkyl, cyanoalkyl, hydroxyalkyl, haloalkyl, aryl, aryloxy, arylalkyl, arylsulfonyl, heteroaryl, heteroarylalkyl, heteroarylcarbonyl, heterocycle, and heterocyclealkyl, provided that when $R_7$ or $R_8$ is $OR_{20}$, $R_{20}$ is not hydrogen or methyl;

$R_{22}$ at each occurrence is selected from the group consisting of hydrogen and alkyl;

$R_{23}$ at each occurrence is selected from the group consisting of hydrogen, alkyl, and alkylcarbonyl;

$R_{24}$ and $R_{24b}$ are each independently selected from the group consisting of hydrogen, alkyl, aryl, arylalkyl, and cycloalkyl, provided that only one of $R_{24}$ and $R_{24b}$ can be hydrogen;

$R_{25}$ at each occurrence is independently selected from the group consisting of $C_2$-$C_6$ alkyl, alkoxyalkyl, hydroxyalkyl, a phenyl ring substituted with 1, 2 or 3 substituents selected from the group consisting of halogen, cyano, alkyl, and alkoxy, naphthyl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{26}$ and $R_{27}$ are each independently selected from the group consisting of alkyl, alkylcarbonyl, alkoxycarbonyl, cycloalkyl, aryl, heteroaryl, and heterocycle, provided that $R_{26}$ and $R_{27}$ are not both alkyl, or $R_{26}$ and $R_{27}$ taken together with the nitrogen atom to which each is attached forms an aromatic or non-aromatic 5- to 6-membered ring, wherein 0, 1, or 2 carbon atoms in the ring is substituted with a heteroatom selected from O, S, or $NR_{23}$;

$R_{28}$ and $R_{29}$ at each occurrence are each independently selected from the group consisting of hydrogen, alkyl, alkylcarbonyl, alkoxycarbonyl, cycloalkyl, aryl, heteroaryl, and heterocycle, or $R_{28}$ and $R_{29}$ taken together with the nitrogen atom to which each is attached forms an aromatic or nonaromatic 5 to 6-membered ring, wherein 0, 1, or 2 carbon atoms in the ring is substituted with a heteroatom selected from O, S, or $NR_{23}$;

$R_{30}$ at each occurrence is independently selected from the group consisting of hydrogen, alkyl, alkoxyalkyl, hydroxyalkyl, aryl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{30b}$ is selected from the group consisting of hydrogen and alkyl, or when $R_{30}$ is alkyl and $R_{30b}$ is alkyl, the alkyl groups can be bonded together to form a $C_3$-$C_4$ cycloalkyl group; and $R_{31}$ is selected from the group consisting of alkyl, cycloalkyl, aryl, heterocycle, and heteroaryl.

The invention also relates to a method of treating a condition modulated by the histamine-3 receptors in a mammal comprising administering an effective amount of a compound of the formula:

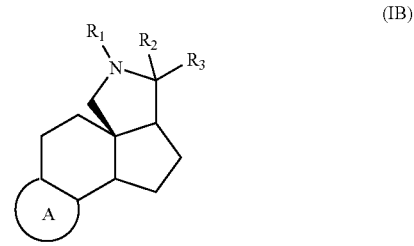

(IB)

or a pharmaceutically acceptable salt, ester, amide, or prodrug thereof, wherein $R_1$ is selected from the group consisting of hydrogen, acetyl, alkyl, fluoroalkyl, and cycloalkyl;

$R_2$ and $R_3$ are each independently selected from the group consisting of hydrogen and alkyl, or $R_2$ and $R_3$ taken together form a 3- to 6-membered ring;

Ring A of the formula:

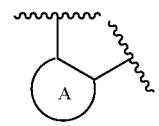

is selected from the following:

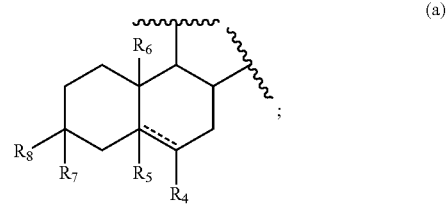

(a)

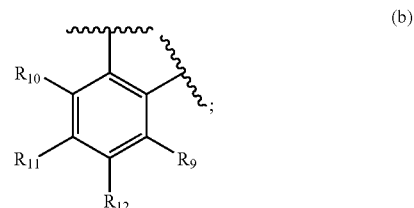

(b)

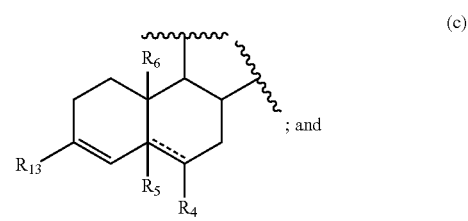

(c)

; and

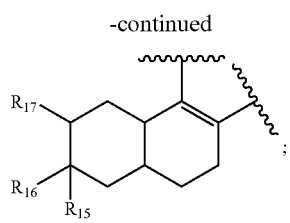
(d)

wherein:
the dotted line represents an optional bond;

$R_4$ and $R_5$ are each independently selected from the group consisting of hydrogen and fluorine, provided that $R_5$ is present only when the bond represented by the dotted line is absent;

$R_6$ is selected from the group consisting of hydrogen, alkyl, and fluorine;

one of $R_7$ and $R_8$ is hydrogen; and the other of $R_7$ and $R_8$ is selected from the group consisting of:
a) $NR_{18}R_{19}$;
b) $OR_{20}$, $SR_{20}$, $O(C=O)OR_{20}$, $O(C=O)N(R_{20})(R_{21})$, $O(C=O)C(R_{23})(R_{24})(R_{24b})$, or $O(C=O)CH(NR_{28}R_{29})R_{25}$; and
c) $NR_{22}(C=O)R_{25}$, $NR_{22}(C=O)NR_{26}R_{27}$, $NR_{22}(C=O)CH(NR_{28}R_{29})R_{30}$, $N(R_{22})(C=O)OR_{20}$, or $NR_{22}(C=O)C(OR_{23})R_{30}R_{30b}$; and
d) $NR_{22}SO_2R_{31}$ or $NR_{22}SO_2N(R_{22})(R_{23})$;

or $R_7$ and $R_8$ taken together with the carbon atom to which each is attached forms a group of the formula $-C=C(R_a)(R_b)$, wherein $R_a$ and $R_b$ are each independently selected from the group consisting of hydrogen, alkyl, and cycloalkyl;

$R_9$ and $R_{10}$ are each independently selected from the group consisting of hydrogen, halogen, alkyl, and cyano;

$R_{11}$ and $R_{12}$ are each independently selected from the group consisting of hydrogen, heteroaryl, heterocycle, aryl, arylalkyl, aryloxy, arylcarbonyl, arylcarbonyloxy, arylalkoxy, alkylsulfonyl, arylsulfonyl, and trifluoromethylsulfonyl; or one of $R_{10}$ and $R_{11}$ or $R_{11}$ and $R_{12}$ taken together with the atoms to which each is attached form a 5- to 6-membered aromatic or heteroaromatic ring;

$R_{13}$ is selected from the group consisting of alkyl, cycloalkyl, aryl, and heteroaryl;

$R_{15}$ and $R_{16}$ taken together with the atom to which each is attached forms a 5- to 6-membered ring optionally substituted with an alkylamino group;

$R_{17}$ is selected from the group consisting of hydrogen, alkyl, and fluoro;

$R_{18}$ is hydrogen or $C_1$-$C_6$ alkyl and $R_{19}$ is selected from the group consisting of aryl and heteroaryl, or $R_{18}$ and $R_{19}$ at each occurrence is taken together form a 3- to 8-membered heterocycle;

$R_{20}$ and $R_{21}$ at each occurrence are each independently selected from the group consisting of hydrogen, alkyl, cycloalkyl, alkoxyalkyl, cyanoalkyl, hydroxyalkyl, haloalkyl, aryl, aryloxy, arylalkyl, arylsulfonyl, heteroaryl, heteroarylalkyl, heteroarylcarbonyl, heterocycle, and heterocyclealkyl;

$R_{22}$ at each occurrence is selected from the group consisting of hydrogen and alkyl;

$R_{23}$ at each occurrence is selected from the group consisting of hydrogen, alkyl, and alkylcarbonyl;

$R_{24}$ and $R_{24b}$ are each independently selected from the group consisting of hydrogen, alkyl, aryl, arylalkyl, and cycloalkyl;

$R_{25}$ at each occurrence is independently selected from the group consisting of $C_1$-$C_6$ alkyl, alkoxyalkyl, hydroxyalkyl, aryl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{26}$ and $R_{27}$ are each independently selected from the group consisting of alkyl, alkylcarbonyl, alkoxycarbonyl, cycloalkyl, aryl, heteroaryl, and heterocycle, or $R_{26}$ and $R_{27}$ taken together with the nitrogen atom to which each is attached forms an aromatic or non-aromatic 5- to 6-membered ring, wherein 0, 1, or 2 carbon atoms in the ring is substituted with a heteroatom selected from O, S, or $NR_{23}$;

$R_{28}$ and $R_{29}$ at each occurrence are each independently selected from the group consisting of hydrogen, alkyl, alkylcarbonyl, alkoxycarbonyl, cycloalkyl, aryl, heteroaryl, and heterocycle, or $R_{28}$ and $R_{29}$ taken together with the nitrogen atom to which each is attached forms an aromatic or nonaromatic 5 to 6-membered ring, wherein 0, 1, or 2 carbon atoms in the ring is substituted with a heteroatom selected from O, S, or $NR_{23}$;

$R_{30}$ at each occurrence is independently selected from the group consisting of hydrogen, alkyl, alkoxyalkyl, hydroxyalkyl, aryl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{30b}$ is selected from the group consisting of hydrogen and alkyl, or when $R_{30}$ is alkyl and $R_{30b}$ is alkyl, the alkyl groups can be bonded together to form a $C_3$-$C_4$ cycloalkyl group; and $R_{31}$ is selected from the group consisting of alkyl, cycloalkyl, aryl, heterocycle, and heteroaryl.

Another aspect of the invention relates to pharmaceutical compositions comprising compounds of the invention. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating and/or preventing conditions and disorders related to $H_3$ receptor modulation in mammals. More particularly, the method is useful for conditions and disorders related to memory and cognition processes, neurological processes, cardiovascular function, and body weight.

The compounds, compositions comprising the compounds, and methods for treating or preventing conditions and disorders by administering the compounds are further described herein.

DETAILED DESCRIPTION OF THE INVENTION

Definition of Terms

Certain terms as used in the specification are intended to refer to the following definitions, as detailed below.

The term "acyl" as used herein, means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "acyloxy" as used herein, means an acyl group, as defined herein, appended to the parent molecular moiety through an oxygen atom. Representative examples of acyloxy include, but are not limited to, acetyloxy, propionyloxy, and isobutyryloxy.

The term "alkenyl" as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein, means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkoxysulfonyl" as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl, and propoxysulfonyl.

The term "alkyl" as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3methylhexyl, 2,2-dimethylpentyl, 2,3-dimethylpentyl, n-heptyl, n-octyl, n-nonyl, and n-decyl.

The term "alkylcarbonyl" as used herein, means an alkyl group, as defined herein, appended to the parent molecular moiety through a carbonyl group, as defined herein. Representative examples of alkylcarbonyl include, but are not limited to, methylcarbonyl and ethylcarbonyl.

The term "alkylsulfonyl" as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amido" as used herein, means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein, means a —$NH_2$ group.

The term "aryl" as used herein, means a monocyclic or bicyclic aromatic ring system. Representative examples of aryl include, but are not limited to, phenyl and naphthyl.

The aryl groups of this invention are substituted with 0, 1, 2, 3, 4, or 5 substituents independently selected from acyl, acyloxy, alkanoyl, alkenyl, alkoxy, alkoxyalkoxy, alkoxyalkyl, alkoxycarbonyl, alkoxyimino, alkoxysulfonyl, alkyl, alkylsulfonyl, alkynyl, amido, carbonyl, carboxy, cyano, formyl, haloalkoxy, haloalkyl, halo, hydroxy, hydroxyalkyl, hydroxyimino, mercapto, nitro, thioalkoxy, —$NR_AR_B$, and ($NR_AR_B$)sulfonyl.

The term "arylalkyl" as used herein, means at least one aryl group, as defined herein, appended to the parent molecular moiety through an alkyl group, as defined herein. Representative examples of arylalkyl include phenylmethyl, naphthylethyl, and the like.

The term "aryloxy" as used herein, means an aryl group, as defined herein, appended to the parent molecular moiety through an oxygen atom, as defined herein. Representative examples of aryloxy include, but are not limited to, phenoxy and naphthoxy.

The term "arylalkoxy" as used herein, means an aryl group, as defined herein, appended to the parent molecular moiety through an alkoxy group, as defined herein. Representative examples of arylalkoxy include, but are not limited to, phenylmethoxy, 2-phenylethoxy, 2-naphthylethoxy, and naphthylmethoxy.

The term "arylsulfonyl" as used herein, means an aryl group, as defined herein, appended to the parent molecular moiety through a sulfonyl group, as defined herein. Representative examples of arylsulfonyl include, but are not limited to, phenylsulfonyl and naphthylsulfonyl.

The term "carbonyl" as used herein, means a —C(O)— group.

The term "carboxy" as used herein, means a —$CO_2H$ group, which may be protected as an ester group —$CO_2$-alkyl.

The term "cyano" as used herein, means a —CN group.

The term "cyanoalkyl" as used herein, means at least one cyano group, as defined herein, appended to the parent molecular moiety through an alkyl group, as defined herein. Representative examples of cyanoalkyl include, but are not limited to, cyanomethyl.

The term "cycloalkyl" as used herein, means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The cycloalkyl groups of the invention are substituted with 0, 1, 2, 3, or 4 substituents selected from acyl, acyloxy, alkenyl, alkoxy, alkoxyalkoxy, alkoxyalkyl, alkoxycarbonyl, alkoxyimino, alkyl, alkynyl, amido, carboxy, cyano, ethylenedioxy, formyl, haloalkoxy, haloalkyl, halo, hydroxy, hydroxyalkyl, methylenedioxy, thioalkoxy, and —$NR_AR_B$.

The term "cycloalkylalkyl" as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "ethylenedioxy" as used herein, means a —O(CH$_2$)$_2$O— group wherein the oxygen atoms of the ethylenedioxy group are attached to the parent molecular moiety through one carbon atom forming a five-membered ring or the oxygen atoms of the ethylenedioxy group are attached to the parent molecular moiety through two adjacent carbon atoms forming a six-membered ring.

The term "fluoro" as used herein means —F.

The term "fluoroalkyl" as used herein, means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, pentafluoroethyl, and 2,2,2-trifluoroethyl.

The term "formyl" as used herein, means a —C(O)H group.

The term "halo" or "halogen" as used herein, means —Cl, —Br, —I or —F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, refers to an aromatic five or six-membered ring wherein 1, 2, 3, or 4 heteroatoms are independently selected from nitrogen, oxygen, or sulfur. Heteroaryl also refers to fused aromatic nine- and ten-membered bicyclic rings containing 1, 2, 3, or 4 heteroatoms independently selected from nitrogen, oxygen, or sulfur, or a tautomer thereof. Examples of such rings include, but are not limited to, a ring wherein one carbon is replaced with an O or S atom; one, two, or three N atoms arranged in a suitable manner to provide an aromatic ring, or a ring wherein two carbon atoms in the ring are replaced with one O or S atom and one N atom. The heteroaryl groups are connected to the parent molecular moiety through a carbon or nitrogen atom. Representative examples of heteroaryl include, but are not limited to, furyl, imidazolyl, isoxazolyl, isothiazolyl, oxadiazolyl, oxazolyl, pyrazinyl, pyrazolyl, pyridazinyl, pyridazinonyl, pyridinyl, pyrimidinyl, pyrrolyl, tetrazolyl, thiadiazolyl, thiazolyl, thienyl, triazinyl, triazolyl, indolyl, benzothiazolyl, benzofuranyl, isoquinolinyl, and quinolinyl.

The heteroaryl groups of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, carboxy, cyano, formyl, haloalkoxy, haloalkyl, halo, hydroxy, hydroxyalkyl, mercapto, nitro, thioalkoxy, —NR$_A$R$_B$, and (NR$_A$R$_B$)sulfonyl.

The term "heteroarylalkyl" as used herein, means at least one heteroaryl group, as defined herein, appended to the parent molecular moiety through an alkyl group, as defined herein. Representative examples of heteroarylalkyl include thienylmethyl, triazinylethyl, triazolylethyl, indolylmethyl, and the like.

The term "heterocycle," as used herein, refers to a three-, four-, five-, six-, seven-, or eight-membered ring containing one, two, or three heteroatoms independently selected from the group consisting of nitrogen, oxygen, and sulfur. Rings containing at least four members can be saturated or unsaturated. For example, the four- and five- membered ring has zero or one double bond. The six-membered ring has zero, one, or two double bonds. The seven- and eight-membered rings have zero, one, two, or three double bonds. The heterocycle groups of the invention can be attached to the parent molecular moiety through a carbon atom or a nitrogen atom. Representative examples of nitrogen-containing heterocycles include, but are not limited to, azepanyl, azetidinyl, aziridinyl, azocanyl, morpholinyl, piperazinyl, piperidinyl, pyrrolidinyl, pyrrolinyl, and thiomorpholinyl. Representative examples of non-nitrogen containing heterocycles include, but are not limited to, tetrahydrofuranyl and tetrahydropyranyl.

The heterocycles of the invention are substituted with 0, 1, 2, 3, or 4 substituents independently selected from acyl, acyloxy, alkenyl, alkoxy, alkoxyalkoxy, alkoxyalkyl, alkoxycarbonyl, alkoxyimino, alkoxysulfonyl, alkyl, alkylsulfonyl, alkynyl, amido, arylalkyl, arylalkoxycarbonyl, carboxy, cyano, formyl, haloalkoxy, haloalkyl, halo, hydroxy, hydroxyalkyl, mercapto, nitro, oxo, thioalkoxy, —NR$_A$R$_B$, and (NR$_A$R$_B$)sulfonyl.

The term "heterocyclealkyl" as used herein, means at least one heteroaryl group, as defined herein, appended to the parent molecular moiety through an alkyl group, as defined herein. Representative examples of heterocyclealkyl include morpholinylmethyl, piperazinylmethyl, piperidinylethyl, pyrrolidinylethyl, and pyrrolinylethyl.

The term "hydroxy" as used herein means an —OH group.

The term "hydroxyalkyl" as used herein, means at least one hydroxy group, as defined herein, appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonidebenzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, CH$_2$I$_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "mercapto" as used herein, means a —SH group.

The term "methylenedioxy" as used herein, means a —OCH$_2$O— group wherein the oxygen atoms of the methylenedioxy are attached to the parentmolecular moiety through two adjacent carbon atoms.

The term "—NR$_A$R$_B$" as used herein, means two groups, R$_A$ and R$_B$, which are appended to the parent molecular moiety through a nitrogen atom. R$_A$ and R$_B$ are independently selected from hydrogen, alkyl, acyl and formyl. Representative examples of —NR$_A$R$_B$ include, but are not limited to, amino, methylamino, acetylamino, and acetylmethylamino.

The term "(NR$_A$R$_B$)sulfonyl" as used herein, means a —NR$_A$R$_B$ group, as defined herein, appended to the parent molecular moiety through a sulfonyl group, as defined herein. Representative examples of (NR$_A$R$_B$)sulfonyl include, but are not limited to, aminosulfonyl, (methylamino)sulfonyl, (dimethylamino)sulfonyl and (ethylmethylamino)sulfonyl.

The term "nitro" as used herein means a —N(O)$_2$— group.

The term "oxo" as used herein means a —O— group.

The term "sulfonyl" as used herein means a —S(O)$_2$— group.

The term "thioalkoxy" as used herein means an alkyl group, as defined herein, appended to the parent molecular moiety through a sulfur atom. Representative examples of thioalkoxy include, but are not limited to, methylthio, ethylthio, and propylthio.

As used herein, the term "antagonist" encompasses and describes compounds that prevent receptor activation by an H$_3$receptor agonist alone, such as histamine, and also encompasses compounds known as "inverse agonists". Inverse agonists are compounds that not only prevent receptor activation by an H$_3$ receptor agonist, such as histamine, but inhibit intrinsic receptor activity.

Compounds of the Invention

Compounds of the invention can have the general formula (I) as previously described.

More particularly, the invention can comprise compounds of formula (II), having the formula:

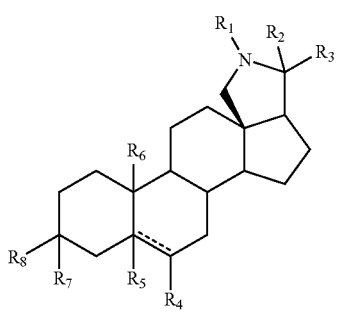

(II)

wherein:
the dotted line represents an optional bond;
R$_1$ is selected from the group consisting of hydrogen, acetyl, alkyl, fluoroalkyl, and cycloalkyl;
R$_2$ and R$_3$ are each independently selected from the group consisting of hydrogen and alkyl, or R$_2$ and R$_3$ taken together form a 3- to 6-membered ring;
R$_4$ and R$_5$ are each independently selected from the group consisting of hydrogen and fluorine, provided that R$_5$ is present only when the bond represented by the dotted line is absent;
R$_6$ is selected from the group consisting of hydrogen, alkyl, and fluorine;

one of R$_7$ and R$_8$ is hydrogen; and the other of R$_7$ and R$_8$ is selected from the group consisting of:
a) NR$_{18}$R$_{19}$;
b) OR$_{20}$, SR$_{20}$, O(C=O)OR$_{20}$, O(C=O)N(R$_{20}$)(R$_{21}$), O(C=O)C(R$_{23}$)(R$_{24}$)(R$_{24b}$), or O(C=O)CH(NR$_{28}$R$_{29}$)R$_{25}$; and
c) NR$_{22}$(C=O)R$_{25}$, NR$_{22}$(C=O)NR$_{26}$R$_{27}$, NR$_{22}$(C=O)CH(NR$_{28}$R$_{29}$)R$_{30}$, N(R$_{22}$)(C=O)OR$_{20}$, or NR$_{22}$(C=O)C(OR$_{23}$)R$_3$R$_{30b}$; and
d) NR$_{22}$SO$_2$R$_{31}$ or NR$_{22}$SO$_2$N(R$_{22}$)(R$_{23}$);

or R$_7$ and R$_8$ taken together with the carbon atom to which each is attached forms a group of the formula —C=C(R$_a$)(R$_b$), wherein R$_a$ and R$_b$ are each independently selected from the group consisting of hydrogen, alkyl, and cycloalkyl;

R$_{18}$ is hydrogen or C$_1$-C$_6$ alkyl and R$_{19}$ is selected from the group consisting of aryl and heteroaryl, or R$_{18}$ and R$_{19}$ at each occurrence is taken together form a 3- to 8-membered heterocycle;

R$_{20}$ and R$_{21}$ at each occurrence are each independently selected from the group consisting of hydrogen, alkyl, cycloalkyl, alkoxyalkyl, cyanoalkyl, hydroxyalkyl, haloalkyl, aryl, aryloxy, arylalkyl, arylsulfonyl, heteroaryl, heteroarylalkyl, heteroarylcarbonyl, heterocycle, and heterocyclealkyl, provided that when R$_7$ or R$_8$ is OR$_{20}$, R$_{20}$is not hydrogen or methyl;

R$_{22}$ at each occurrence is selected from the group consisting of hydrogen and alkyl;

R$_{23}$ at each occurrence is selected from the group consisting of hydrogen, alkyl, and alkylcarbonyl;

R$_{24}$ and R$_{24b}$ are each independently selected from the group consisting of hydrogen, alkyl, aryl, arylalkyl, and cycloalkyl, provided that only one of R$_{24}$ and R$_{24b}$ can be hydrogen;

R$_{25}$ at each occurrence is independently selected from the group consisting of C$_2$-C$_6$ alkyl, alkoxyalkyl, hydroxyalkyl, a phenyl ring substituted with 1, 2 or 3-substituents selected from the group consisting of halogen, cyano, alkyl, and alkoxy, naphthyl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

R$_{26}$ and R$_{27}$ are each independently selected from the group consisting of alkyl, alkylcarbonyl, alkoxycarbonyl, cycloalkyl, aryl, heteroaryl, and heterocycle, provided that R$_{26}$ and R$_{27}$ are not both alkyl, or R$_{26}$ and R$_{27}$ taken together with the nitrogen atom to which each is attached forms an aromatic or non-aromatic 5- to 6-membered ring, wherein 0, 1, or 2 carbon atoms in the ring is substituted with a heteroatom selected from O, S, or NR$_{23}$;

R$_{28}$ and R$_{29}$ at each occurrence are each independently selected from the group consisting of hydrogen, alkyl, alkylcarbonyl, alkoxycarbonyl, cycloalkyl, aryl, heteroaryl, and heterocycle, or R$_{28}$ and R$_{29}$ taken together with the nitrogen atom to which each is attached forms an aromatic or non-aromatic 5- to 6-membered ring, wherein 0, 1, or 2 carbon atoms in the ring is substituted with a heteroatom selected from O, S, or NR$_{23}$;

R$_{30}$ at each occurrence is independently selected from the group consisting of hydrogen, alkyl, alkoxyalkyl, hydroxyalkyl, aryl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{30b}$ is selected from the group consisting of hydrogen and alkyl, or when $R_{30}$ is alkyl and $R_{30b}$ is alkyl, the alkyl groups can be bonded together to form a $C_3$-$C_4$ cycloalkyl group; and $R_{31}$ is selected from the group consisting of alkyl, cycloalkyl, aryl, heterocycle, and heteroaryl, also are specifically contemplated. Such compounds are preferred for the method of the invention.

Preferred compounds of formula (1A), (1 B) and (II) are those wherein one of $R_7$ and $R_8$ is hydrogen; and the other of $R_7$ and $R_8$ is selected from the group consisting of $NR_{22}(C=O)R_{25}$, $NR_{22}(C=O)CH(NR_{28}R_{29})R_{30}$, and $NR_{22}(C=O)C(OR_{23})R_{30}R_{30b}$.

The preferred group for $R_7$ or $R_8$ in compounds of formula (IA), (1B), or (II) is $NR_{22}(C=O)CH(NR_{28}R_{29})R_{30}$, wherein $R_{22}$ is alkyl, $R_{28}$ and $R_{29}$ are each hydrogen, and $R_{30}$ is selected from the group consisting of alkyl and aryl, particularly phenyl. Particularly, the compounds wherein $R_{22}$ is methyl are preferred.

Specific examples of compounds contemplated as part of the invention, include, but are not limited to, those named and shown in the Examples, not including the Reference Examples.

Compounds of the invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, Pure Appl. Chem., 1976, 45: 13-30. The invention contemplates various stereoisomers and mixtures thereof and are specifically included within the scope of this invention. Stereoisomers include enantiomers and diastereomers, and mixtures of enantiomers or diastereomers. Individual stereoisomers of compounds of the invention may be prepared synthetically from commercially available starting materials containing asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Methods for Preparing Compounds of the Invention

The compounds of the invention can be better understood in connection with the following synthetic schemes and methods. Such description illustrates a means by which the compounds can be prepared.

As used in the descriptions of the schemes and the examples, certain abbreviations are intended to have the following meanings: Ac for acetyl; BINAP for 2,2'-bis (diphenylphosphino)-1,1'-binaphthyl; Boc (or BOC) for butyloxycarbonyl; Bu for butyl; DCM for dichloromethane; DMF for N,N-dimethylformamide; DMSO for dimethylsulfoxide; EDC for 1-[3-(dimethylamino)propyl]-3-ethyl carbodiimide; EDTA for ethylenediaminetetraacetic acid; Et for ethyl; EtOH for ethanol; EtOAc for ethyl acetate; HOBt for hydroxybenzotriazole; HPLC for high pressure liquid chromatography; Me for methyl; MeOH for methanol; Ms for methanesulfonyl; OAc for acetate; Pb/Cd for lead on cadmium; Pd/C for palladium on carbon; Ph for phenyl; PNP for paranitrophenol; tBu for tert-butyl; TEA for triethylamine; TFA for trifluoroacetic acid; THF for tetrahydrofuran; Tf for trifluoromethanesulfonyl; and Troc for 2,2,2-trichloroethylcarbonyl.

The compounds of this invention can be prepared by a variety of synthetic procedures. Representative procedures are shown in, but are not limited to, Schemes 1-5.

Scheme 1

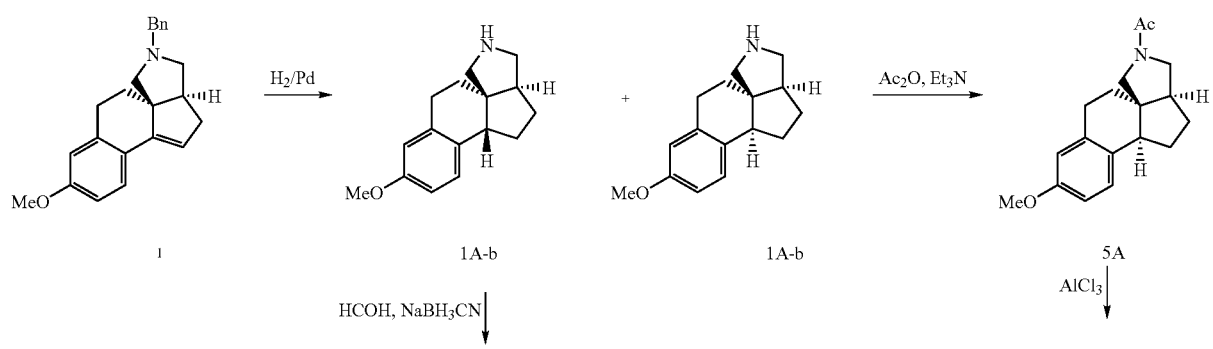

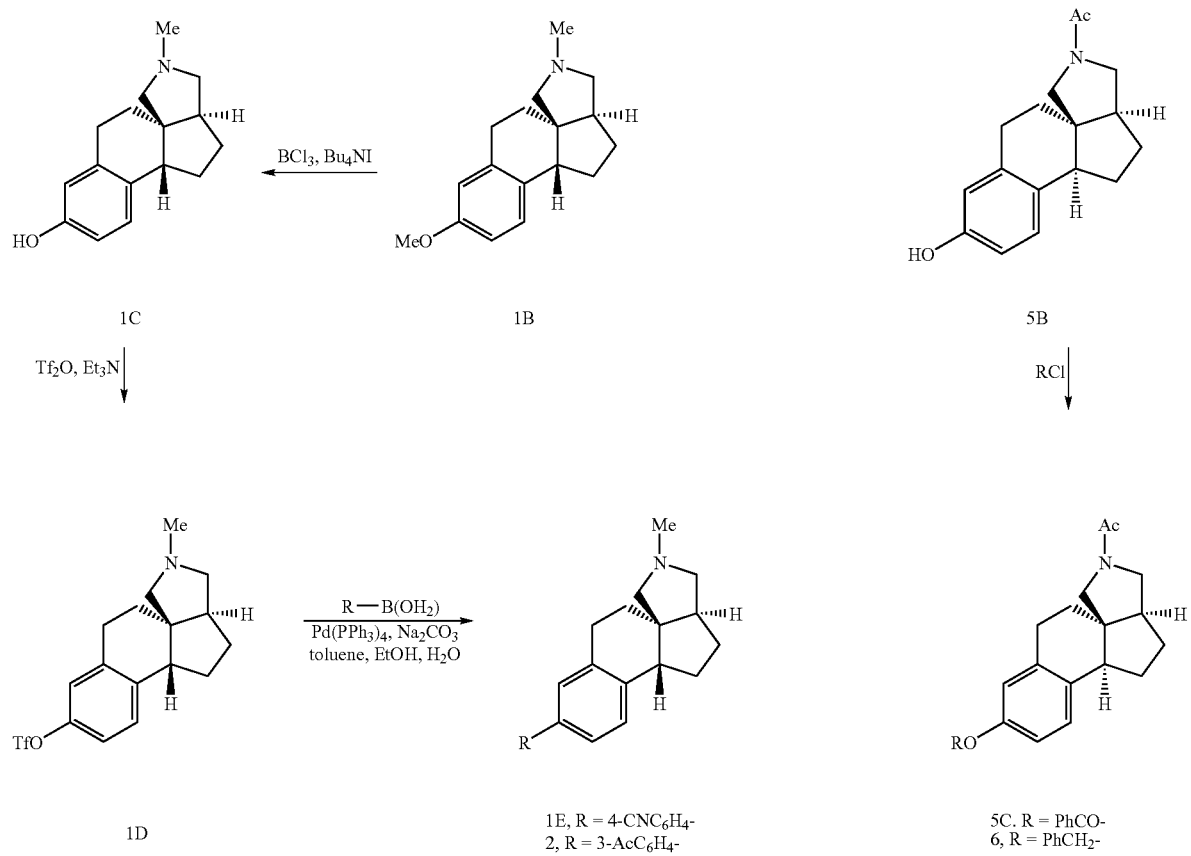

Compounds of formula 1 E, 2, 5C and 6 can be prepared as described in Scheme 1. A compound of formula 1 is prepared according to the procedure described in Kopach, M. E.; Fray, A. H. & Meyers A. I., J. Am. Chem. Soc. 1996, 118, 9876. Compound 1 can be hydrogenated under hydrogenation conditions well-known to those with skill in the art, for example hydrogen gas in the presence of a palladium catalyst. The two products 1A-a and 1A-b can be separated by column chromatography. A compound of formula 1A-a is treated with paraformaldehyde and sodium cyanoborohydride to provide a compound of formula 1B. Compound 1B is demethylated with tetrabutylammonium iodide and trichloroborane to afford a compound of formula 1C. Compound 1C is treated with trifluoromethane sulfonic anhydride in an amine to afford a compound of formula 1D, which is coupled with R-boronic acid, wherein R is 4-CHC$_6$H$_4$— or 3-AcC$_6$H$_4$— in the presence of tetrakis(triphenylphosphine)palladium catalyst to give compounds of formula 1E and 2, respectively. A compound of formula 1A-b is treated with acetic anhydride and triethyl amine to provide a compound of formula 5A. A compound of formula 5A is demethylated with aluminum chloride to afford a compound of formula 5B. Compound 5B is treated with R—Cl, wherein R is Ph—CH$_2$— or Ph—CO— to give compounds of formula 5C and 6, respectively.

Scheme 2

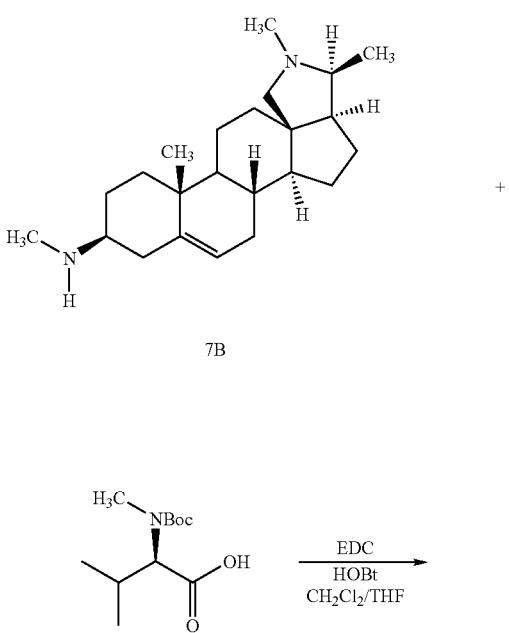

-continued

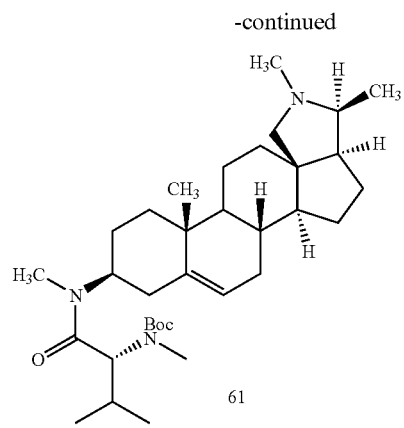

61

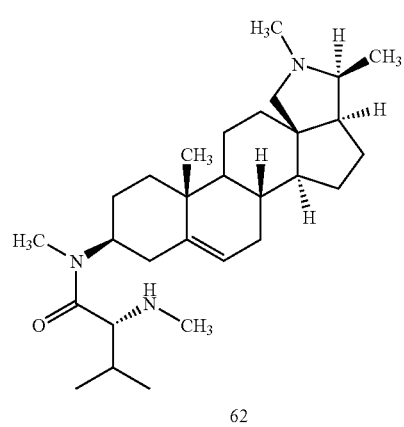

62

TFA/CH₂Cl₂ →

CH₃COCl / Et₃N, CH₂Cl₂ →

-continued

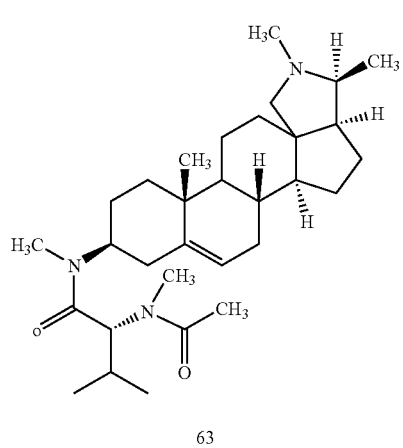

63

Compounds of formulas 61, 62, and 63 are prepared as described above in Scheme 2. A compound of formula 7B are treated with BOC-N-methyl-D-valine in the presence of 1-[3-(dimethylamino)propyl]-3-ethylcarbodiimide hydrochloride and 1-hydroxybenzotriazole to provide a compound of formula 61. Compound 61 is deprotected with trifluoroacetic acid to provide a compound of formula 62. Compound 62 undergoes addition by treatment with acetyl chloride to provide a compound of formula 63.

Scheme 3

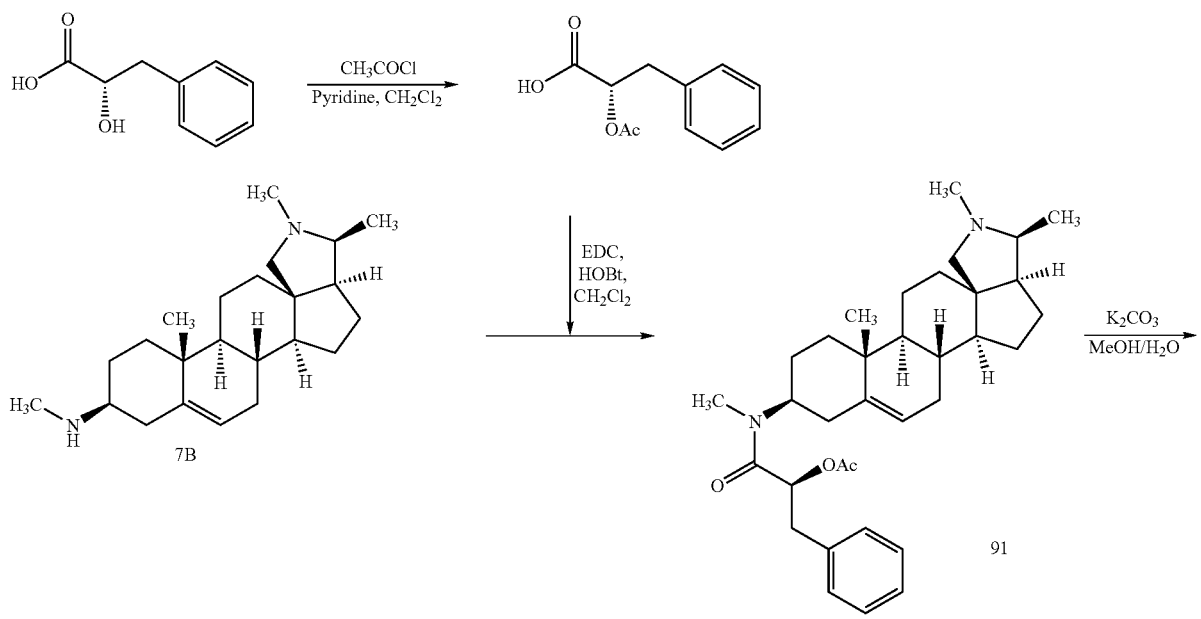

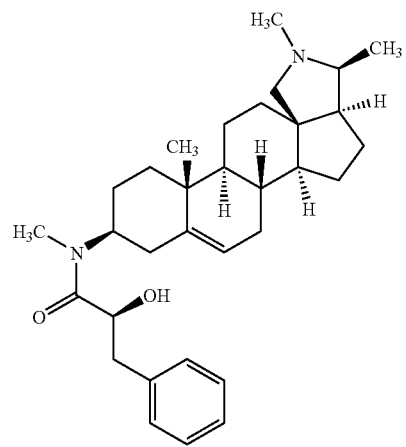

Compounds of formula 91 and 92 are prepared as described in Scheme 3. A compound of formula 7B are reacted with L-2-acetoxy-3-phenyl-propionic acid, which can be prepared from L-3-phenyllactic acid in a suspension with acetyl chloride and pyridine in a suitable solvent, for example dichloromethane, to afford a compound of formula 91. Compound 91 is hydrolyzed under basic conditions using potassium carbonate and methanol to provide a compound of formula 92.

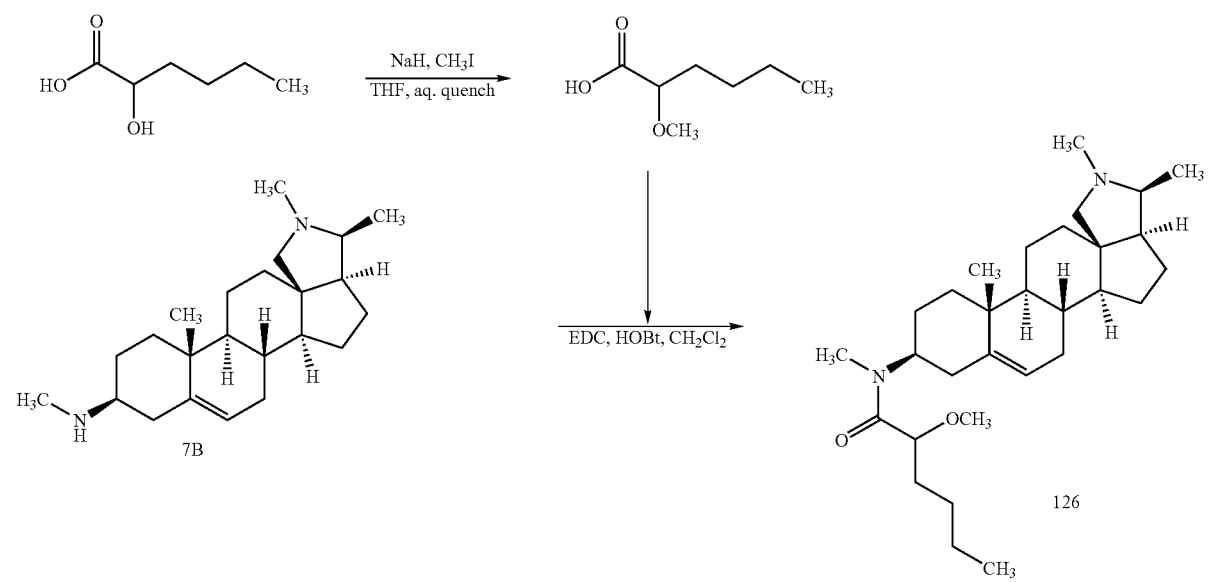

A compound of formula 126 is prepared as shown in Scheme 4. A compound of formula 7B is reacted with 2-methoxy caproic acid in the presence of 1-[3-(dimethylamino)propyl]-3-ethylcarbodiimide hydrochloride and 1-hydroxybenzotriazole to afford a compound of formula 126.

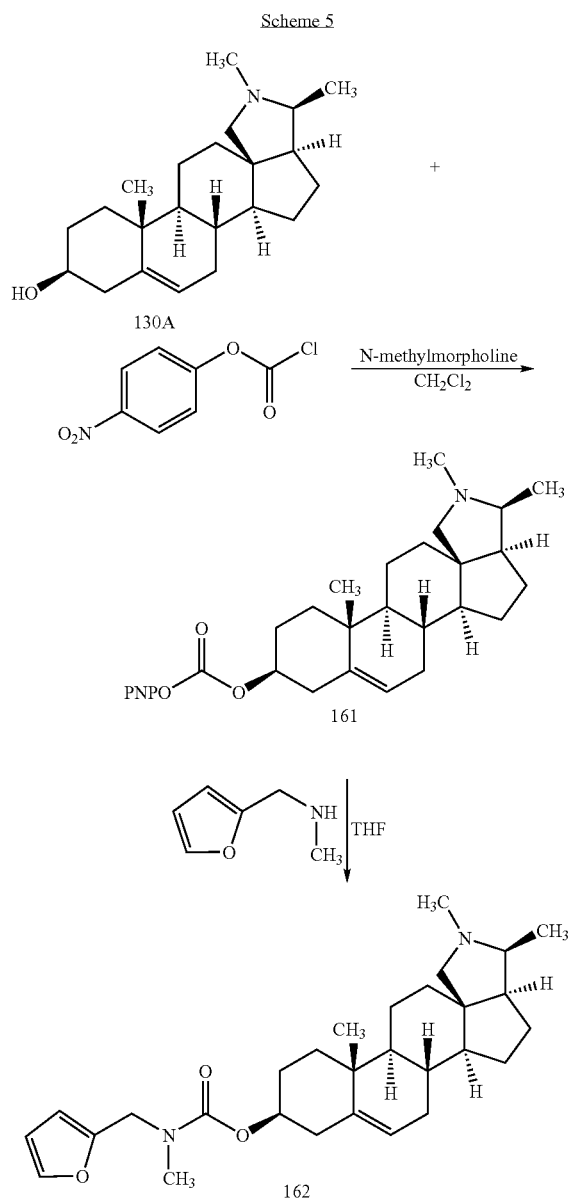

Compounds of formulas 161 and 162 are prepared as described in Scheme 6. A compound of formula 130A, which is prepared according to procedures described in Hora and Cerny; Collect. Czech. Chem. Commun. 26, 2217 (1961) and Labler et al. Collect. Czech. Chem. Commun. 28; 2015 (1963), are reacted with 4-nitrophenylchloroformate in the presence of N-methylmorpholine to provide compounds of formula 161. A compound of formula 161 is treated with N-methylfurylamine to provide a compound of formula 162.

The processes for making compounds described herein can be used in conjunction with the individual Examples to provide a variety of compounds within the scope of the claimed compounds and compounds useful for the claimed methods. In particular, suitable starting materials can be substituted in the Schemes and Examples described to provide compounds not specifically described in the Schemes and/or Examples without undue experimentation.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, carbonic, fumaric, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection or for rectal administration.

The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally," as used herein, refers to modes of administration, including intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutand, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug can depend upon its rate of dissolution, which, in turn, may depend upon crystal size and crystalline form. Alternatively, a parenterally administered drug form can be administered by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactidepolyglycolide. Depending upon the ratio of drug to polymer and the nature of the particular polymer employed, the rate of drug release can be controlled. Examples of other biodegradable polymers include poly (orthoesters) and poly(anhydrides) Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such asagar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and-mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N. Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants which can be required. Opthalmic formulations, eye ointments, powders and solutions are also contemplated as being within the scope of this invention. Aqueous liquid compositions of the invention also are particularly useful.

The compounds of the invention can be used in the form of pharmaceutically acceptable salts, esters, or amides derived from inorganic or organic acids. The term "pharmaceutically acceptable salts, esters and amides," as used herein, refer to carboxylate salts, amino acid addition salts, zwitterions, esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, mabate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, and citric add.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The term "pharmaceutically acceptable ester," as used herein, refers toesters of compounds of the invention which hydrolyze in vivo and include those that break down readily in the human body to leave the parent compound or a salt thereof. Examples of pharmaceutically acceptable, nontoxic esters of the invention include $C_1$-to-$C_6$ alkyl esters and $C_5$-to-$C_7$ cycloalkyl esters, although $C_1$-to-$C_4$ alkyl esters are preferred. Esters of the compounds of formula (I) may be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyliodide, benzyl iodide, cyclopentyl iodide. They also may be prepared by reaction of the compound with an acid such as hydrochloric acid and an alkylcarboxylic acid such as acetic acid, or with acid and an arylcarboxylic acid such as benzoic acid.

The term "pharmaceutically acceptable amide," as used herein, refers to non-toxic amides of the invention derived from ammonia, primary $C_1$-to-$C_6$ alkyl amines and secondary $C_1$-to-$C_6$ dialkyl amines. In the case of secondary amines, the amine may also be in the form of a 5- or 6-membered heterocycle containing one nitrogen atom. Amides derived from ammonia, $C_1$-to-$C_3$ alkyl primary amides and $C_1$-to-$C_2$ dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aryl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The term "pharmaceutically acceptable prodrug" or "prodrug," as used herein, represents those prodrugs of the compounds of the invention which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the invention may be rapidly transformed in vivo to a parent compound of formula (I), for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987), hereby incorporated by reference.

The invention contemplates pharmaceutically active compounds either chemically synthesized or formed by in vivo biotransformation to compounds of formula (I).

Methods of the Invention

Compounds and compositions of formulas (IA), (IB), and (II) as described for the invention are useful for modulating the effects of histamine-3 receptors. In particular, the compounds and compositions of the invention can be used for treating and preventing disorders modulated by the histamine-3 receptors. Typically, such disorders can be ameliorated by selectively modulating the histamine-3 receptors in a mammal, preferably by administering a compound or composition of the invention, either alone or in combination with another active agent as part of a therapeutic regimen.

The compounds of the invention, including but not limited to those specified in the examples, possess an affinity for the histamine-3 receptors. As histamine-3 receptor ligands, the compounds of the invention may be useful for the treatment and prevention of diseases or conditions such as acute myocardial infarction, Alzheimer's disease, asthma, attention-deficit hyperactivity disorder, bipolar disorder, cognitive enhancement, cognitive deficits in psychiatric disorders, deficits of memory, deficits of learning, dementia, cutaneous carcinoma, drug abuse, diabetes, type II diabetes, depression, epilepsy, gastrointestinal disorders, inflammation, insulin resistance syndrome, jet lag, medullary thyroid carcinoma, melanoma, Meniere's disease, metabolic syndrome, mild cognitive impairment, migraine, mood and attention alteration, motion sickness, narcolepsy, neurogenic inflammation, obesity, obsessive compulsive disorder, pain, Parkinson's disease, polycysfic ovary syndrome, schizophrenia, seizures, septic shock, sleep disorders, Syndrome X, Tourette's syndrome, vertigo, and wakefulness.

The ability of the compounds of the invention, including, but not limited to, those specified in the examples, to treat septic shock and cardiovascular disorders, in particular, acute myocardial infarction may be demonstrated by Imamura et al., Circ. Res., 78:475-481 (1996); Imamura et. al., Circ. Res., 78:863869 (1996); R. Levi and N. C. E. Smith, "Histamine $H_3$-receptors: A new frontier in myocardial ischemia", J. Pharm. Exp. Ther., 292:825-830 (2000); and Hatta, E., K. Yasuda and R. Levi, "Activation of histamine $H_3$ receptors inhibits carrier-mediated norepinephrine release in a human model of protracted myocardial ischemia", J. Pharm. Exp. Ther., 283:494-500 (1997).

The ability of the compounds of the invention, including, but not limited to, those specified in the examples, to treat sleep disorders, in particular, narcolepsy may be demonstrated by Lin et al., Brain Res., 523:325-330 (1990); Monti, et al., Neuropsychopharmacology 15:31-35 (1996); Sakai, et al., Life Sci.,48:2397-2404 (1991); Mazurkiewicz-Kwilecki and Nsonwah, Can. J. Physiol. Pharmacol.,67:75-78 (1989); Wada, et al., Trends in Neuroscience 14:415 (1991); and Monti, et al., Eur. J. Pharmacol. 205:283 (1991).

The ability of the compounds of the invention, including, but not limited to, those specified in the examples, to treat cognition and memory process disorders may be demonstrated by Mazurkiewicz-Kwilecki and Nsonwah, Can. J. Physiol. Pharmacol., 67:75-78 (1989); P. Panula, et al., Neuroscience, 82:993-997 (1997); Haas, et al., Behav. Brain Res., 66:41-44 (1995); De Almeida and Izquierdo, Arch. Int. Pharmacodyn., 283:193-198 (1986); Kamei et al., Psychopharmacology, 102:312-318 (1990); Kamei and Sakata, Jpn. J. Pharmaceutical., 57:437-482 (1991); Schwartz et al., Psychopharmacology, The fourth Generation of Progress. Bloom and Kupfer (eds). Raven Press, New York, (1995) 397; and Wada, et al., Trends in Neurosci., 14:415 (1991).

The ability of the compounds of the invention, including, but not limited to, those specified in the examples, to treat attention-deficit hyperactivity disorder (ADHD) may be demonstrated by Shaywitz et al., Psychopharmacology, 82:73-77 (1984); Dumery and Blozovski, Exp. Brain Res., 67:61-69 (1987); Tedford et al., J. Pharmacol. Exp. Ther., 275:598-604 (1995); Tedford et al., Soc. Neurosci. Abstr., 22:22 (1996); and Fox, et al., Behav. Brain Res., 131:151-161 (2002).

The ability of the compounds of the invention, including, but not limited to, those specified in the examples, to treat seizures, in particular, epilepsy may be demonstrated by Yokoyama, et al., Eur. J. Pharmacol., 234:129 (1993); Yokoyama and Iinuma, CNS Drugs 5:321 (1996); Onodera et al., Prog. Neurobiol., 42:685 (1994); R. Leurs, R. C. Vollinga and H. Timmerman, "The medicinal chemistry and therapeutic potential of ligands of the histamine $H_3$ receptor", Progress in Drug Research 45:107-165, (1995); Leurs and Timmerman, Prog. Drug Res., 39:127 (1992); The Histamine H$_3$ Receptor, Leurs and Timmerman (eds), Elsevier Science, Amsterdam, The Netherlands (1998); H. Yokoyama and K. Iinuma, "Histamine and Seizures: Implications for the treatment of epilepsy", CNS Drugs, 5(5): 321-330 (1995); and K. Hurukami, H. Yokoyama, K. Onodera, K. Iinuma and T. Watanabe, "AQ-0145, A newly developed histamine H$_3$ antagonist, decreased seizure susceptibility of electrically induced convulsions in mice", Meth. Find. Exp. Clin. Pharmacol., 17(C):70-73 (1995).

The ability of the compounds of the invention, including, but not limited to, those specified in the examples, to treat motion sickness, Alzheimer's disease, and Parkinson's disease may be demonstrated by Onodera, et al., Prog. Neurobiol., 42:685 (1994); Leurs and Timmerman, Prog. Drug Res., 39:127 (1992); and The Histamine H$_3$ Receptor, Leurs and Timmerman (eds), Elsevier Science, Amsterdam, The Netherlands (1998).

The ability of the compounds of the invention, including, but not limited to, those specified in the examples, to treat narcolepsy, schizophrenia, depression, and dementia may be demonstrated by R. Leurs, R. C. Vollinga and H. Timmerman, "The medicinal chemistry and therapeutic potential of ligands of the histamine H$_3$ receptor", Progress in Drug Research 45:107-165 (1995); The Histamine H$_3$ Receptor, Leurs and Timmerman (eds), Elsevier Science, Amsterdam, The Netherlands (1998); and Perez-Garcia C, et. al., and Psychopharmacology (Berlin) 142(2):215-20 (February 1999).

The ability of the compounds of the invention, including, but not limited to, those specified in the examples, to treat wakefulness, cognitive enhancement, mood and attention alteration, vertigo and motion sickness, and treatment of cognitive deficits in psychiatric disorders may be demonstrated by Schwartz, Physiol. Review 71:1-51 (1991).

The ability of the compounds of the invention, including, but not limited to, those specified in the examples, to treat mild cognitive impairment, deficits of memory, deficits of learning and dementia may be demonstrated by C. E. Tedford, in "The Histamine H$_3$ Receptor: a target for new drugs", the Pharmacochemistry Library, vol. 30 (1998) edited by R. Leurs and H. Timmerman, Elsevier (New York). p. 269 and references also contained therein.

The ability of the compounds of the invention, including, but not limited to, those specified in the examples, to treat obesity may be demonstrated by Leurs, et al., Trends in Pharm. Sci., 19:177-183 (1998); E. Itoh, M. Fujimiay, and A. Inui, "Thioperamide, A histamine H$_3$ receptor antagonist, powerfully suppresses peptide YY-induced food intake in rats," Biol. Psych., 45(4):475-481 (1999); S. I. Yates, et al., "Effects of a novel histamine H$_3$ receptor antagonist, GT-2394, on food intake and weight gain in Sprague-Dawley rats," Abstracts, Society for Neuroscience, 102.10: 219 (November, 2000); and C. Bjenning, et al., "Peripherally administered ciproxifan elevates hypothalamic histamine levels and potently reduces food intake in the Sprague Dawley at," Abstracts, International Sendai Histamine Symposium, Sendai, Japan, #P39 (November, 2000).

The ability of the compounds of the invention, including, but not limited to, those specified in the examples, to treat inflammation and pain may be demonstrated by Phillips, et al., Annual Reports in Medicinal Chemistry 33:31-40 (1998).

The ability of the compounds of the invention, including, but not limited to, those specified in the examples, to treat migraine may be demonstrated by R. Leurs, R. C. Vollinga and H. Timmerman, "The medicinal chemistry and therapeutic potential of ligands of the histamine H$_3$ receptor," Progress in Drug Research 45:107-165 (1995); Matsubara, et al., Eur. J. Pharmacol., 224:145 (1992); and Rouleau, et al., J. Pharmacol. Exp. Ther., 281:1085 (1997).

The ability of the compounds of the invention, including, but not limited to, those specified in the examples, to treat cancer, in particular, melanoma cutaneous carcinoma and medullary thyroid carcinoma may be demonstrated by Polish Med. Sci. Mon., 4(5):747 (1998);Adam Szelag, "Role of histamine H$_3$-receptors in the proliferation of neoplastic cells in vitro," Med. Sci. Monit., 4(5):747-755 (1998); and C. H. Fitzsimons, et al., "Histamine receptors signalling in epidermal tumor celllines with H-ras gene alterations," Inflammation Res., 47 (Suppl 1):S50-S51 (1998).

The ability of the compounds of the invention, including, but not limited to, those specified in the examples, to treat vestibular dysfunctions, in particular, Meniere's disease may be demonstrated by R. Leurs, R. C. Vollinga and H. Timmerman, "The medicinal chemistry and therapeutic potential of ligands of the histamine H$_3$ receptor," Progress in Drug Research 45:107-165 (1995).

The ability of the compounds of the invention, including, but not limited to, those specified in the examples, to treat asthma may be demonstrated by A. Delaunois A., et al., "Modulation of acetylcholine, capsaicin and substance P effects by histamine H$_3$ receptors in isolated perfused rabbit lungs," European Journal of Pharmacology 277(2-3):243-250 (1995); and Dimitriadou, et al., "Functional relationship between mast cells and C-sensitive nerve fibres evidenced by histamine H$_3$-receptor modulation in rat lung and spleen," Clinical Science 87(2):151-163 (1994).

The ability of the compounds of the invention, including, but not limited to, those specified in the examples, to allergic rhinitis may be demonstrated by McLeod, et al., Progress in Resp. Research 31:133 (2001).

Compounds of the invention are particularly useful for treating and preventing a condition or disorder affecting the memory or cognition.

Actual dosage levels of active ingredients in the pharmaceutical compositions of this invention can be varied so as to obtain an amount of the active compound(s) which is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt, ester, amide or prodrug form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The total daily dose of the compounds of this invention administered to a human or lower animal may range from about 0.003 to about 30 mg/kg/day. For purposes of oral administration, more preferable doses can be in the range of from about 0.1 to about 15 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples and reference examples, which are intended as an illustration of and not a limitation upon the scope of the invention.

EXAMPLES

Example 1

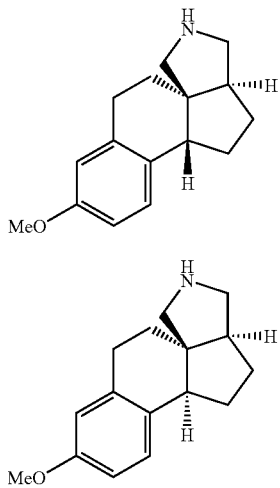

1A-a 1A-b 1A. 2-Methoxy-5,6,6a,7,8,9,10,11-octahydro-4bH-benzo[4,5]indeno[1,7ac]pyrrole (1A-a and 1A-b)

8-Benzyl-2-methoxy-6a,7,8,9,10,11-hexahydro-6-H-benzo[4,5]indeno[1,7a-c]pyrrole (prepared according to the procedure of Kopach, M. E.; Fray, A. H. and Meyers A. I., J. Am. Chem. Soc. 1996, 118, 9876)(1.0 g, 3.0 mmol) and 10% Pd/C (200 mg) were stirred in ethanol (30 mL) under hydrogen for 2 h. The reaction mixture was filtered and concentrated in vacuo to provide 617.8 mg (84.2%) of the title compounds 1A-a and 1A-b as a 3:1 mixture.

MS: (M+H)$^+$=244.

The mixture was separated by column chromatography on silica gel using 5% methanol and 0.5% ammonium hydroxide in dichloromethane provided pure 1Aa and 1A-b.

1A-a: $^1$H NMR (CDCl$_3$): δ 7.08 (d, 1H, J=14.0 Hz), 6.73 (dd, 1H, J=14.0, 4.5 Hz), 6.62 (d, 1H, J=4.5 Hz), 3.77 (s, 3H), 3.01 (dd, 1H, J=18.0, 12 Hz), 2.89 (d, 1H, J=18 Hz), 2.74 (dd, 1H, J=19, 5.5Hz), 2.6-2.83 (m, 2H), 2.60 (d, 1H, J=19 Hz), 2.13-2.21 (m, 2H), 1.79-1.98 (m, 4H), 1.50-1.68 (m, 2H), 1.33 (m, 1 H). MS: (M+H)$^+$=244.

1A-b: $^1$H NMR (CDCl$_3$): δ 6.98 (dd, 1H, J=8.7, 1.2 Hz), 6.66 (s, 1H), 6.64 (d, 1H, J=3.0 Hz), 3.76 (s, 3H), 3.16 (dd, 1H, J=11.5, 6.0 Hz), 3.00 (dd, 1H, J=19, 9.0 Hz), 2.92 (dd, 1 H, J=18, 9.0 Hz), 2.89 (m, 1 H), 2.84 (dd, 1 H, J=11.0, 2.0 Hz), 2.55 (d, 1H, J=12.0 Hz), 2.45 (d, J=12.0 Hz), 2.24 (m, 1H), 2.13 (m, 2H), 2.04 (ddd, 1H, J=12.7, 8.2, 2.5 Hz). 1.91 (m. 1H), 1.58 (m, 1H), 1.56 (m, 1H). MS: (M+H)$^+$=244.

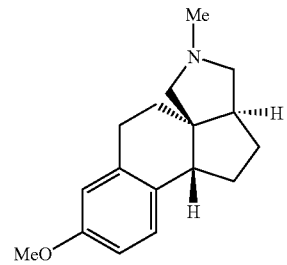

1B. 2-Methoxy-8-methyl-5,6,6a,7,8,9,10,11-octahydro-4bH-benzo[4,5]indeno[1,7a-c]pyrrole 2-Methoxy-5,6,6a,7,8,9,10,11-octahydro-4bH-benzo[4,5]indeno[1,7a-c]pyrrole (Example 1A, compound 1A-a) (220.0 mg, 0.90 mmol) and paraformaldehyde (810 mg, 2.7 mmol) were stirred in methanol (10 mL) at rt for 30 min. NaBH$_3$CN was added and stirring was continued for 30 min. The mixture was quenched with 1N NaOH (10 mL), extracted with CH$_2$Cl$_2$ (20 mL×4). The combined organic layers were dried over sodium sulfate, filtered and concentrated in vacuo providing 230.1 mg (98.9%) of the title compound 1B as a white solid.

$^1$H NMR (CDCl$_3$): δ 7.08 (d, 1H, J=8.4 Hz), 6.72 (dd, 1H, J=10.5, 2.1 Hz). 6.62 (s, 1H), 3.77 (s, 3H), 2.92 (m, 1H), 2.73 (m, 1H), 2.64 (m, 2H), 2.44 (m, 1H), 2.34 (s, 3H), 2.15 (m, 2H), 2.04 (m, 1H), 1.95 (m, 1H), 1.79 (m, 1H), 1.68 (m, 1H), 1.55 (m, 3H). MS: (M+H)$^+$=258.

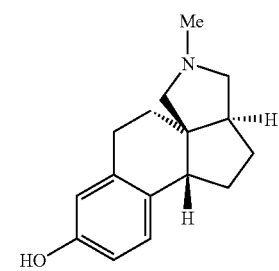

1C. 8-Methyl-5,6,6a,7,8,9,10,11-octahydro-4bH-benzo[4,5]indeno[1,7a-c]pyrrol-2-ol 2-Methoxy-8-methyl-5,6,6a,7,8,9,10,11-octahydro-4bH-benzo[4,5]indeno[1,7a-c]pyrrole (Example 1B) (190.0 mg, 0.74 mmol) and tetrabutylammonium iodide (300 mg, 0.81 mmol) were dissolved in $CH_2Cl_2$ (20 mL) and cooled to −78° C. $BCl_3$ (1.85 mL, 1M in $CH_2Cl_2$) was added dropwise. The mixture was stirred at 0° C. for 5 hrs. It was then quenched with aq. satd. $NaHCO_3$, extracted with $CH_2Cl_2$ (15 mL×4). The combined organic layers were dried over sodium sulfate, filtered and concentrated in vacuo. The residue was purified by column chromatography on silica gel using 5% methanol in dichloromethane, providing 57.1 mg (31.8%) of the title compound 1C.

$^1$H NMR (DMSO-$d_6$): δ 9.10 (s, 1H), 6.96 (d, 1H, J=18.5 Hz), 6.57 (dd, 1H, J=14, 3.5 Hz), 6.48 (s, 3H), 1.29-3.50 (m, 14H). MS: (M+H)$^+$=244.

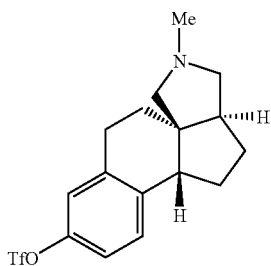

1D. Trifluoro-methanesulfonic acid 8-methyl-5,6,6a,7,8,9,10,11-octahydro-4bH-benzo[4,5]indeno[1,7a-c]pyrrol-2-yl ester 8-Methyl-5,6,6a,7,8,9,10,11-octahydro-4bH-benzo[4,5]indeno[1,7a-c]pyrrol-2-ol (Example 1C) (54.0 mg, 0.22 mmol) and triethylamine (42 µL, 0.30 mmol) were dissolved in $CH_2Cl_2$ (10 mL) and cooled to −78° C. Trifluoromethane sulfonic anhydride (42 µL, 0.24 mmol) was added dropwise. The mixture was stirred at 0° C. for 1 hr. It was then quenched with water (2 mL), extracted with $CH_2Cl_2$ (10 mL×3). The combined organic layers were dried over sodium sulfate, filtered and concentrated in vacuo. The residue was purified by column chromatography on silica gel using 10% methanol in dichloromethane, providing (70.0 mg, 85.0%) of the title compound 1D.

MS: (M+H)$^+$=376.

1E. 4-(8-Methyl-5,6,6a,7,8,9,10,11-octahydro-4bH-benzo[4,5]indeno[1,7a-c]pyrrol-2-yl)-benzonitrile Trifluoro-methanesulfonic acid 8-methyl-5,6,6a,7,8,9,10,11-octahydro-4bH-benzo[4,5]indeno[1,7a-c]pyrrol-2-yl ester (Example 1D) (23.0 mg, 0.061 mmol) and 4-cyanophenylboronic acid (18 mg, 0.122 mmol) were dissolved in toluene (2 mL) and ethanol (0.5 mL). 0.15 mL of 1M $Na_2CO_3$ solution was added. Nitrogen was bubbled through the reaction mixture for 10 min. Tetrakis(triphenylphosphine)palladium (7.1 mg, 0.006 mmol) was then added. The mixture was stirred at 90° C. for 20 h. The reaction mixture was quenched with water (2 mL), extracted with $CH_2Cl_2$ (5 mL×4). The combined organic layers were dried over sodium sulfate, filtered and concentrated in vacuo. The residue was purified by column chromatography on silica gel twice using 10% methanol in dichloromethane and 0.5% ammonium hydroxide and 5% methanol in dichloromethane, providing 6.2 mg (30.8%) of the title compound 1E.

$^1$H NMR (CDCl$_3$): δ 7.68 (q, 4H), 7.37 (dd, 1H), 7.29-7.31 (m, 2H), 3.33-1.25 (m, 17H). MS: (M+H)$^+$=329.

Example 2

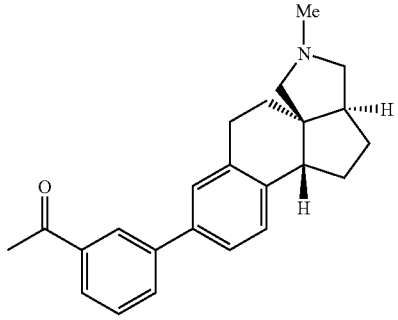

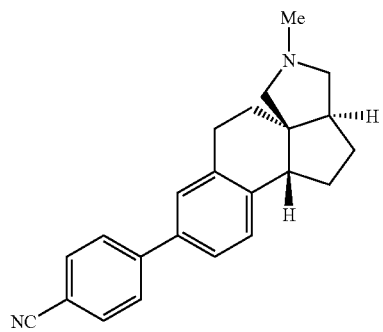

1-[3-(8-Methyl-5,6,6a,7,8,9,10,11-octahydro-4bH-benzo[4,5]indeno[1,7a-c]pyrrol-2-yl)-phenyl]-ethanone Using the procedure of Example 1E, but replacing 4-cyanophenylboronic acid with 3-acetylphenylboronic acid, provided, after silica gel chromatography using 5% methanol in dichloromethane, 3.9 mg (14.1%) of the title compound as a yellow oil.

1H NMR (CDCl$_3$): δ 1.53-3.05 (m, 14 H) 2.34 (s, 3 H) 2.65 (s, 3 H) 7.00 (m, 1 H) 7.34 (d, J=1.50 Hz, 1 H) 7.40 (dd, J=8.48, 1.50 Hz, 1 H) 7.51 (t, J=7.80 Hz, 1 H) 7.77 (d, J=8.48 Hz, 1 H) 7.91 (d, J=7.80 Hz, 1 H) 8.16 (m, 1 H) MS: (M+H)$^+$=346.

Example 3

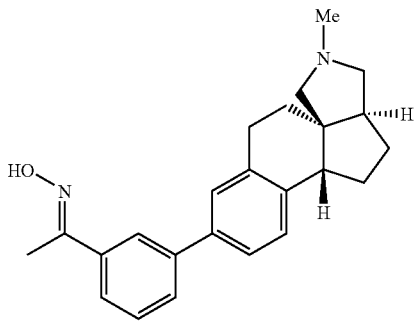

1-[3-(8-Methyl-5,6,6a,7,8,9,10,11-octahydro-4bH-benzo[4,5]indeno[1,7a-c]pyrrol-2-yl)-phenyl]-ethanone oxime 1-[3-(8-Methyl-5,6,6a,7,8,9,10,11-octahydro-4bH-benzo[4,5]indeno[1,7a-c]pyrrol-2-yl)-phenyl]-ethanone (Example 2)(10.0 mg, 0.028 mmol), hydroxylamine hydrochloride (2.9 mg, 0.042 mmol), and pyridine (226 μL, 0.28 mmol) were heated in ethanol (1 mL) at 80° C. for 3 h. The mixture was quenched with water (1 mL), extracted with $CH_2Cl_2$ (2 mL×4). The combined organic layers were dried over sodium sulfate, filtered and concentrated in vacuo. The residue was purified by column chromatography on silica gel using 5% methanol in dichloromethane, providing 1.9 mg (18.3%) of the title compound.

$^1$H NMR ($CDCl_3$): δ 7.83 (s, 1 H), 7.58 (m, 2H), 7.44-7.36 (m, 2 H), 7.32 (s, 1 H), 7.23 (m, 1 H), 3.02 (m, 1H), 2.74 (s, 3H), 2.32 (s, 3H) 2.82-1.48 (m, 13H). MS: $(M+H)^+$ =361.

Example 4

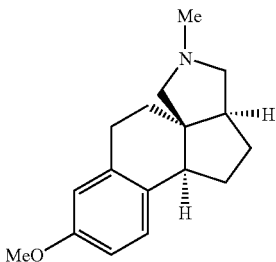

4A. 2-Methoxy-8-methyl-5,6,6a,7,8,9,10,11-octahydro-4bH-benzo[4,5]indeno[1,7a-c]pyrrole Using the procedure of Example 1B but replacing the resultant compound of Example 1A (Compound 1A-a) with the resultant compound of Example 1A(Compound 1A-b), provided, after silica gel chromatography using 5% methanol and 0.5% ammonium hydroxide in dichloromethane, 102.0 mg (88.5%) of the title compound as a white solid.

$^1$H NMR ($CDCl_3$): δ 7.00 (d, 1H, J=9.15 Hz, 1 H), 6.67 (s, 1 H). 6.66 (d, J=6.44 Hz, 1 H), 3.77 (s, 3H), 2.95 (m, 2H), 2.72 (m, 2H), 2.44 (m, 1H), 2.22 (s, 3H), 2.07-1.55 (m, 9H). MS: $(M+H)^+$=258.

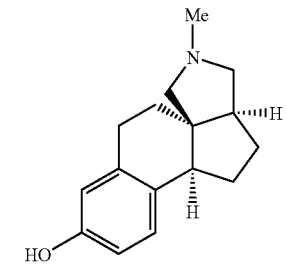

4B. 8-Methyl-5,6,6a,7,8,9,10,11-octahydro-4bH-benzo[4,5]indeno[1,7a-c]pyrrol-2-ol Using the procedure of Example 1C, but replacing the resultant compound of Example 1B with the resultant compound of Example 4A, provided, after silica gel chromatography using 5% methanol and 0.5% ammonium hydroxide in dichloromethane, 26.0 mg (27.5%) of the title compound as a colorless oil.

$^1$H NMR (DMSO-$d_6$): δ 9.10 (s, 1H), 6.96 (d, 1H, J=18.5 Hz), 6.57 (dd, 1H, J=14, 3.5 Hz), 6.48 (s, 3H), 1.29-3.50 (m, 14H). MS: $(M+H)^+$=244.

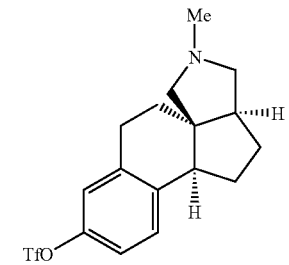

4C. Trifluoro-methanesulfonic acid 8-methyl-5,6,6a,7,8,9,10,11-octahydro-4bH-benzo[4,5]indeno[1,7a-c]pyrrol-2-yl ester Using the procedure of Example 1D, but replacing the resultant compound of Example 1C with the resultant compound of Example4B, provided, after silica gel chromatography using 10% methanol in dichloromethane, 50.2 mg (100%) of the title compound as a colorless oil.

MS: $(M+H)^+$=376.

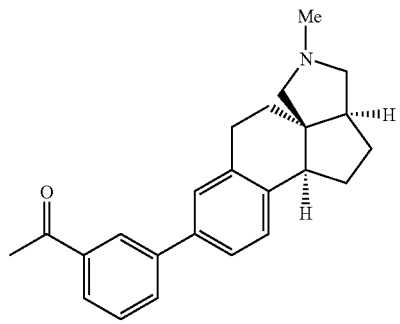

4D. 1-[3-(8-Methyl-5,6,6a,7,8,9,10,11-octahydro-4bH-benzo[4,5]indeno[1,7a-c]pyrrol-2-yl)-phenyl]-ethanone Using the procedure of Example 1E, but replacing 4-cyanophenylboronic acid with 3-acetylphenylboronic acid and replacing the resultant compound of Example 1D with the resultant compound of Example 4C, provided, after silica gel chromatography using 5% methanol in dichloromethane, 5.3 mg (15.3%) of the title compound as a yellow oil.

1H NMR (CDCl$_3$): δ 2.47 (s, 3 H) 2.65 (s, 3 H) 0.85-3.14 (m, 14 H) 7.00 (m, 2 H) 7.13 (m, 1 H) 7.48 (m, 1 H) 7.98 (m, 1 H) 8.14 (m, 1 H) 8.53 (m, 1 H) MS: (M+H)$^+$=346.

Example 5

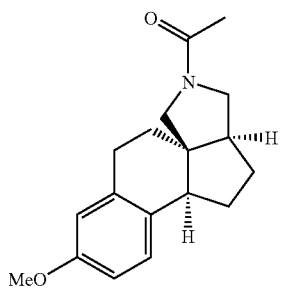

5A. 1-(2-Methoxy-5,6,6a,7,10,11-hexahydro-4bH-benzo[4,5]indeno[1,7a-c]pyrrol-8-yl)-ethanone 2-Methoxy-5,6,6a,7,8,9,10,11-octahydro-4bH-benzo[4,5]indeno[1,7a-c]pyrrole (Example 1A, compound 1A-b) (50.0 mg, 0.21 mmol) and triethylamine (86 μL, 0.61 mmol) were dissolved in CH$_2$Cl$_2$ (2 mL). Acetic anhydride (24 μl, 0.25 mmol) was added dropwise. The mixture was stirred at rt for 2 hr. It was then quenched with water (2 mL), and extracted with CH$_2$Cl$_2$ (5 mL×3). The combined organic layers were dried over sodium sulfate, filtered, and concentrated in vacuo. The residue was purified by column chromatography on silica gel using 5% methanol in dichloromethane, providing 59.1 mg (100%) of the title compound.

1H NMR (CDCl$_3$): δ 1.59 (s, 3 H) 3.68 (d, J=12.21 Hz, 14 H) 3.77 (m, 3 H) 6.68 (m, 2 H) 6.99 (m, 1 H) MS: (M+H)$^+$=286

5B. 1-(2-Hydroxy-5,6,6a,7,10,11-hexahydro-4bH-benzo[4,5]indeno[1,7a-c]pyrrol-8-yl)-ethanone 1-(2-Methoxy-5,6,6a,7,10,11-hexahydro-4bH-benzo[4,5]indeno[1,7a-c]pyrrol-8-yl)-ethanone (Example 5A) (55.0 mg, 0.19 mmol) was dissolved in ethanethiol (4 mL). Aluminum chloride powder (128 mg, 0.96 mmol) was added. The mixture was stirred at 0° C. for 1 h, quenched with NaHCO$_3$ (satd.aq., 4 mL), and extracted with CH$_2$Cl$_2$ (5 mL×3). The combined organic layers were dried over sodium sulfate, filtered and concentrated in vacuo. The residue was purified by column chromatography on silica gel using 5% methanol in dichloromethane, providing 46.2 mg (88.3%) of the title compound.

MS: (M+H)$^+$=272

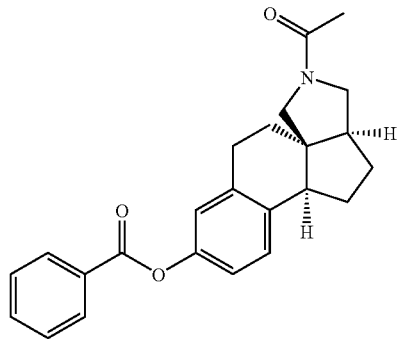

5C. Benzoic acid 8-acetyl-5,6,6a,7,8,9,10,11-octahydro-4bH-benzo[4,5]indeno[1,7a-c]pyrrol-2-yl ester 1-(2-Hydroxy-5,6,6a,7,10,11-hexahydro-4bH-benzo[4,5]indeno[1,7a-c]pyrrol-8-yl)-ethanone (Example 5B) (10.0 mg, 0.037 mmol) and triethylamine (15.4 μL, 0.11 mmol) were dissolved in CH$_2$Cl$_2$ (2 mL). Benzoyl chloride (5.1 μL, 0.044 mmol) was added dropwise. The mixture was stirred at rt for 12 hr, quenched with water (2 mL), and extracted with CH$_2$Cl$_2$ (5 mL×3). The combined organic layers were dried over sodium sulfate, filtered, and concentrated in vacuo. The residue was purified by column chromatography on silica gel using 5% methanol in dichloromethane, providing 11.1 mg (80.4%) of the title compound.

1H NMR (CDCl$_3$): δ 1.58 (s, 3 H) 1.72-3.43 (m, 13 H) 3.73 (m, 1 H) 6.97 (m, 2 H) 7.14 (m, 1 H) 7.52 (m, 2 H) 7.63 (m, 1 H) 8.19 (m, 2 H) MS: (M+H)$^+$=376

Example 6

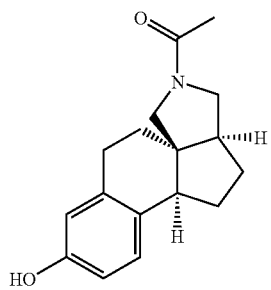

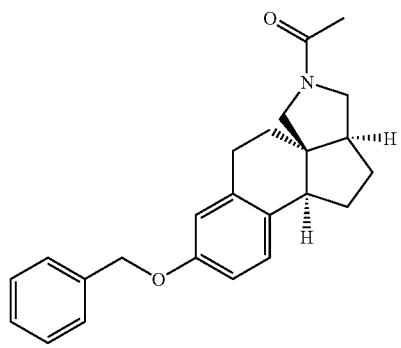

1-(2-Benzyloxy-5,6,6a,7,10,11-hexahydro-4bH-benzo[4,5]indeno[1,7a-c]pyrrol-8-yl)-ethanone 1-(2-Hydroxy-5,6,6a,7,10,11-hexahydro-4bH-benzo[4,5]indeno[1,7a-c]pyrrol-8-yl)-ethanone (Example 5B) (10.0 mg, 0.037 mmol) and potassium carbonate (25 mg, 0.18 mmol) were dissolved in DMF (0.5 mL). Benzyl chloride (10.2 μL, 0.088 mmol) and sodium iodide (5 mg) were added. The mixture was stirred at rt for 24 hr, quenched with water (2 mL), and extracted with $CH_2Cl_2$ (5 mL×3). The combined organic layers were dried over sodium sulfate, filtered, and concentrated in vacuo. The residue was purified by column chromatography on silica gel using 5% methanol in dichloromethane, providing 5.5 mg (41.3%) of the title compound.

1H NMR ($CDCl_3$): δ 1.57 (s, 3 H) 1.68-2.07 (m, 3 H) 2.31 (m, 2 H) 2.69 (dd, J=7.80, 6.44 Hz, 1 H) 2.96 (m, 3 H) 3.24 (m, 1 H) 3.46 (m, 1 H) 3.70 (m, 1 H) 5.03 (d, J=4.75 Hz, 2 H) 6.74 (m, 2 H) 6.99 (m, 1 H) 7.36 (m, 5 H) MS: $(M+H)^+=362$.

Reference Example 7

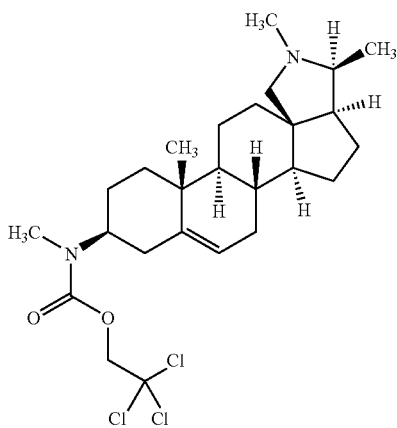

7A. Methyl-(2,3,11a-trimethyl-2,3,3a,4,5,5a,5b,6,8,9,10,11,11a,11b,12,13-hexadecahydro-1H-2-azapentaleno[1,6a-a]phenanthren-9-yl)carbamic acid 2,2,2-trichloro-ethyl ester 2,2,2-Trichloroethylchloroformate (5.94 g, 28 mmol) was added dropwise to a stirred solution of conessine (10 g, 28 mmol) in 200 mL benzene. Very thick gel resulted. The mixture was heated at reflux for 4 h (oil bath temperature 90° C.), then cooled down to room temperature, quenched with water, the pH adjusted with 25 mL saturated sodium bicarbonate, and extracted with dichloromethane 3×. Organic layers were dried over $Na_2SO_4$, filtered, and evaporated to give crude product, which was purified by flash chromatography to give desired product (8.8 g, 61% yield).

$^1$H NMR ($CDCl_3$): δ 5.35 (m, 1H), 4.74 (m, 2H), 3.90 (m, 1H), 3.75 (m, 2H), 3.34 (m, 1H), 2.92(s, 3H), 2.80 (d, 3H), 1.52 (s, 3H), 0.95 (s, 3H), 2.60-1.10 (m, 20H). MS (DCI): $(M+H)^+=517/519$

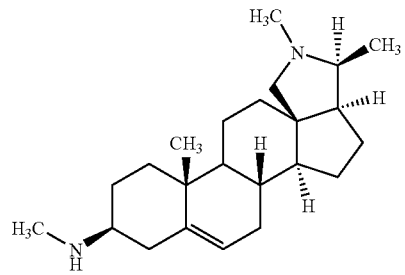

7B. Methyl-(2,3,11a-trimethyl-2,3,3a,4,5,5a,5b,6,8,9,10,11,11a,11b,12,13-hexadecahydro-1H-2-azapentaleno[1,6a-a]phenanthren-9-yl)amine 10% Pb/Cd couple* (1.2 g, 9 mmol Cd) was added to a rapidly stirred mixture of Troc-conessine (Reference Example 7A) (800mg, 1.54 mmol), THF (6 mL) and aq.1N $NH_4OAc$ (6 mL). The mixture was stirred for 5 h, then another portion of 10% Pb/Cd couple (1.0 g) was added, and stirred overnight. The solid was filtered, the filtrate was diluted with water, the pH adjusted with saturated sodium bicarbonate, and then extracted with dichloromethane 3×. The combined organic layer was dried over $Na_2SO_4$, filtered, and evaporated to give crude product, which was purified by flash chromatography using 0.5% ammonium hydroxide and 5% methanol in dichloromethane to give the desired product (397 mg, 75% yield).

\* Preparation of 10% Pb/Cd Couple:

Yellow lead oxide (PbO, 108 mg, 0.49 mmol) was dissolved in 5 mL 50% aq. ACOH, and the solution was slowly added to a vigorously stirred suspension of Cd dust (100 mesh, 546 mg, 4.9 mmol) in deionized water (10 mL). The Cd darkened as Pb deposited on its surface, and formed clumps that were gently broken up with a glass rod. The dark, nonpyrophoric Pb/Cd couple was filtered, washed with water, then acetone, vacuum dried, crushed and stored in a closed vessel. This gives the 10% Pb/Cd couple (4.9 mmol Cd in 654 mg couple).

$^1$H NMR ($CDCl_3$): δ 5.35 (m, 1H), 3.0 (d, 1H), 2.45 (s, 3H), 2.22 (s, 3H), 1.05 (d, 3H), 0.93 (s, 3H), 2.40-1.00 (m, 23H). MS (DCI): $(M+H)^+=343$

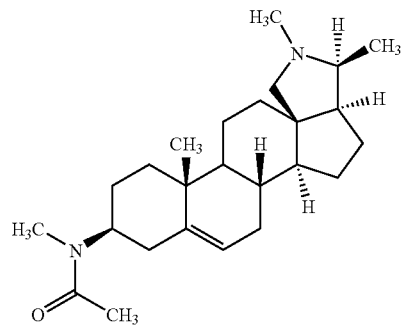

7C. N-Methyl-N-(2,3,11a-trimethyl-2,3,3a,4,5,5a,5b, 6,8,9,10,11,11a,11b,12,13-hexadecahydro-1H-2-aza-pentaleno[1,6a-a]phenanthren-9-yl)-acetamide A mixture of compound 7B (15 mg, 0.044 mmol), acetyl chloride (2.8 µL, 1.1 eq), triethylamine (15 µL, 3.0 eq) and dichloromethane (1 mL) was stirred at room temperature for 2 h. The clear solution was directly loaded on silica gel column and eluted with 0.5% ammonium hydroxide and 5% methanol in dichloromethane to give the desired product (10.5 mg, 78% yield)

$^1$H NMR (CDCl$_3$): δ 0.93 (m, 3 H) 1.08 (m, 3 H) 1.31 (m, 4 H) 1.57 (m, 3 H) 1.68 (m, 3 H) 1.87 (m, 7 H) 2.10 (m, 3 H) 2.23 (m, 3 H) 2.37 (m, 1 H) 2.52 (m, 1H) 2.80 (m, 3 H) 2.87 (m, 3 H) 3.35 (m, 1 H) 3.73 (m, 1 H) 5.36 (m, 1 H) MS: (M+H)$^+$=385

Reference Example 8

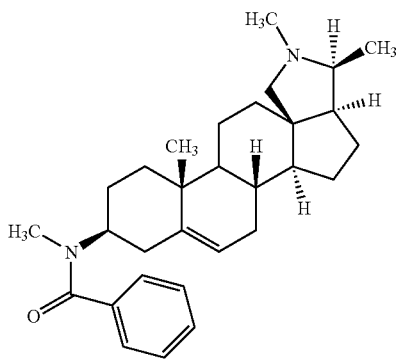

N-Methyl-N-(2,3,11a-trimethyl-2,3,3a,4,5,5a,5b,6,8, 9,10,11,11a,11b,1 2,13-hexadeca hydro-1H-2-aza-pentaleno[1,6a-a]phenanthren-9-yl)-benzamide The title compound was prepared according to the procedures described in Reference Example 7C, except substituting benzoyl chloride for acetyl chloride. MS: (M+H)$^+$=447

Example 9

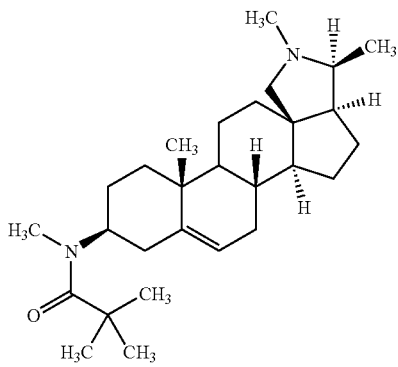

2,2, N-Trimethyl-N-(2,3,11a-trimethyl-2,3,3a,4,5,5a, 5b,6,8,9,10,11,11a,11b,12,13-hexadecahydro-1H-2-aza-pentaleno[1,6a-a]phenanthren9-yl)propionamide The title compound was prepared according to the procedures described in Reference Example 7C, except substituting trimethylacetyl chloride for acetyl chloride. $^1$H NMR (CDCl$_3$): δ 0.93 (m, 3 H) 1.08 (m, 3 H) 1.26 (s, 9H) 1.31 (m, 4 H) 1.57 (m, 3 H) 1.68 (m, 3 H) 1.87 (m, 6 H) 2.10 (m, 3 H) 2.23 (m, 3 H) 2.37 (m, 1 H) 2.52 (m, 1 H) 2.86 (s, 3 H) 3.35 (m, 1 H) 3.73 (m, 1 H) 4.02 (m, 1 H) 5.36 (m,$_1$ H); MS: (M+H)$^+$427.

Example 10

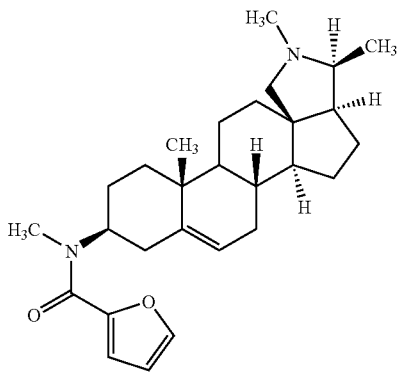

Furan-2-carboxylic acid methyl-(2,3,11a-trimethyl-2,3,3a,4,5,5a,5b,6,8,9,10,11, 11a,11b,12,13-hexadecahydro-1H-2-aza-pentaleno[1,6a-a]phenanthren-9-yl)-amide The title compound was prepared according to the procedures described in Reference Example 7C, except substituting 2-furoyl chloride for acetyl chloride. MS: (M+H)$^+$=437.

Example 11

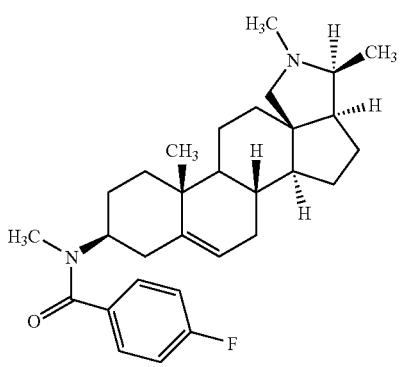

4-Fluoro-N-methyl-N-(2,3,11-a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide The title compound was prepared according to the procedures described in Reference Example 7C, except substituting 4-fluorobenzoyl chloride for acetyl chloride. MS: $(M+H)^+=465$.

Example 12

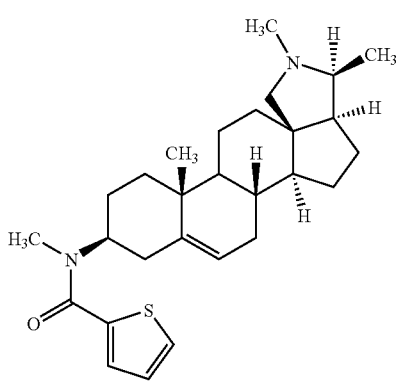

Thiophene-2-carboxylic acid methyl-(2,3,11a-trimethyl-2,3,3a,4,5,5a,5b,6,8,9,10,11, 11a,11b,12,13-hexadecahydro-1H-2-aza-pentaleno[1,6a-a]phenanthren-9-yl)-amide The title compound was prepared according to the procedures described in Reference Example 7C, except substituting 2-thiophene carbonyl chloride for acetyl chloride. $^1$H NMR (CDCl$_3$): δ 0.96 (s, 3 H) 1.23 (m, 4 H) 1.50 (d, J=6.44 Hz, 3 H) 1.79 (m, 7 H) 2.13 (m, 8 H) 2.58 (m, 2 H) 2.83 (d, J=4.07 Hz, 3 H) 3.07 (s, 3 H) 3.32 (m, 1 H) 3.88 (m, 1 H), 4.20 (m, 1 H) 5.37 (d, J=5.09 Hz, 1 H) 7.04 (m, 1 H) 7.31 (m, 1 H) 7.44 (d, J=5.09 Hz, 1 H); MS: $(M+H)^+=453$.

Example 13

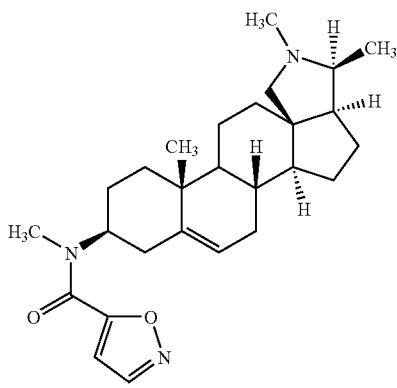

Isoxazole-5-carboxylic acid methyl-(2,3,11a-trimethyl-2,3,3a,4,5,5a,5b,6,8,9,10,11, 11a,11b,12,13-hexadecahydro-1H-2-aza-pentaleno[1,6a-a]phenanthren-9-yl)amide The title compound was prepared according to the procedures described in Reference Example 7C, except substituting isoxazole-5-carbonyl chloride for acetyl chloride. MS: $(M+H)^+=438$.

Example 14

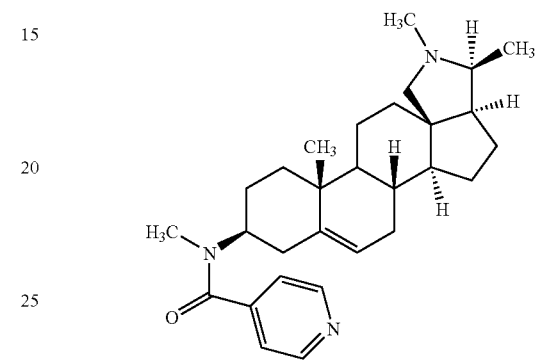

N-Methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-isonicotinamide The title compound was prepared according to the procedures described in Reference Example 7C, except substituting isonicotinoyl chloride hydrochloride for acetyl chloride and using 5 equivalents of triethylamine. $^1$H NMR (CDCl$_3$): δ 0.91 (s, 3 H) 0.96 (s, 3 H) 1.00-2.75 (m, 21 H) 2.80 (m, 3 H) 3.03 (s, 3 H) 3.27 (m, 1 H) 3.71 (m, 1 H) 4.47 (m, 1 H) 5.30 (m, 1 H) 7.39 (d, J=4.07 Hz, 2 H) 8.71 (d, J=4.07 Hz, 2 H); MS: $(M+H)^+=448$ Example 15

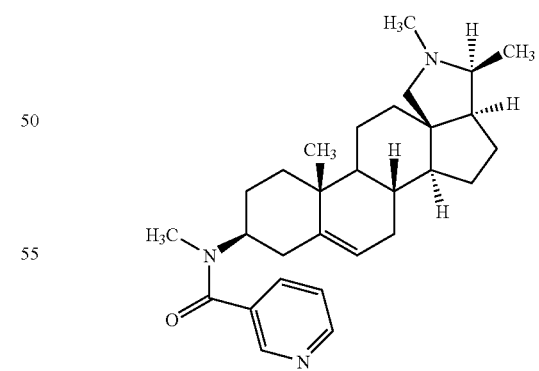

N-Methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-nicotinamide The title compound was prepared according to the procedures described in Reference Example 7C, except substi-

Example 16

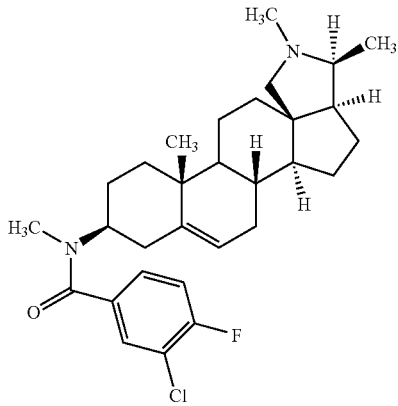

3-Chloro-4-fluoro-N-methyl-N-(2,3,11a-trimethyl-2,3,3a,4,5,5a,5b,6,8,9,10,11,11a, 11b,12,13-hexadecahydro-1H-2-aza-pentaleno[1,6a-a]phen anthren-9-yl)-benzamide The title compound was prepared according to the procedures described in Reference Example 7C, except substituting 3-chloro4-fluorobenzoyl chloride for acetyl chloride. $^1$H NMR (CDCl$_3$): δ 0.92 (s, 3 H) 1.18 (m, 6 H) 1.49 (s, 3 H) 1.82 (m, 7H) 2.15 (m, 7 H) 2.53 (m, 2H) 2.79 (m, 3 H) 2.92 (m, 3 H) 3.36 (m, 1 H) 3.73 (m, 1 H) 5.37 (m, 1 H) 7.15 (m, 2 H) 7.45 (m, 1 H); MS: (M+H)$^+$=499.

Example 17

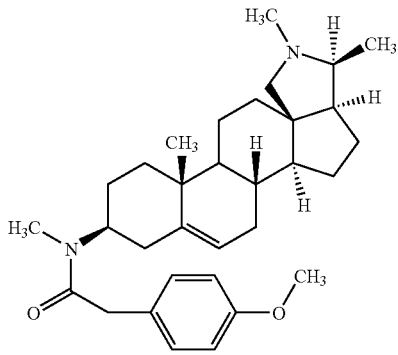

2-(4-Methoxy-phenyl)-N-methyl-N-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-acetamide The title compound was prepared according to the procedures described in Reference Example 7C, except substituting 4-methoxyphenylacetyl chloride for acetyl chloride. MS: (M+H)$^+$=491.

Example 18

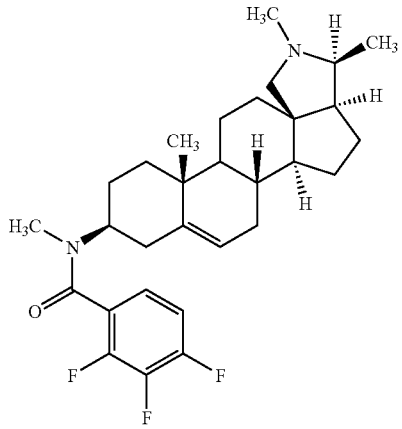

2,3,4-Trifluoro-N-methyl-N-(2,3,11a-trimethyl-2,3,3a,4,5,5a,5b,6,8,9,10,11,11a, 11b,12,1 3-hexadecahydro-1H-2-aza-pentaleno[1,6a-a]phenanthren-9-yl)-benzamide The title compound was prepared according to the procedures described in Reference Example 7C, except substituting 2,3,4-trifluorobenzoyl chloride for acetyl chloride. MS: (M+H)$^+$=491.

Example 19

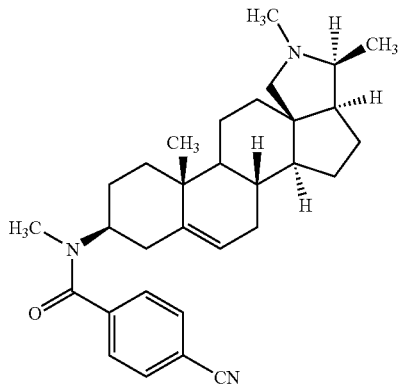

4-Cyano-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide The title compound was prepared according to the procedures described in Reference Example 7C, except substituting 4-cyanobenzoyl chloride for acetyl chloride. $^1$H NMR (CDCl$_3$): δ 0.95 (s, 6 H) 1.00-2.65 (m, 22 H) 2.79 (d, J=4.41 Hz, 6 H) 3.02 (m, 1 H) 3.72 (m, 1 H) 5.33 (m, 1 H) 7.46 (m, 2 H) 7.70 (d, J=8.14 Hz, 2 H); MS: (M+H)$^+$=4.72.

Example 20

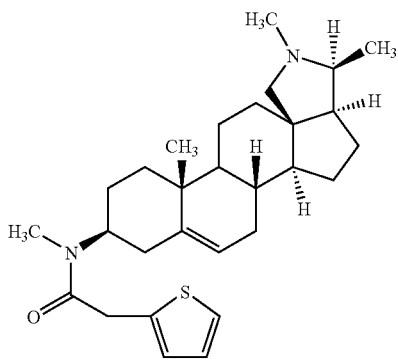

N-Methyl-2-thiophen-2-yl-N-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-acetamide The title compound was prepared according to the procedures described in Reference Example 7C, except substituting 2-thiopheneacetyl chloride for acetyl chloride. $^1$H NMR (CDCl$_3$): δ 0.93 (s, 3 H) 1.04 (d, 3 H) 1.05-2.15 (m, 18 H) 2.20 (s, 3 H) 2.38 (m, 2 H) 2.50 (m, 1 H) 2.90 (d, 3 H) 3.01 (m, 1 H) 3.66 (m, 1 H) 3.90 (d, 2 H) 4.42 (m, 1 H) 5.34 (m, 1 H) 6.87 (m, 1 H) 6.95 (m, 1 H) 7.18 (m, 1 H); MS: (M+H)$^+$=467.

Example 21

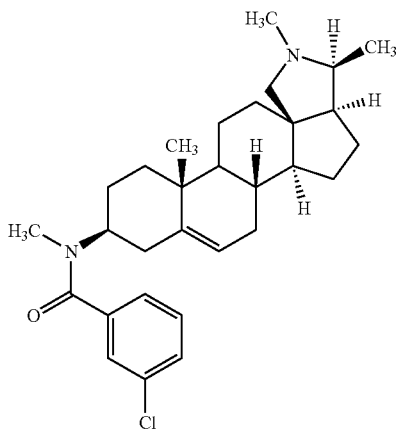

3-Chloro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren9-yl)benzamide The title compound was prepared according to the procedures described in Reference Example 7C, except substituting 3-chlorobenzoyl chloride for acetyl chloride. $^1$H NMR (CDCl$_3$): δ 0.93 (s, 3 H) 1.00-2.65 (m, 23 H) 2.80 (d, J=4.75 Hz, 6 H) 3.00 (m, 2 H) 3.35 (m, 1 H) 3.72 (m, 1 H) 5.30 (m, 1 H) 7.28 (m, 1 H) 7.36 (m, 3 H); MS: (M+H)$^+$=481.

Example 22

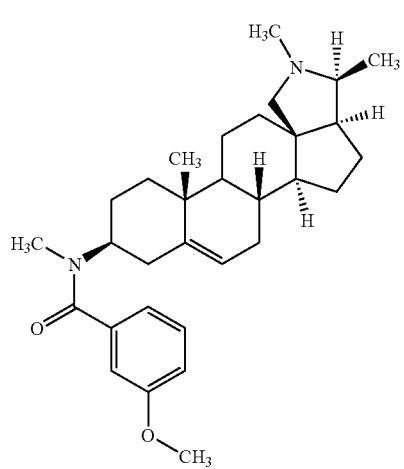

3-Methoxy-N-methyl-N-(2,3,11a-trimethyl-2,3,3a,4,5,5a,5b,6,8,9,10,11,11a,11b,12,13-hexadecahydro-1H-2-aza-pentalen[1,6a-a]phenanthren-9-yl)benzamide The title compound was prepared according to the procedures described in Reference Example 7C, except substituting m-anisoyl chloride for acetyl chloride.

MS: (M+H)$^+$=477.

Example 23

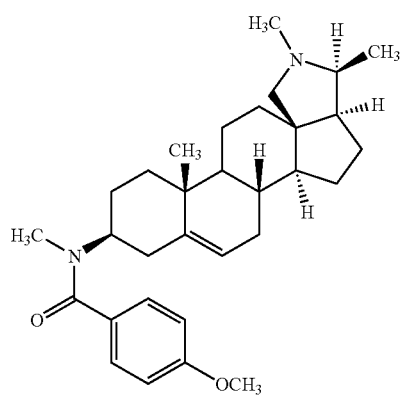

4-Methoxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl )-benzamide The title compound was prepared according to the procedures described in Reference Example 7C, except substituting p-anisoyl chloride for acetyl chloride. MS: (M+H)$^+$=477.

Example 24

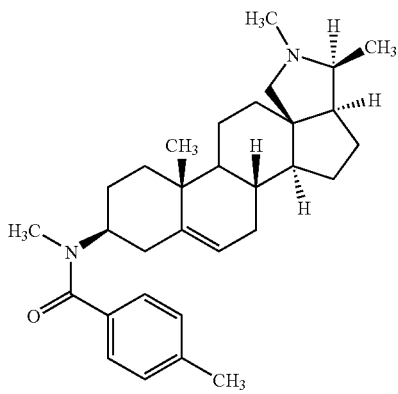

4, N-Dimethyl-N-(2,3,11a-trimethyl-2,3,3a,4,5,5a, 5b,6,8,9,10,11,11a,11b,12,13-hexadecahydro-1H-2-aza-pentaleno[1,6a-a]phenanthren-9-yl)-benzamide The title compound was prepared according to the procedures described in Reference Example 7C, except substituting p-toluoyl chloride for acetyl chloride. $^1$H NMR (CDCl$_3$): δ 0.93 (s, 3 H) 1.00-2.30 (m, 21 H) 2.37 (s, 3 H) 2.54 (m, 2 H) 2.79 (s, 3 H) 2.80 (s, 3 H) 2.95 (m, 2 H) 3.31 (m, 1 H) 3.72 (m, 1 H) 5.30 (m, 1 H) 7.18 (d, J=7.80 Hz, 2 H) 7.27 (d, J=7.80 Hz, 2 H); MS: (M+H)$^+$=461.

Example 25

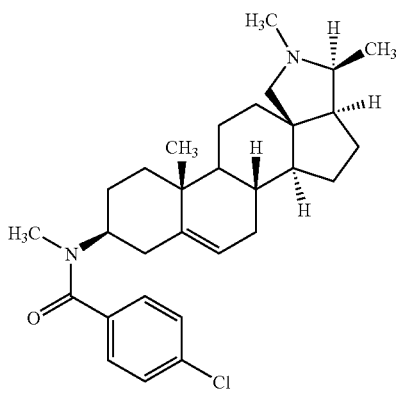

4-Chloro-N-methyl-N-(2,3,11a-trimethyl-2,3,3a,4,5, 5a,5b,6,8,9,10,11,11a,11b,12,13-hexadecahydro-1H-2-aza-pentaleno[1,6a-a]phenanthren-9-yl)benzamide The title compound was prepared according to the procedures described in Reference Example 7C, except substituting 4-chlorobenzoyl chloride for acetyl chloride. $^1$H NMR (CDCl$_3$): δ 0.93 (s, 3 H) 1.00-2.60 (m, 23 H) 2.79 (s, 3 H) 2.80 (s, 3 H) 2.96 (m, 2 H) 3.30 (m, 1 H) 3.73 (m, 1 H) 5.30 (m, 1 H) 7.36 (m, 4 H); MS: (M+H)=482.

Example 26

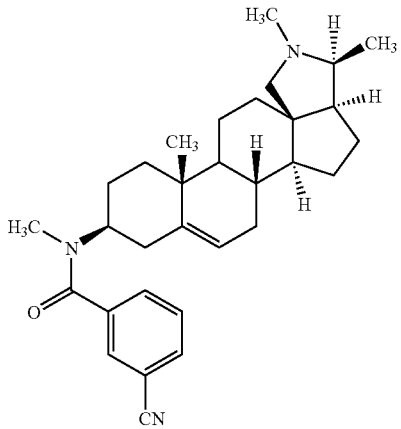

3-Cyano-N-methyl-N-(2,3,11a-trimethyl-2,3,3a,4,5, 5a,5b,6,8,9,10,11,11a,11b,12,13-hexadecahydro-1H-2-aza-pentaleno[1,6a-a]phenanthren9-yl)-benzamide The title compound was prepared according to the procedures described in Reference Example 7C, except substituting 3-cyanobenzoyl chloride for acetyl chloride. $^1$H NMR (CDCl$_3$): δ 0.95 (s, 6 H) 1.00-2.60 (m, 20 H) 2.84 (s, 3 H) 3.02 (s, 3 H) 3.49 (m, 3 H) 4.46 (m, 1 H) 5.41 (m, 1 H) 7.53 (t, J=7.97 Hz, 1 H) 7.68 (m, 3 H); MS: (M+H)$^+$=471.

Example 27

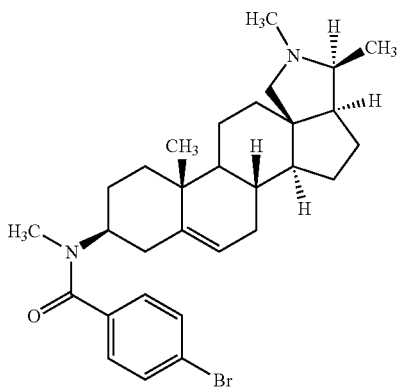

4-Bromo-N-methyl-N-(2,3,11a-trimethyl-2,3,3a,4,5, 5a,5b,6,8,9,10,11,11a,11b,12,13-hexadecahydro-1H-2-aza-pentaleno[1,6a-a]phenanthren-9-yl)-benzamide The title compound was prepared according to the procedures described in Reference Example 7C, except substituting 4-bromobenzoyl chloride for acetyl chloride. $^1$H NMR (CDCl$_3$): δ 0.93 (s, 3 H) 1.00-2.60 (m, 23 H) 2.79 (s, 3 H) 2.99 (s, 3 H) 3.35 (m, 2 H) 3.72 (m, 1 H) 4.44 (m, 1 H) 5.30 (m, 1 H) 7.23 (d, J=8.48 Hz, 2 H) 7.53 (d, J=8.48 Hz, 2 H); MS: (M+H)$^+$=527.

Example 28

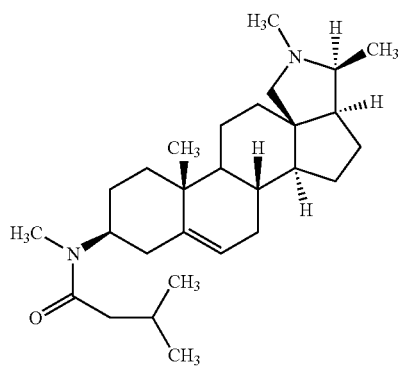

3, N-Dimethyl-N-(2,3,11a-trimethyl-2,3,3a,4,5,5a, 5b,6,8,9,10,11,11a,11b,12,13-hexadecahydro-1H-2-aza-pentaleno[1,6a-a]phenanthren-9-yl)-butyramide The title compound was prepared according to the procedures described in Reference Example 7C, except substituting isovaleryl chloride for acetyl chloride $^1$H NMR (CDCl$_3$): δ 0.98 (m, 12 H) 1.00-2.60 (m, 23 H) 2.84 (s, 3 H) 2.87 (s, 3 H) 3.04 (m, 2 H) 3.58 (m, 1 H) 4.43 (m, 1 H) 5.38 (m, 1 H); MS: (M+H)$^+$=427.

Example 29

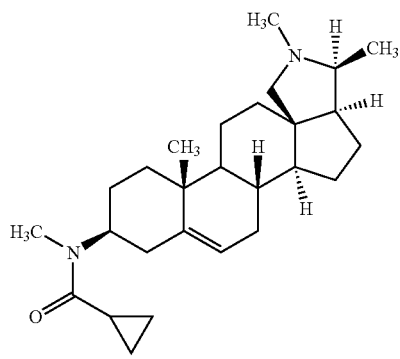

Cyclopropanecarboxylic acid methyl-(2,3,11a-trimethyl-2,3,3a,4,5,5a,5b,6,8,9,10, 11,11a,11b,12,13-hexadecahydro-1H-2-aza-pentaleno[1,6a-a]phenanthren-9yl)-amide The title compound was prepared according to the procedures described in Reference Example 7C, except substituting cyclopropane carbonyl chloride for acetyl chloride. $^1$H NMR (CDCl$_3$): δ 0.75 (m, 4 H) 0.96 (s, 3 H) 0.98 (s, 3 H) 1.00-2.60 (m, 23 H) 2.87 (s, 3 H) 3.04 (s, 3 H) 3.94 (m, 1H) 4.40 (m, 1H) 5.38 (m, 1H); MS: (M+H)$^+$=411.

Example 30

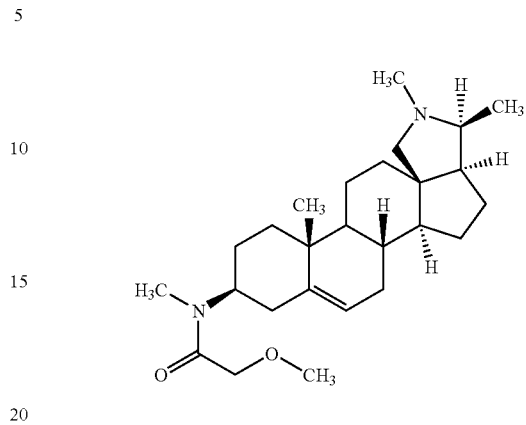

2-Methoxy-N-methyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Reference Example 7C, except substituting methoxyacetyl chloride for acetyl chloride. $^1$H NMR (CDCl$_3$): δ 0.95 (s, 3 H) 1.00-2.60 (m, 28 H) 2.87 (s, 3 H) 3.01 (m, 1 H) 3.43 (s, 3 H) 4.09 (m, 2 H) 4.38 (m, 1 H) 5.36 (m, 1 H); MS: (M+H)$^+$=415.

Example 31

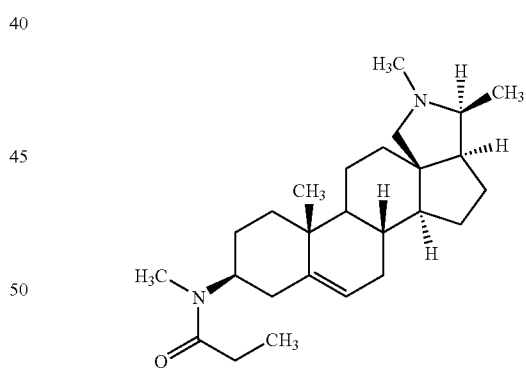

N-Methyl-N-(2,3,11a-trimethyl-2,3,3a,4,5,5a,5b,6,8, 9,10,11,11a,11b,12,13-hexadecahydro-1H-2-aza-pentaleno[1,6a-a]phenanthren-9-yl)-propionamide The title compound was prepared according to the procedures described in Reference Example 7C, except substituting propionyl chloride for acetyl chloride. $^1$H NMR (CDCl$_3$): δ 0.95 (d, J3.73 Hz, 3 H) 1.03 (m, 2 H) 1.14 (t, J=7.46 Hz, 3 H) 1.20-2.60 (m, 28 H) 2.85 (d, J=3.39 Hz, 3 H) 3.54 (m, 1 H) 4.41 (m, 1 H) 5.38 (m, 1 H); MS: (M+H)$^+$=399.

Example 32

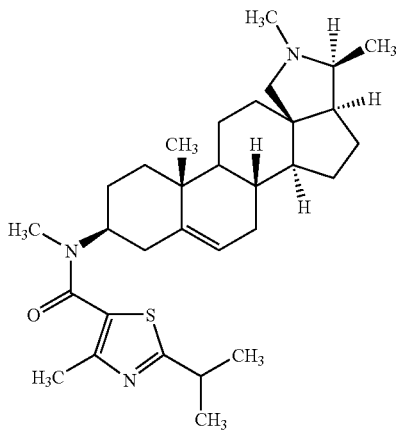

2-Isopropyl-4-methyl-thiazole-5-carboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide A mixture of compound 7B (15 mg, 0.044 mmol), 2-isopropyl-4-methyl-thiazole-5-carboxylic acid (9.0 mg, 0.048 mmol), 1-[3-(dimethylamino)propyl]-3-ethylcarbodiimide hydrochloride (13 mg, 0.066 mmol), 1-hydroxybenzotriazole (9.0 mg, 0.066 mmol) and dichloromethane (1 mL) was stirred at room temperature overnight. The solvent was evaporated under reduced pressure and the residue was dissolved in minimum amount of dichloromethane and purified on silica gel column, which was eluted with 0.5% ammonium hydroxide and 5% methanol in dichloromethane to give the desired product (13 mg, 59% yield). $^1$H NMR (CDCl$_3$): δ 0.96 (s, 3 H) 1.00-1.35 (m, 6 H) 1.38 (d, J=6.78 Hz, 6 H) 1.55-2.35 (m, 21 H) 2.39 (s, 3 H) 2.59 (m, 2 H) 2.95 (s, 3 H) 3.26 (m, 2 H) 5.37 (m, 1 H); MS: (M+H)$^+$=510.

Example 33

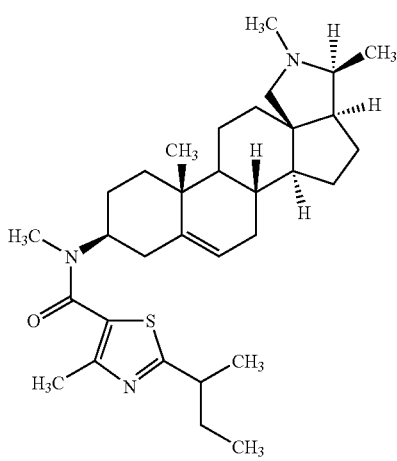

2-sec-Butyl-4-methyl-thiazole-5-carboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 32, except substituting 2-sec-butyl-4-methyl-thiazole-5-carboxylic acid for 2-isopropyl-4-methyl-thiazole-5-carboxylic acid. $^1$H NMR (CDCl$_3$): δ 0.95 (m, 9 H) 1.16 (m, 9 H) 1.39 (d, J=6.78 Hz, 3 H) 1.60-2.60 (m, 21 H) 3.08 (m, 6 H) 5.40 (m, 1 H); MS: (M+H)$^+$=524.

Example 34

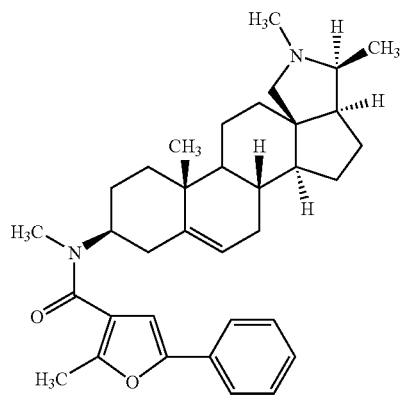

2-Methyl-5-phenyl-furan-3carboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 32, except substituting 2-methyl-5-phenyl-furan-3-carboxylic acid for 2-isopropyl-4-methy-thiazole-5-carboxylic acid. $^1$H NMR (CDCl$_3$): δ 0.97 (s, 3 H) 1.00-2.65 (m, 26 H) 2.44 (s, 3 H) 2.67 (m, 1H) 2.98 (s,3 H) 3.22 (m, 1 H) 3.79 (m, 1 H) 4.45 (m, 1 H) 5.37 (m, 1 H) 7.37 (m, 3 H) 7.62 (m, 3 H); MS: (M+H)$^+$=527.

Example 35

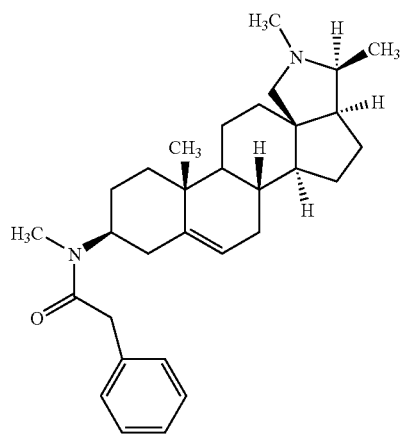

N-Methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 32, except substituting phenylacetic acid for 2isopropyl-4-methyl-thiazole-5-carboxylic acid. MS: (M+H)$^+$=461.

Example 36

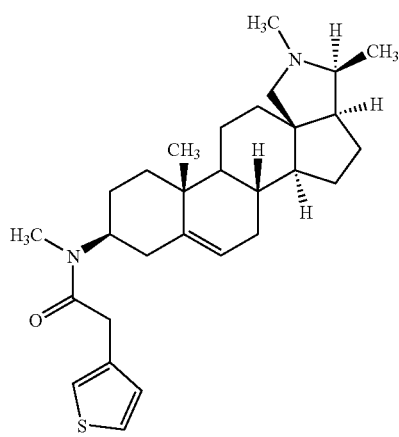

N-Methyl-2-thiophen-3-yl-N-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-acetamide The title compound was prepared according to the procedures described in Example 32, except substituting 3-thiopheneacetic acid for 2-isopropyl-4-methyl-thiazole-5-carboxylic acid. $^1$H NMR (CDCl$_3$): δ 0.92 (s, 3 H) 0.94 (s, 3 H) 1.00-2.60 (m, 19 H) 2.85 (d, J=4.07 Hz, 3 H) 3.05 (m, 1 H) 3.25 (m, 1 H) 3.59 (m, 2 H) 3.72 (d, J=9.49 Hz, 3 H) 4.44 (m, 1 H) 5.28 (m, 2 H) 5.35 (m, 1 H) 7.01 (d, J=4.75 Hz, 1 H) 7.06 (s, 1 H) 7.28 (m, 1 H); MS: (M+H)$^+$=467.

Example 37

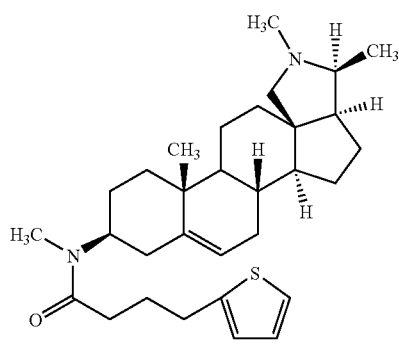

N-Methyl-4-thiophen-2-yl-N-(2,3,11a-trimethyl-2,3,3a,4,5,5a,5b,6,8,9,10,11,11a,11b, 12,13-hexadecahydro-1H-2-aza-pentaleno[1,6a-a]phenanthren-9-yl)-butyramide The title compound was prepared according to the procedures described in Example 32, except substituting 4-(2-thienyl)butyric acid for 2-isopropyl-4-methyl-thiazole-5-carboxylic acid. $^1$H NMR (CDCl$_3$): δ 0.94 (s, 3 H) 1.00-2.60 (m, 29 H) 2.81 (s, 3 H) 2.84 (s, 3 H) 2.91 (t, J=7.29 Hz, 2 H) 3.44 (m, 1 H) 4.38 (m, 1 H) 5.35 (m, 1 H) 6.80 (d, J=3.39 Hz, 1H) 6.92 (m, 1H) 7.11 (d, J=5.09 Hz, 1H); MS: (M+H)$^+$=495.

Example 38

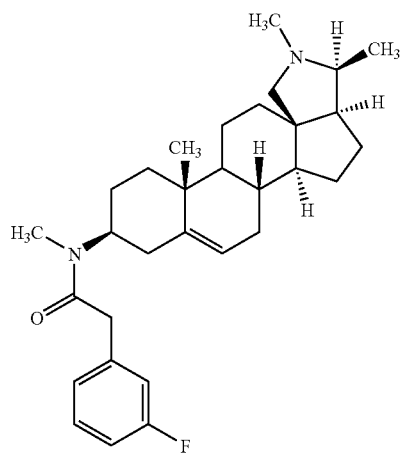

2-(3-Fluoro-phenyl)-N-methyl-N-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-acetamide The title compound was prepared according to the procedures described in Example 32, except substituting 3-fluorophenylacetic acid for 2-isopropyl-4-methyl-thiazole-5carboxylic acid. $^1$H NMR (CDCl$_3$): δ 7.25 (m,1H), 6.95 (m, 3H), 5.30 (m,1H), 4.40 (m,1H), 3.68 (d, 3H), 2.80 (s, 3H), 0.90 d, 3H), 2.70-1.00 (m, 28H); MS: (M+H)$^+$=479.

Example 39

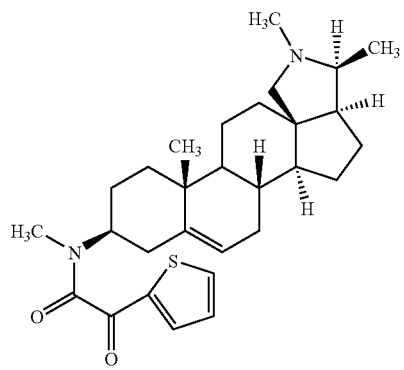

N-Methyl-2-oxo-2-thiophen-2-yl-N-(2,3,11a-trimethyl-2,3,3a,4,5,5a,5b,6,8,9,10,11, 11a,11b,12,13-hexadecahydro-1H-2-aza-pentaleno[1,6a-a]phenanthren-9-yl)-acetamide The title compound was prepared according to the procedures described in Example 32, except substituting 2-thiopheneglyoxylic acid for 2-isopropyl-4-methyl-thiazole-5-carboxylic acid. $^1$H NMR (CDCl$_3$): δ 7.79 (m, 2H), 7.20 (m, 1H), 5.35 (m, 1H), 4.40 (m,1H), 3.02 (s, 3H), 2.90 (s, 3H), 0.93 (d, 3H), 2.60-1.00 (m, 26H); MS: (M+H)$^+$=481.

Example 40

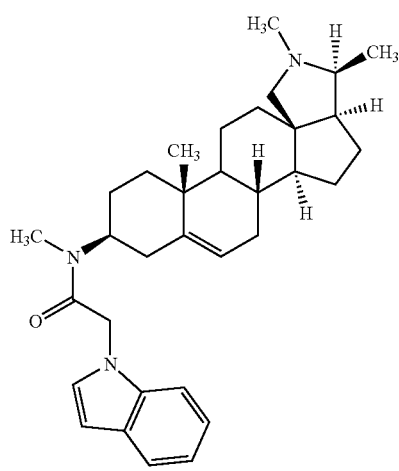

2-Indol-1-yl-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 32, except substituting indoleacetic acid for 2-isopropyl-4-methyl-thiazole-5-carboxylic acid. $^1$H NMR (CDCl$_3$): δ 0.90 (s, 3 H) 0.93 (s, 3 H) 1.00-2.50 (m, 24 H) 2.86 (d, J=2.03 Hz, 3 H) 3.00 (m, 1H) 3.52 (m, 1H) 4.36 (m, 1H) 4.91 (d, J=10.17 Hz, 2 H) 5.30 (m, 1H) 6.56 (s, 1H) 7.11 (m, 2 H) 7.22 (m, 2 H) 7.61 (m, 1 H); MS: (M+H)$^+$=500.

Example 41

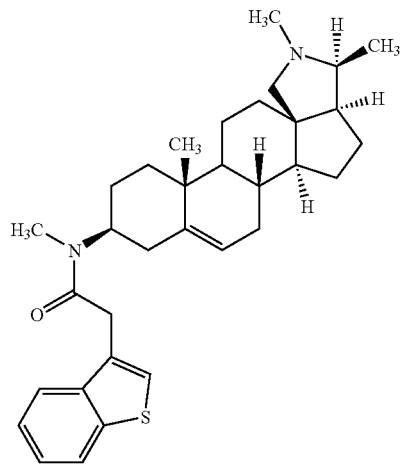

2-Benzo[b]thiophen-3-yl-N-methyl-N-(2,3,11a-trimethyl-2,3,3a,4,5,5a,5b,6,8,9,10,11, 11a,11b,12,13-hexadecahydro-1H-2aza-pentaleno[1,6a-a]phenanthren-9-yl)acetamide The title compound was prepared according to the procedures described in Example 32, except substituting benzo[b]thiophene-3acetic acid for 2-isopropyl-4-methyl-thiazole-5-carboxylic acid. $^1$H NMR (CDCl$_3$): δ 0.88 (s, 3 H) 0.94 (s, 3 H) 1.00-2.50 (m, 22 H) 2.87 (d, J=4.41 Hz, 6 H) 3.64 (m, 1H) 3.92 (d, J=12.54 Hz, 2 H) 4.49 (m, 1 H) 5.30 (m, 1 H) 7.22 (m, 1 H) 7.38 (m, 2 H) 7.85 (m, 2 H); MS: (M+H)$^+$=517.

Example 42

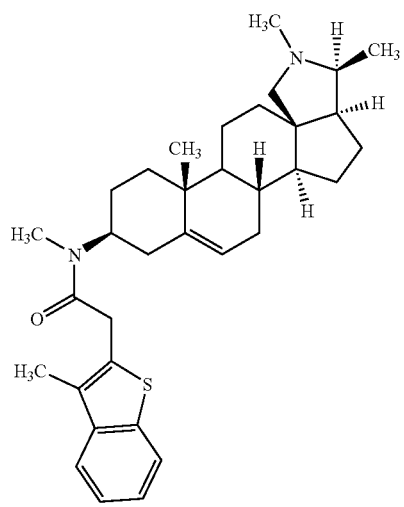

N-Methyl-2-(3-methyl-benzo[b]thiophen-2-yl)-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 32, except substituting 3-methylbenzo[b]thiopheneacetic acid for 2isopropyl-4-methyl-thiazole-5-carboxylic acid. $^1$H NMR (CDCl$_3$): δ 0.92 (d, J=8.14 Hz, 3 H) 1.00-2.50 (m, 25 H) 2.36 (d, J=6.44 Hz, 3 H) 2.86 (s, 3 H) 2.93 (s, 3 H) 3.65 (m, 1 H) 3.94 (m, 2 H) 4.37 (m, 1H) 5.30 (m, 1H) 7.32 (m, 2 H) 7.62 (m, 1H) 7.74 (m, 1H); MS: (M+H$^+$531.

Example 43

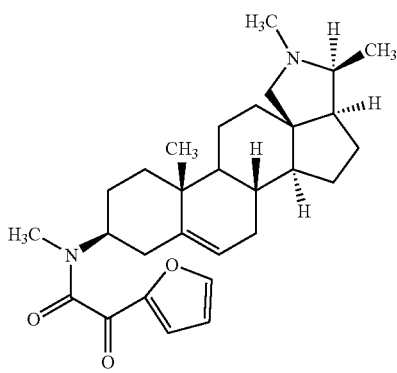

2-Furan-2-yl-N-methyl-2-oxo-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 32, except substituting 2-oxo-2-furanacetic acid for 2-isopropyl-4-methyl-thiazole-5-carboxylic acid. $^1$H NMR (CDCl$_3$): δ 0.95 (d, J=1 1.87 Hz, 3 H) 1.00-2.60 (m, 26 H) 2.91 (s, 3 H) 3.00 (s, 3 H) 4.38 (m, 1 H) 5.30 (m, 1 H) 6.60 (dd, J=3.73, 1.70 Hz, 1 H) 7.33 (t, J=3.39 Hz, 1H) 7.71 (s, 1H); MS: (M+H)$^+$=465.

Example 44

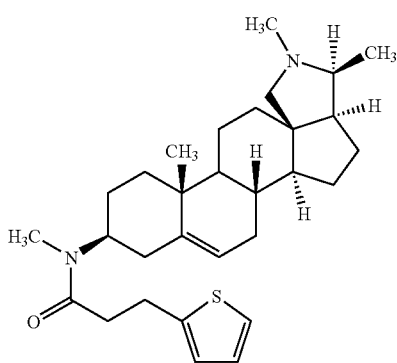

N-Methyl-3-thiophen-2-yl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 32, except substituting 3-(2-thienyl)propanoic acid for 2-isopropyl-4-methyl-thiazole-5-carboxylic acid. $^1$H NMR (CDCl$_3$): δ 0.94 (s, 3 H) 1.00-2.60 (m, 25 H) 2.66 (m, 2 H) 2.83 (s, 3 H) 2.86 (s, 3 H) 3.20 (m, 2 H) 3.53 (m, 1 H) 4.40 (m, 1 H) 5.34 (m, 1 H) 6.83 (d, J=3.39 Hz, 1 H) 6.92 (m, 1 H) 7.12 (d, J=5.42 Hz, 1 H); MS: (M+H)$^+$=481.

Example 45

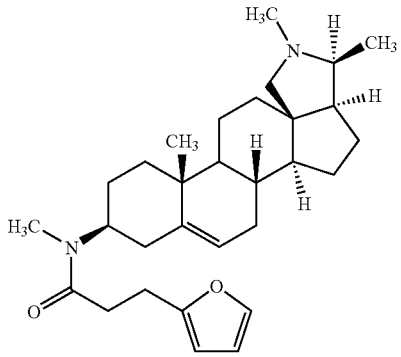

3-Furan-2-yl-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)propionamide The title compound was prepared according to the procedures described in Example 32, except substituting (2-furyl)propanoic acid for 2-isopropyl4-methyl-thiazole-5-carboxylic acid. $^1$H NMR (CDCl$_3$): δ 0.95 (s,3 H) 1.00-2.55 (m, 25 H) 2.64 (m, 2 H) 2.83 (s, 3 H) 2.86 (s, 3 H) 3.00 (m, 2 H) 3.54 (m, 1 H) 4.40 (m, 1 H) 5.35 (m, 1 H) 6.03 (t, J=2.88 Hz, 1 H) 6.28 (dd, 3.22, 1.86 Hz, 1 H) 7.30 (s, 1 H); MS: (M+H)$^+$=465.

Example 46

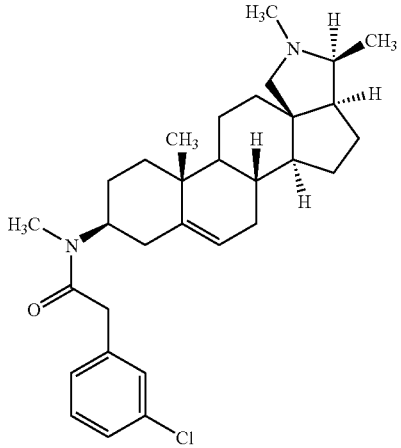

2-(3-Chloro-phenyl-N-methyl-N-(2,3,11a-trimethyl-
2,3,3a,4,5,5a,5b,6,8,9,10,11,11a, 11b,12,13-hexa-
decahydro-1H-2-aza-pentaleno[1,6a-a]phenanthren-
9-yl)-acetamide The title compound was prepared according to the procedures described in Example 32, except substituting 3-chlorophenylacetic acid for 2-isopropyl-4-methyl-thiazole-5carboxylic acid. MS: (M+H)$^+$=495/497.

Example 47

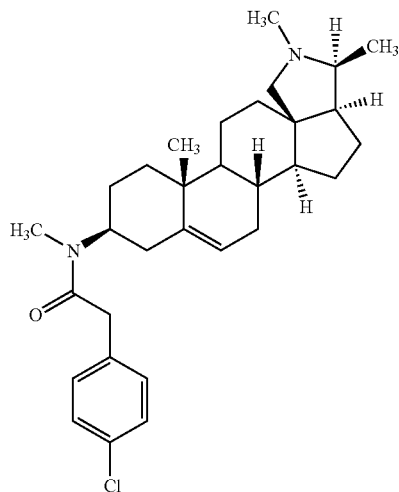

2-(4-Chloro-phenyl)-N-methyl-N-(2,3,11a-trimethyl-
2,3,3a,4,5,5a,5b,6,8,9,10,11,11a, 11b,12,13-hexa-
decahydro-1H-2-aza-pentaleno[1,6a-a]phenanthren-
9-yl)-acetamide The title compound was prepared according to the procedures described in Example 32, except substituting 4-chlorophenylacetic acid for 2-isopropyl-4-methyl-thiazole-5-carboxylic acid. MS: (M+H)$^+$=495/497.

Example 48

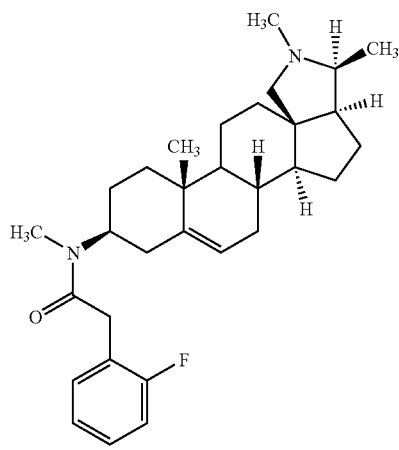

2-(2-Fluoro-phenyl)-N-methyl-N-(2,3,11a-trimethyl-
2,3,3a,4,5,5a,5b,6,8,9,10,11,11a, 11b,12,13-hexa-
decahydro-1H-2-aza-pentaleno[1,6a-a]phenanthren-
9-yl)-acetamide The title compound was prepared according to the procedures described in Example 32, except substituting 2-fluorophenylacetic acid for 2-isopropyl-4-methyl-thiazole-5carboxylic acid. MS: (M+H)$^+$=479.

Example 49

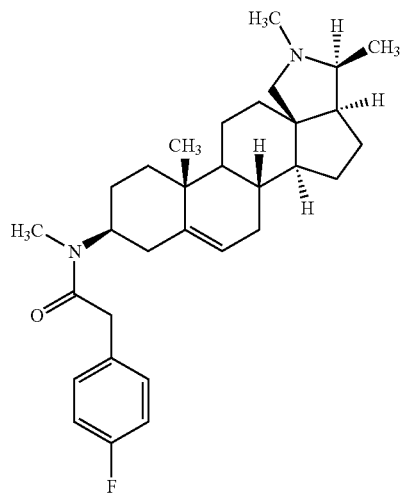

2-(4-Fluoro-phenyl)-N-methyl-N-(2,3,11a-trimethyl-
2,3,3a,4,5,5a,5b,6,8,9,10,11,11a, 11b,12,13 hexa-
decahydro-1H-2-aza-pentaleno[1,6a-a]phenanthren-
9-yl)-acetamide The title compound was prepared according to the procedures described in Example 32, except substituting 4-fluorophenylacetic acid for 2isopropyl-4-methyl-thiazole-5-carboxylic acid. MS: (M+H)$^+$=479.

Example 50

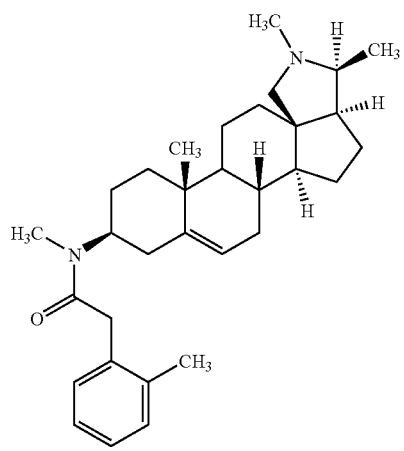

N-Methyl-2-o-tolyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren9-yl)acetamide The title compound was prepared according to the procedures described in Example 32, except substituting o-tolylacetic acid for 2-isopropyl-4-methyl-thiazole-5-carboxylic acid. MS: (M+H)$^+$=475.

Example 51

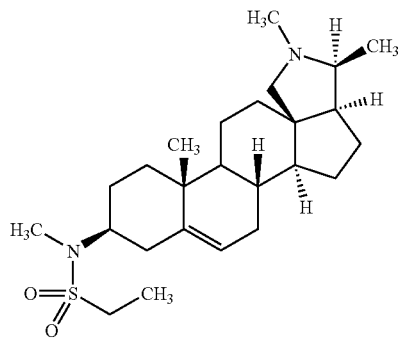

Ethanesulfonic acid methyl-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-amide A mixture of compound 7B (15 mg, 0.044 mmol), ethanesulfonyl chloride (5 μL, 1.5 eq), triethylamine (15 μL, 3.0 eq) and dichloromethane (1 mL) was stirred at room temperature overnight. The clear solution was directly loaded on silica gel column and eluted with 0.5% ammonium hydroxide and 5% methanol in dichloromethane to give the desired product (12.5 mg, 82% yield)

$^1$H NMR (CDCl$_3$): δ 5.35 (m, 1H), 3.37 (m, 1H), 2.95 (q, 2H), 2.85 (s, 3H), 2.80 (d, 3H), 1.35 (t, 3H), 0.90 (s, 3H), 2.60-1.00 (m, 20H). MS (DCI): (M+H)$^+$=435, (M+NH$_4$)$^+$=452

Example 52

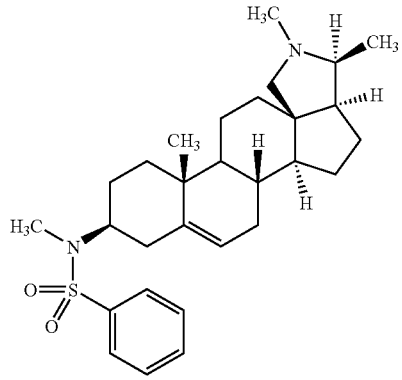

N-Methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzenesulfonamide The title compound was prepared according to the procedures described in Example 51, except substituting benzenesulfonyl chloride for ethanesulfonyl chloride. $^1$H NMR (CDCl$_3$): δ 0.85 (s, 3 H) 0.95 (m, 1 H) 1.03 (d, 3 H) 1.10-1.45 (m, 9 H) 1.50-1.90 (m, 9 H) 2.03 (m, 1 H) 2.18 (s, 3 H) 2.34 (m, 2 H) 2.78 (s, 3 H) 2.95 (m (m, 1H) 5.22 (m, 1H) 7.48 (m, 2 H) 7.57 (m, 1H) 7.81 (m, 2 H); MS: (M+H)$^+$=483, (M+NH$_4$)$^+$=500.

Example 53

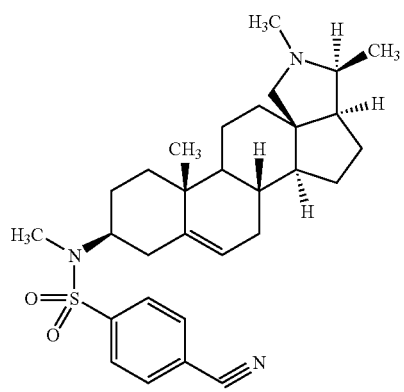

4-Cyano-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)benzenesulfonamide The title compound was prepared according to the procedures described in Example 51, except substituting 4-cyanobenzenesulfonyl chloride for ethanesulfonyl chloride. $^1$H NMR (CDCl$_3$): δ 0.88 (s, 3 H) 1.00-2.40 (m, 28 H) 2.81 (s, 3 H) 2.99 (m, 1 H) 3.75 (m, 1 H) 5.25 (m, 1 H) 7.80 (m, 2 H) 7.93 (m, 2 H); MS: (M+H)$^+$=508.

Example 54

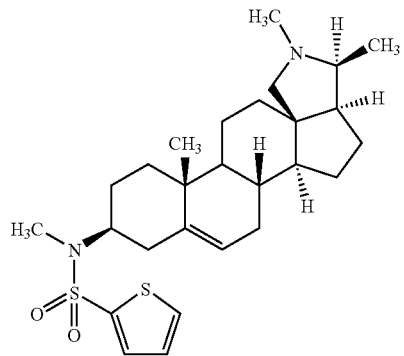

Thiophene-2-sulfonic acid methyl-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-amide The title compound was prepared according to the procedures described in Example 51, except substituting thiophene-2-sulfonyl chloride for ethanesulfonyl chloride. $^1$H NMR (CDCl$_3$): δ 0.88 (s, 3 H) 1.00-2.40 (m, 29 H) 2.82 (s, 3 H) 3.77 (m, 1 H) 5.24 (m, 1 H) 7.09 (m, 1H) 7.55 (m, 2 H); MS: (M+H)$^+$=489.

Example 55

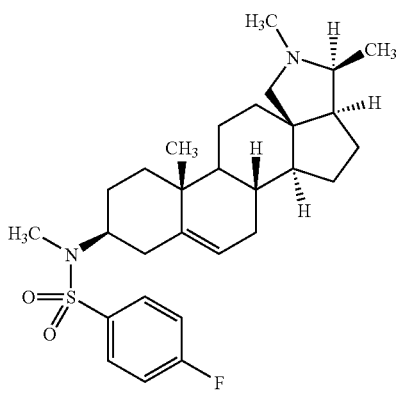

4-Fluoro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzenesulfonamide The title compound was prepared according to the procedures described in Example 51, except substituting 4-fluorobenzenesulfonyl chloride for ethanesulfonyl chloride. $^1$H NMR (CDCl$_3$): δ 0.88 (s, 3 H) 1.00-2.40 (m, 28 H) 2.80 (s, 3 H) 2.99 (m, 1 H) 3.73 (m, 1 H) 5.23 (m, 1 H) 7.50 (m, 2 H) 7.61 (m, 2 H); MS: (M+H)$^+$=501.

Example 56

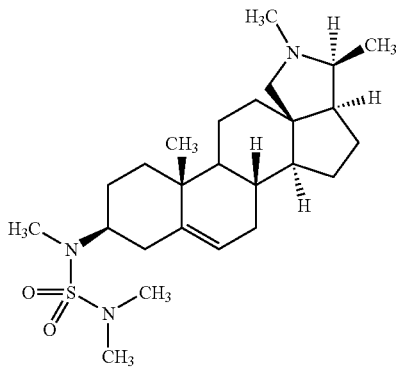

1,1-Dimethyl-3-methyl-3-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-sulfamide The title compound was prepared according to the procedures described in Example 51, except substituting dimethylsulfomoyl chloride for ethanesulfonyl chloride. $^1$H NMR (CDCl$_3$): δ 0.93 (s, 3 H) 1.00-2.50 (m, 25 H) 2.77 (m, 12 H) 2.98 (m, 1 H) 3.56 (m, 1H) 5.38 (m, 1H); MS: (M+H)$^+$=450.

Example 57

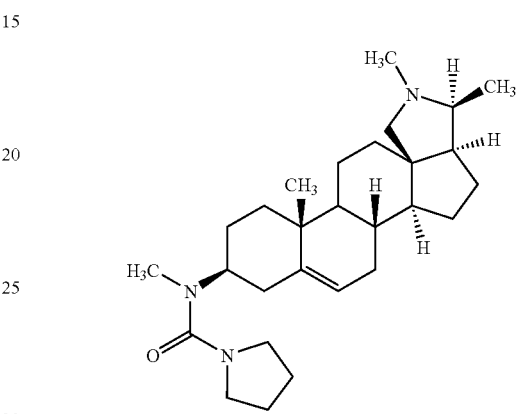

Pyrrolidine-1-carboxylic acid methyl-(2,3,11a-trimethyl-2,3,3a,4,5,5a,5b,6,8,9,10,11, 11a,11b,12,13-hexadecahydro-1H-2-aza-pentaleno[1,6a-a]phenanthren-9-yl)-amide A mixture of compound 7B (10.7 mg, 0.031 mmol), 1-pyrrolidinecarbonyl chloride (13 μL, 3.0 eq), triethylamine (26 μL, 6.0 eq) and dichloromethane (1 mL) was stirred at room temperature overnight. The clear solution was directly loaded on silica gel column and eluted with 0.5% ammonium hydroxide and 5% methanol in dichloromethane to give the desired product (12 mg, 87% yield).
$^1$H NMR (CDCl$_3$): δ 5.30 (m, 1H), 3.65 (m, 2H), 3.30(m, 4H), 2.70 (s, 3H), 0.90 (s, 3H), 2.85-1.00 (m, 32H). MS: (M+H)$^+$=440

Example 58

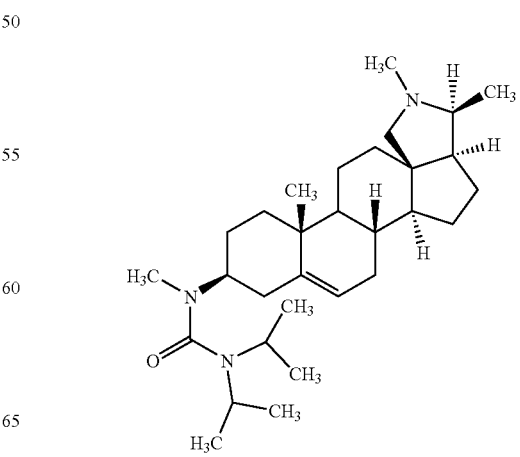

1,1-Diisopropyl-3-methyl-3-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-urea The title compound was prepared according to the procedures described in Example 57, except substituting diisopropylcarbamyl chloride for 1-pyrrolidinecarbonyl chloride. $^1$H NMR (CDCl$_3$): δ 0.91 (s, 3 H) 0.98 (m, 2 H) 1.26 (d, 12 H) 1.30-260 (m, 22 H) 2.64 (s, 3 H) 2.80 (d, J=4.75 Hz, 3 H) 3.37 (m, 2 H) 3.55 (m, 2 H) 3.72 (m, 1) 5.33 (m, 1 H); MS: (M+H)$^+$=470.

Example 59

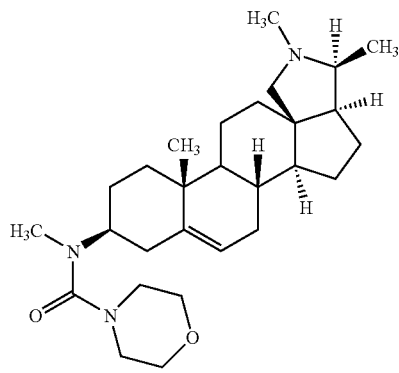

Morpholine-4carboxylic acid methyl-(2,3,11a-trimethyl-2,3,3a,4,5,5a,5b,6,8,9,10, 11,11a,11b,12,13-hexadecahydro-1H-2-aza-pentaleno[1,6a-a]phenanthren-9yl)-amide The title compound was prepared according to the procedures described in Example 57, except substituting 4-morpholinecarbonyl chloride for 1-pyrrolidinecarbonyl chloride. $^1$H NMR (CDCl$_3$): δ 0.95 (s, 3 H) 1.00-2.50 (m, 28 H) 2.77 (s, 3 H) 2.97 (m, 1 H) 3.20 (m, 4 H) 3.55 (m, 1 H) 3.69 (m, 4 H) 5.36 (m, 1 H); MS: (M+H)$^+$=456.

Example 60

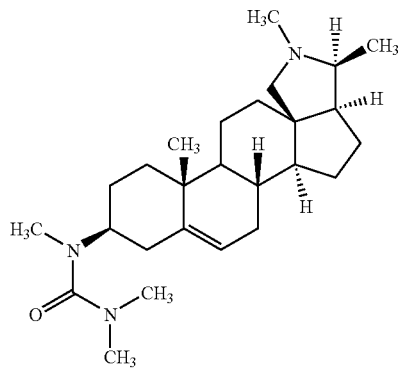

1,1,3-Trimethyl-3-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-urea The title compound was prepared according to the procedures described in Example 57, except substituting dimethylcarbamyl chloride for 1-pyrrolidinecarbonyl chloride. $^1$H NMR (CDCl$_3$): δ 0.95 (s, 3 H) 1.00-2.50 (m, 28 H) 2.72 (s, 3 H) 2.78 (s, 6 H) 2.98 (m, 1 H) 3.47 (m, 1 H) 5.35 (m, 1 H); MS: (M+H)$^+$=414.

Example 61

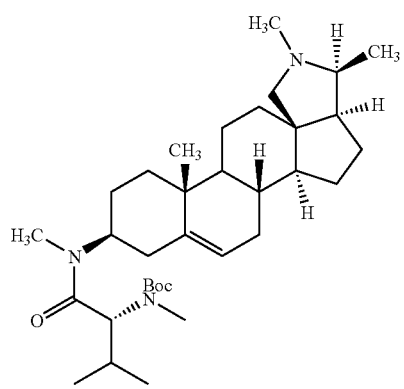

Methyl-{2-methyl-1-[methyl-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-carbamoyl]-propyl}-carbamic acid tert-butyl ester A mixture of compound 7B (240 mg, 0.702 mmol), Boc-N-methyl-D-valine (176 mg, 0.762 mmol), 1-[3-(dimethylamino)propyl]-3-ethylcarbodiimide hydrochloride (208 mg, 1.085 mmol), 1-hydroxybenzotriazole (146 mg, 1.085 mmol), dichloromethane (5 mL) and THF (2.5 mL) was stirred at room temperature overnight. The solvent was evaporated under reduced pressure and the residue was dissolved in minimum amount of dichloromethane and purified on silica gel column, which was eluted with 0.5% ammonium hydroxide and 5% methanol in dichloromethane to give the desired product (282 mg, 72% yield).

$^1$H NMR (CDCl$_3$): δ 0.89 (m, 12 H) 1.00-1.40 (m, 11 H) 1.46 (m, 9 H) 1.50-2.60 (m, 12 H) 2.74 (d, 3 H) 2.85 (d, 3 H) 2.94 (d, 3 H) 3.91 (m, 1 H) 4.34 (m, 1 H) 4.65 (m, 1 H) 5.38 (m,1 H). MS: (M+H)$^+$=556.

Example 62

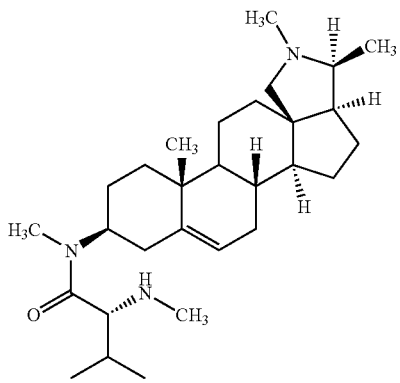

3, N-Dimethyl-2-methylamino-N-(2,3,11a-trimethyl-2,3,3a,4,5,5a,5b,6,8,9,10,11,11a, 11b,12,13-hexadecahydro-1H-2-aza-pentaleno[1,6a-a]phenanthren-9-yl)-butyramide Compound 61 (250 mg, 0.45 mmol) was stirred with a mixture of trifluoroacetic acid and dichloromethane (5 mL/5 mL) for 3 hours. Solvent was removed under reduced pressure, and the residue was triturated with dichloromethane 3×. The residue was then dissolved in ethyl acetate, stirred with sodium bicarbonate powder for 5 min and filtered. The filtrate was concentrated and purified on silica gel column, which was eluted with 0.5% ammonium hydroxide and 5% methand in dichloromethane to give the desired product (202 mg, 98% yield).

$^1$H NMR (CDCl$_3$): δ 0.95 (m, 12 H) 1.00-2.20 (m, 19 H) 2.25 (s, 3 H) 2.29 (s, 3H) 2.40-2.80 (m, 3 H) 2.91 (d, 3 H) 3.05 (m, 3 H) 3.65 (m, 1 H) 4.48 (m, 1 H) 5.38 (m, 1 H). MS: (M+H)$^+$=456.

Example 63

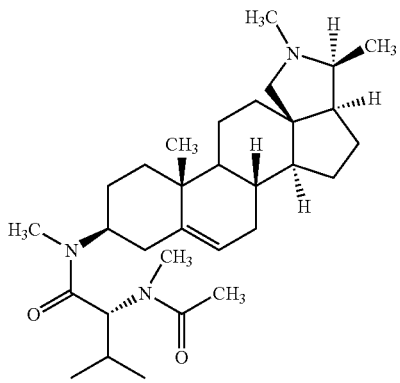

2-(Acetyl-methyl-amino)-3, N-dimethyl-N-(2,3,11a-trimethyl-2,3,3a,4,5,5a,5b,6,8,9,10, 11,11a,11b,12, 13-hexadecahydro-1H-2-aza-pentaleno[1,6a-a] phenanthren-9yl)-butyramide Compound 62 (11 mg, 0.024 mmol) was dissolved in 1 mL dichloromethane. Then triethylamine (20 µL, 6 eq) was added, followed by acetyl chloride (5.2 µL, 3 eq). The mixture was stirred at room temperature overnight. The crude mixture was purified on silica gel column which was eluted with 0.3%ammonium hydroxide and 3% methanol in dichloromethane to give the desired product (6 mg, 50% yield).

MS: (M+H)$^+$=498.

Example 64

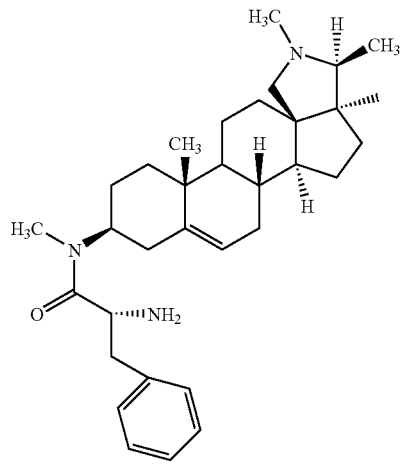

2-Amino-N-methyl-3-phenyl-N-(2,3,3a,11a-tetramethyl-2,3,3a,4,5,5a,5b,6,8,9,10, 11,11a,11b,12,13-hexadecahydro-1H-2-aza-pentaleno[1,6a-a]phenanthren-9-yl)-propionamide The title compound was prepared according to the procedures described in Example 61, except substituting Boc-D-phenylalanine for Boc-N-Methyl-D-Valine and removing the BOC group as described in Example 62. MS: (M+H)$^+$=490.

Example 65

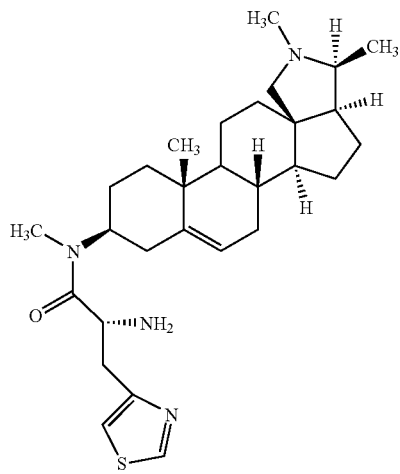

2-Amino-N-methyl-3-thiazol-4-yl-N-(2,3,11a-trimethyl-2,3,3a,4,5,5a,5b,6,8,9,10, 11,11a,11b,12,13-hexadecahydro-1H-2-aza-pentaleno[1,6a-a]phenanthren-9-yl)-propionamide The title compound was prepared according to the procedures described in Example 61, except substituting Boc-D-4-thiazolylalanine for Boc-N-methyl-D-valine and removing the BOC group as described in Example 62. MS: $(M+H)^+=497$.

Example 66

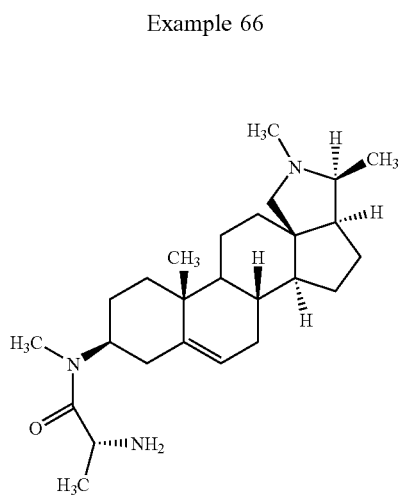

2-Amino-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)propionamide The title compound was prepared according to the procedures described in Example 61, except substituting Boc-D-alanine for Boc-N-methyl-D-valine and removing the BOC group as described in Example 62. MS: $(M+H)^+=414$.

Example 67

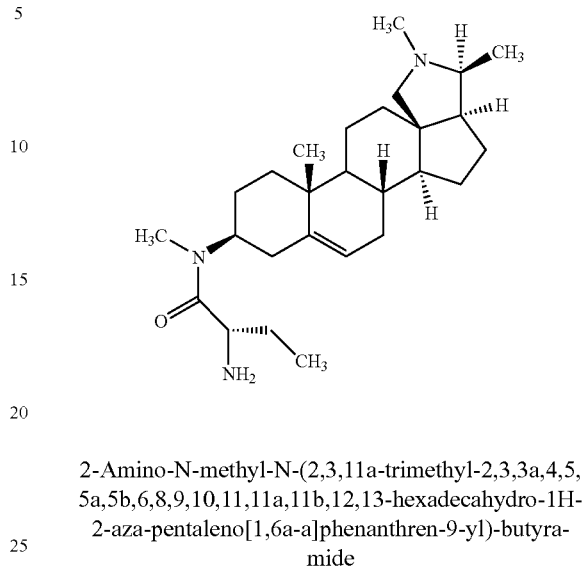

2-Amino-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 61, except substituting Boc-D-ethylglycine for Boc-N-methyl-D-valine and removing the BOC group as described in Example 62. MS: $(M+H)^+=428$.

Example 68

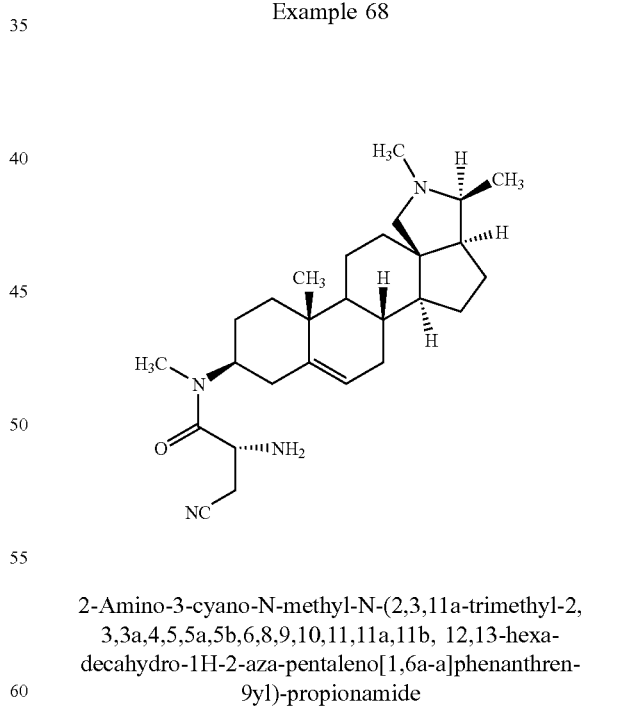

2-Amino-3-cyano-N-methyl-N-(2,3,11a-trimethyl-2,3,3a,4,5,5a,5b,6,8,9,10,11,11a,11b, 12,13-hexadecahydro-1H-2-aza-pentaleno[1,6a-a]phenanthren-9yl)-propionamide The title compound was prepared according to the procedures described in Example 61, except substituting Boc-β-cyano-D-alanine for Boc-N-methyl-D-valine and removing the BOC group as described in Example 62. MS: $(M+H)^+=439$.

Example 69

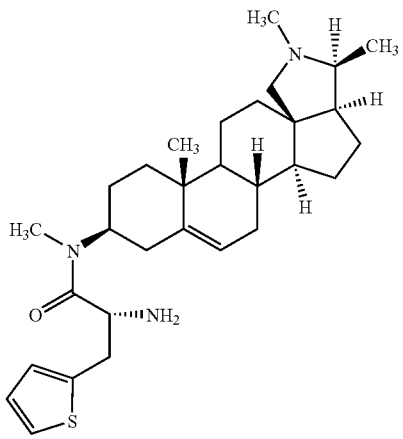

2-Amino-N-methyl-3-thiophen-2-yl-N-(2,3,11a-trimethyl-2,3,3a,4,5,5a,5b,6,8,9,10,11, 11a,11b,12, 13-hexadecahydro-1H-2-aza-pentaleno[1,6a-a]phenanthren-9-yl)-propionamide The title compound was prepared according to the procedures described in Example 61, except substituting Boc-β-(2-thienyl-D-alanine for Boc-N-methyl-D-valine and removing the BOC group as described in Example 62. MS: $(M+H)^+=496$.

Example 70

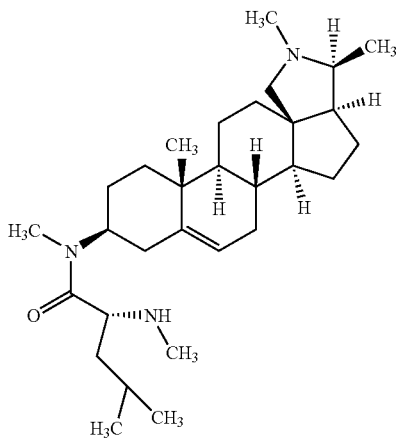

4-Methyl-2-methylamino-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 61, except substituting Boc-N-methyl-D-leucine for Boc-N-methyl-D-valine and removing the BOC group as described in Example 62. $^1$H NMR (CDCl$_3$):δ 0.95 (m, 6 H) 1.00-2.90 (m, 38 H) 2.96 (s, 3 H) 3.37 (m, 1 H) 3.90 (m, 1 H) 4.25 (m, 1 H) 5.39 (m, 1 H); MS: $(M+H)^+=470$.

Example 71

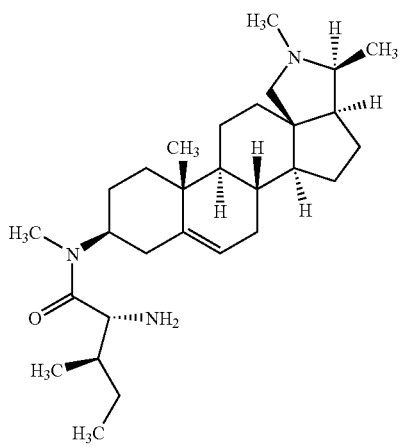

2-Amino-3-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 61, except substituting Boc-D-isoleucine for Boc-N-methyl-D-valine and removing the BOC group as described in Example 62. $^1$H NMR (CDCl$_3$):δ 0.80-2.85 (m, 38 H) 2.86 (s, 3 H) 2.91 (s, 3 H) 2.99 (m, 1 H) 3.46 (m, 1 H) 3.58 (m, 1 H), 4.42 (m, 1 H) 5.37 (m, 1 H); MS: $(M+H)^+=456$.

Example 72

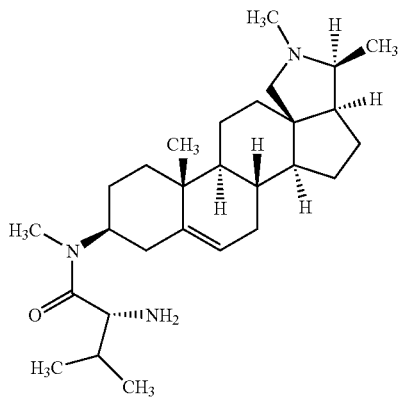

2-Amino-3, N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 61, except substituting Boc-D-valine for Boc-N-methyl-D-valine and removing the BOC group as described in Example 62. MS: $(M+H)^+=442$.

Example 73

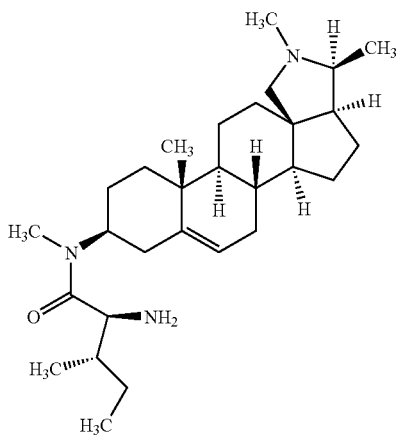

2-Amino-3-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 61, except substituting Boc-L-isoleucine for Boc-N-methyl-D-valine and removing the BOC group as described in Example 62. MS: $(M+H)^+=456$.

Example 74

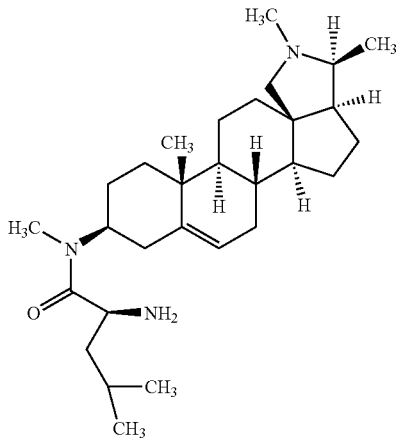

2-Amino-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 61, except substituting Boc-L-leucine for Boc-N-methyl-D-valine and removing the BOC group as described in Example 62. MS: $(M+H)^+=456$.

Example 75

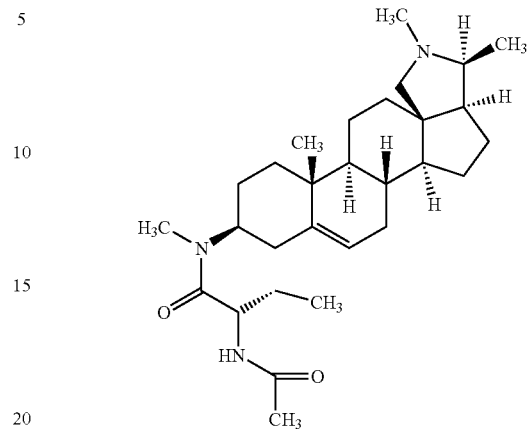

2-Acetylamino-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 61, except substituting Boc-D-2-ethyl-glycine for Boc-N-methyl-D-valine, and further treating according to the procedures described in Example 62 and 63. MS: $(M+H)^+=470$.

Example 76

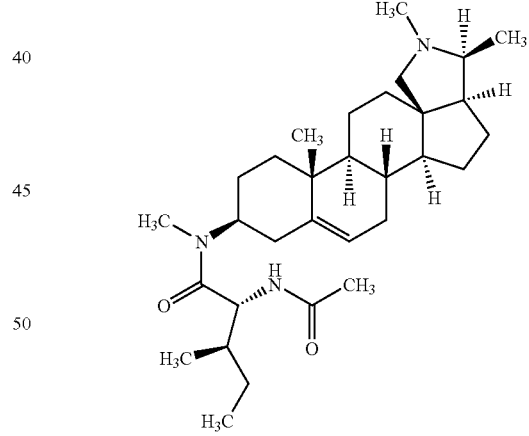

2-Acetylamino-3-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 61, except substituting Boc-D-isoleucine for Boc-N-methyl-D-valine, and further treating according to the procedures described in Example 62 and 63. MS: $(M+H)^+=470$. $^1$H NMR (CDCl$_3$): δ 0.85-2.85 (m, 32 H) 2.00 (d, 3 H) 2.38 (m, 6 H), 2.86 (s, 3 H) 3.00 (s, 3 H) 4.35 (m, 1 H) 4.83 (m, 1 H) 5.36 (m, 1 H) 6.17 (m, 1 H); MS: (M+H)⁺=498.

Example 77

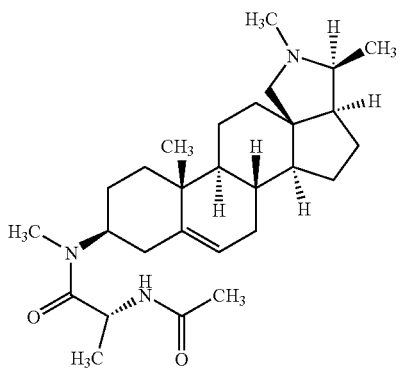

2-Acetylamino-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide A mixture of compound 7B (15 mg, 0.044 mmol), N-acetyl-D-alanine (7 mg, 0.053 mmol), 1-[3-(dimethylamino)propyl]-3-ethylcarbodiimide hydrochloride (13 mg, 0.068 mmol), 1-hydroxybenzotriazole (9 mg, 0.068 mmol), dichloromethane (1 mL) and THF (0.5 mL) was stirred at room temperature overnight. The solvent was evaporated under reduced pressure and the residue was dissolved in minimum amount of dichloromethane and purified on silica gel column which was eluted with 0.3% ammonium hydroxide and 3% methanol in dichloromethane to give the desired product (13 mg, 65% yield).

$^1$H NMR (CDCl$_3$): δ 0.90-1.95(m, 27 H) 2.00 (s, 3 H) 2.05-2.75 (m, 6 H) 2.87 (s, 3 H) 2.93 (s, 3 H) 4.32 (m, 1 H) 4.83 (m, 1 H) 5.37 (m, 1 H) MS: (M+H)⁺=456

Example 78

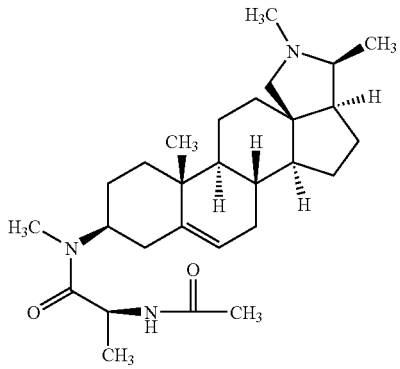

2-Acetylamino-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 77, except substituting N-acetyl-L-alanine for N-acetyl-D-alanine. $^1$H NMR (CDCl$_3$): δ 0.95 (m, 3 H) 1.00-2.80 (m, 28H) 2.00 (s, 3 H) 2.87 (s, 3 H) 2.93 (s, 3 H) 3.62 (m, 1 H) 4.32 (m, 1 H) 4.85 (m, 1 H) 5.37 (m, 1 H) 6.68 (m, 1 H); MS: (M+H)⁺=456.

Example 79

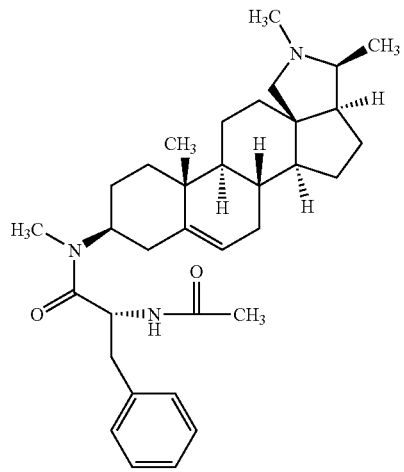

2-Acetylamino-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 77, except substituting N-acetyl-D-phenylalanine for N-acetyl-D-alanine. $^1$H NMR (CDCl$_3$): δ 0.89 (m, 3 H) 1.04 (d, 3 H) 1.05-1.50 (m, 7 H) 1.50-1.90 (m, 9 H) 1.97 (s, 3 H) 2.07 (m, 2 H) 2.20 (s, 3 H) 2.34 (m, 2 H) 2.49 (s, 3 H) 2.78 (d, 2 H) 298 (m, 2 H) 3.39 (m, 1 H) 4.27 (m, 1 H) 5.15 (m, 1 H) 5.37 (m, 1 H) 6.41 (m, 1 H) 7.22 (m, 5). MS: (M+H)⁺=532.

Example 80

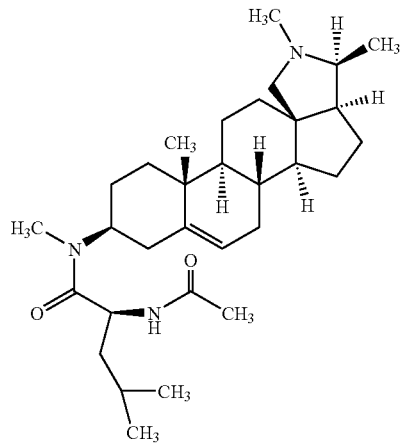

2-Acetylamino-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 77, except substituting N-acetyl-L-leucine for N-acetyl-D-alanine. $^1$H NMR (CDCl$_3$): δ 6.30 (m,1 H), 5.40 (m,1 H), 5.00 (m,1 H), 4.30 (m,1 H), 3.60 (m, 1 H), 2.95 (s, 3H), 2.83 (s, 3H), 2.60-0.80 (m, 40H); MS: (M+H)$^+$=498.

Example 81

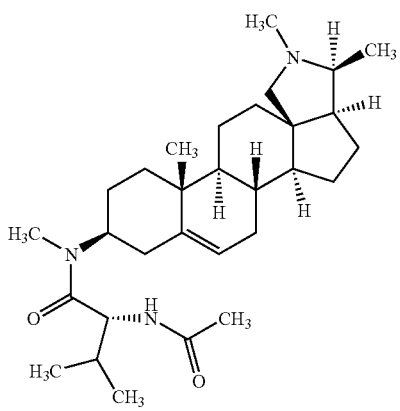

2-Acetylamino-3, N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 77, except substituting N-acetyl-D-valine for N-acetyl-D-alanine. MS: (M+H)$^+$=484.

Example 82

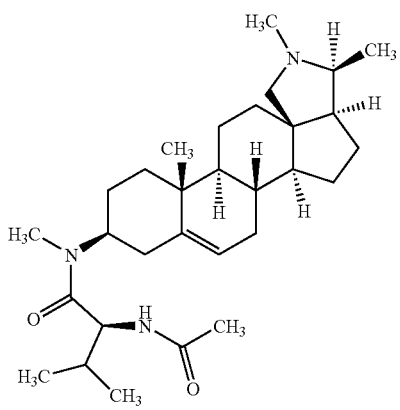

2-Acetylamino-3, N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 77, except substituting N-acetyl-L-valine for N-acetyl-D-alanine. MS: (M+H)$^+$=484.

Example 83

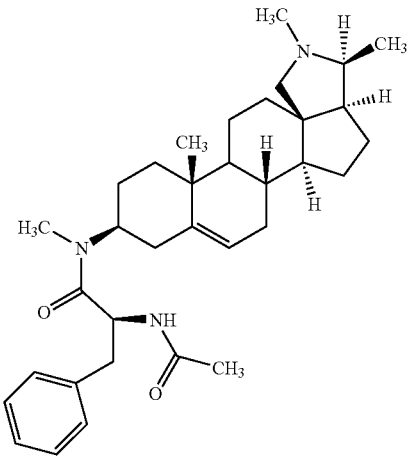

2-Acetylamino-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 77, except substituting N-acetyl-L-phenylalanine for N-acetyl-D-alanine. $^1$H NMR (CDCl$_3$): δ 0.88 (m, 3 H) 0.95-2.50 (m, 26 H) 1.98 (s, 3 H) 2.48 (s, 3 H) 2.78 (s, 3 H) 2.97 (m, 2 H) 4.27 (m, 1 H) 5.15 (m, 1 H) 5.30 (m, 1 H) 6.39 (m,1 H) 7.20 (m, 5 H); MS: (M+H)$^+$=532.

Example 84

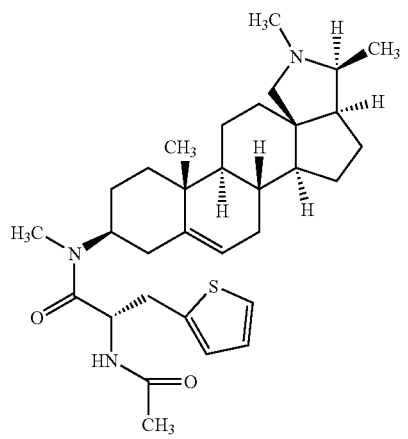

2-Acetylamino-N-methyl-3-thiophen-2-yl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 77, except substituting (S)—N-acetyl-2-(thien-2-yl)-alanine for N-acetyl-D-alanine. $^1$H NMR (CDCl$_3$): δ 0.93 (m, 3 H) 1.04 (d, 3 H) 1.05-1.50 (m, 7 H) 1.50-1.90 (m, 9 H) 1.97 (s, 3 H) 2.07 (m, 2 H) 2.20 (s, 3 H) 2.34 (m, 2 H) 2.49 (s, 3 H) 2.78 (d, 2 H) 2.98 (m, 2 H) 3.39 (m, 1 H) 4.27 (m, 1 H) 5.15 (m, 1 H) 5.37 (m, 1 H) 6.41 (m, 1 H) 7.22 (m, 5 H); MS: (M+H)$^+$=538.

Example 85

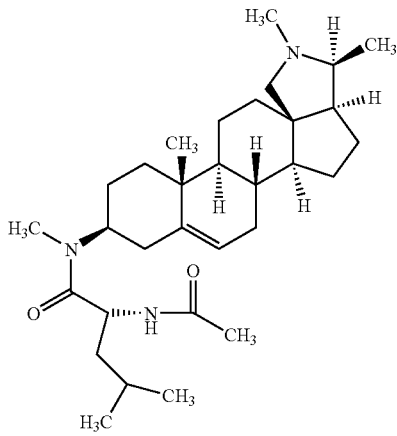

2-Acetylamino-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 77, except substituting N-acetyl-D-leucine for N-acetyl-D-alanine. $^1$H NMR (CDCl$_3$): δ 0.88-2.60 (m, 37 H) 2.03 (s, 3 H) 2.86 (s, 3 H 2.95 (s, 3 H) 3.62 (m, 1 H) 4.30 (m, 1 H) 4.98 (m, 1 H) 5.40 (m, 1 H) 6.30 (m, 1 H); MS: (M+H)$^+$=498.

Example 86

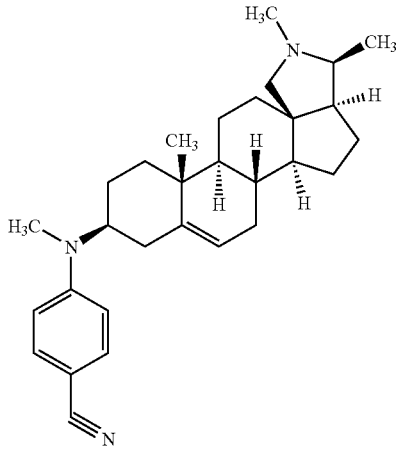

4-[Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amino]-benzonitrile Compound 7B (20 mg, 0.058 mmol), 4-bromobenzonitrile (16 mg, 0.088 mmol), tris(dibenzylideneacetone)dipallidium (2.1 mg, 0.0023 mmol), racemic-2,2'- bis(diphenylphosphino)-1,1'-binaphthyl (BINAP) (2.2 mg, 0.0035 mmol), cesium carbonate (29 mg, 0.088 mmol) and toluene (1 mL) were mixed and heated at 100° C. overnight. The reaction mixture was cooled, quenched with water, and extracted with dichloromethane 3×. Combined organic layer was dried over sodium sulfate, filtered and concentrated to give the crude product, which was then purified on silica gel column which was eluted with 0.3% ammonium hydroxide and 3% methanol in dichloromethane to give the desired product (12 mg, 46% yield).

$^1$H NMR (CDCl$_3$): δ 0.85-2.80(m, 32 H) 2.88 (s, 3 H) 3.63 (m, 1 H) 5.39 (m, 1 H) 6.69 (d, J=8.80 Hz, 2 H) 7.44 (d, J=8.80 Hz, 2 H) MS: (M+H)$^+$=444

Example 87

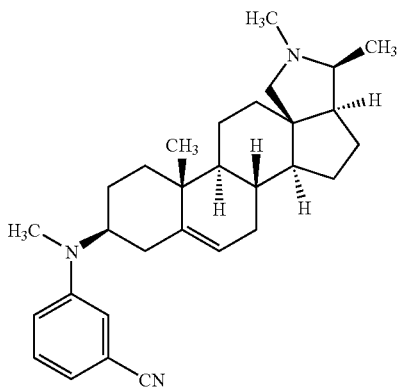

3-[Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amino]-benzonitrile The title compound was prepared according to the procedures described in Example 86, except substituting 3-bromobenzonitrile for 4-bromobenzonitrile. $^1$H NMR (CDCl$_3$): δ 0.99 (s, 3H) 1.05-2.50 (m, 28H) 2.83 (s, 3H) 3.00 (m, 1 H) 3.55(m, 1H) 5.38 (m, 1 H) 6.92 (m, 2H) 7.25 (m, 2H) MS: (M+H)$^+$=444

Example 88

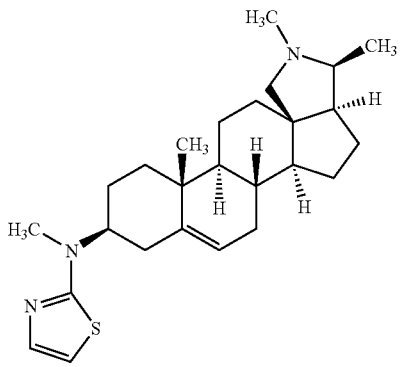

83

Methyl-thiazol-2-yl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amine The title compound was prepared according to the procedures described in Example 86, except substituting 2-bromothiazole for 4bromobenzonitrile. $^1$H NMR (CDCl$_3$): δ 0.99 (s, 3H) 1.03-2.55 (m, 29H) 3.00 (s, 3H) 3.85 (m, 1H) 5.40 (m, 1H) 6.46 (d, J=3.39 Hz, 1 H) 7.17 (d, J=3.39 Hz, 1 H); MS: (M+H)$^+$=426.

Example 89

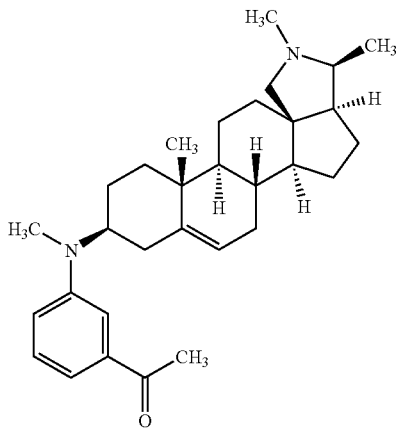

1-{3-[Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amino]-phenyl}-ethanone The title compound was prepared according to the procedures described in Example 86, except substituting 2-bromoacetophenone for 4-bromobenzonitrile. $^1$H NMR (CDCl$_3$): δ 0.97 (s, 3H) 1.04-2.60 (m, 28 H) 2.83 (s, 3H) 2.87 (s, 3H) 2.00 (m, 1H) 3.15 (m, 1H) 5.40 (m, 1H) 7.30 (m, 3H) 8.13 (s, 1H); MS: (M+H)$^+$=461.

Example 90

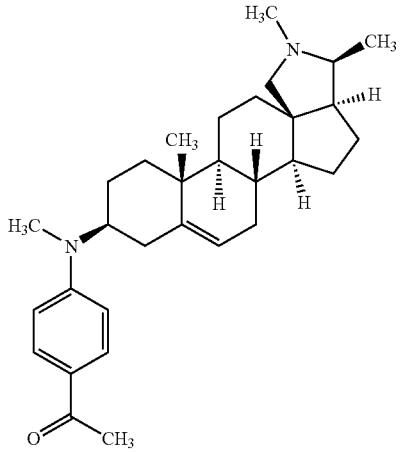

84

1-{4-[Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amino]-phenyl}-ethanone The title compound was prepared according to the procedures described in Example 86, except substituting 4-bromoacetophenone for 4-bromobenzonitrile. MS: (M+H)$^+$=461.

Example 91

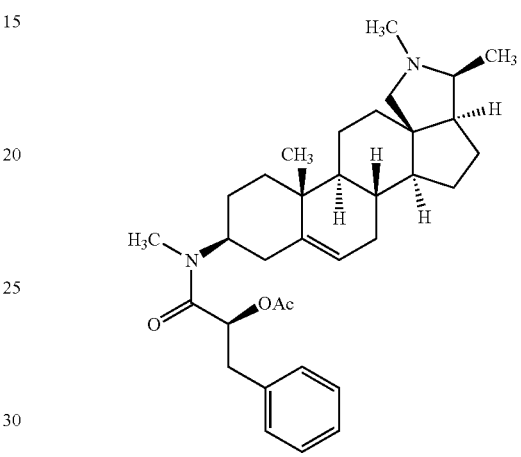

Acetic acid 1-[methyl-(2,3,11a-trimethyl-2,3,3a,4,5,5a,5b,6,8,9,10,11,1a,11b,12,13-hexadecahydro-1H-2-aza-pentaleno[1,6a-a]phenanthren-9-yl)-carbamoyl]-2-phenyl-ethyl ester L-3-Phenyllactic acid (0.2 g, 1.2 mmol) was suspended in 3 mL of dichloromethane. Pyridine (0.234 mL, 2.89 mmol) was added and the suspension became a clear solution. Acetyl chloride (0.103 mL, 1.4 mmol) was added dropwise at room temperature, the clear solution became cloudy. The mixture was stirred at room temperature for 4 hours, then quenched with 10% aqueous citric acid, extracted with dichloromethane 3×. The combined organic layers were dried over sodium sulfate, filtered, and the filtrate was concentrated to give the crude L-2-acetoxy-3-phenyl-propionic acid, which was used in the next step without purification.

A mixture of compound 7B (40 mg, 0.117 mmol), L-2-acetoxy-3-phenyl-propionic acid (37 mg, 0.175 mmol), 1-[3-(dimethylamino)propyl]-3-ethylcarbodiimide hydrochloride (45 mg, 0.235 mmol), 1-hydroxybenzotriazole (32 mg, 0.235 mmol) and dichloromethane (1.5 mL) was stirred at room temperature overnight. The solvent was evaporated under reduced pressure and the residue was dissolved in minimum amount of dichloromethane and purified on silica gel column which was eluted with 0.3% ammonium hydroxide and 3% methanol in dichloromethane to give the desired product (50 mg, 81% yield).

$^1$H NMR (CDCl$_3$): δ 0.89 (d, 3 H) 0.95-1.90 (m, 18 H) 2.08 (s, 3 H) 2.18 (m, 3 H) 2.38 (m, 2 H) 2.64 (s, 3 H) 2.79 (s, 3 H) 2.97 (m, 1 H) 3.10 (m, 2 H) 3.37 (m, 1H) 4.32 (m, 1 H) 5.35 (m, 2 H) 5.52 (m, 1 H) 7.27 (m, 5 H) MS: (M+H)$^+$=533

Example 92

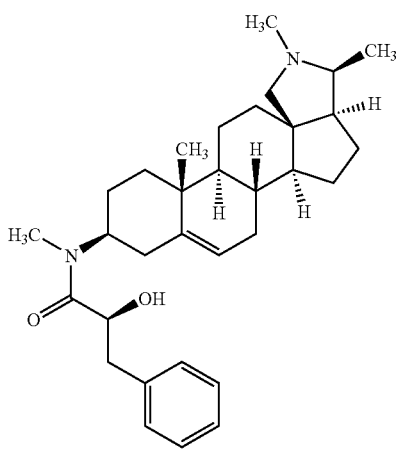

2-Hydroxy-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide Potassium carbonate (51 mg, 0.37 mmol) in 0.5 mL water was added to Compound 91 (36 mg, 0.073 mmol) in 1 mL methanol. The mixture was stirred at room temperature for 4 hours, then quenched with 1 mL water and extracted with dichloromethane to give the crude product which was purified on silica gel column and eluted with 0.3% ammonium hydroxide and 3% methanol in dichloromethane to give the desired product (25 mg, 76% yield).
$^1$H NMR (CDCl$_3$): δ 0.93 (s, 3 H) 1.00-2.60 (m, 25 H) 2.66 (s, 3 H) 2.89 (m, 4 H) 3.36 (m, 1 H) 3.76 (m, 1 H) 4.32 (m, 1 H) 4.57 (m, 2 H) 5.38 (m, 1 H) 7.25 (m, 5 H) MS: (M+H)$^+$=491

Example 93

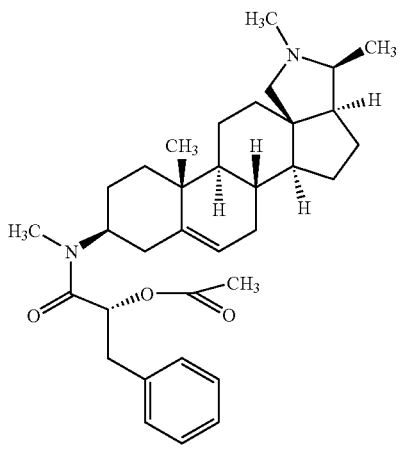

Acetic acid 1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-2-phenyl-ethyl ester The title compound was prepared according to the procedures described in Example 91, except substituting D-3-phenyllactic acid for L-3-phenyllactic acid. $^1$H NMR (CDCl$_3$): δ 0.90 (d, J=5.09 Hz, 3 H) 1.00-2.40 (m, 25 H) 2.64 (s, 3 H) 2.80 (s, 3 H) 3.10 (m, 4 H) 3.56 (m, 1 H) 4.32 (m, 1 H) 5.19 (m, 1 H) 5.36 (m, 1 H) 5.46 (m, 1 H) 7.26 (m, 5 H)
MS: (M+H)$^+$=533

Example 94

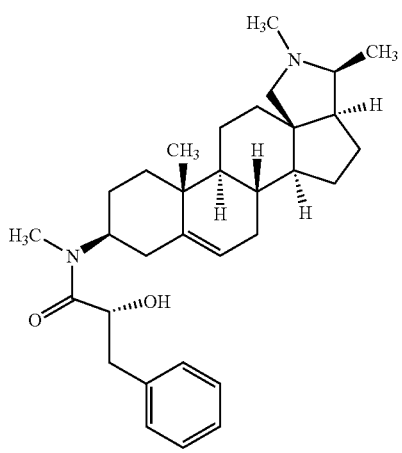

2-Hydroxy-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 92, except substituting compound 93 for compound 91. $^1$H NMR (CDCl$_3$): δ 0.95 (d, J=4.75 Hz, 3 H) 1.03 (m, 3 H) 1.14-2.50 (m, 22H) 2.66 (s, 3 H) 2.92 (m, 5) 3.41 (m, 1 H) 3.79 (dd, J=8.14, 2.71 Hz, 1 H) 4.31 (m, 1 H) 4.54 (m, 1 H) 5.37 (m, 1 H) 7.26 (m, 5 H) MS: (M+H)$^+$=491

Example 95

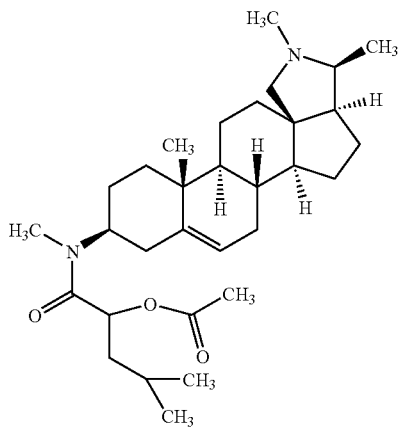

Acetic acid 3-methyl-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-butyl ester The title compound was prepared according to the procedures described in Example 91, except substituting 2-hydroxyisocaproic acid for L-3-phenyllactic acid. MS: (M+H)$^+$=499

Example 96

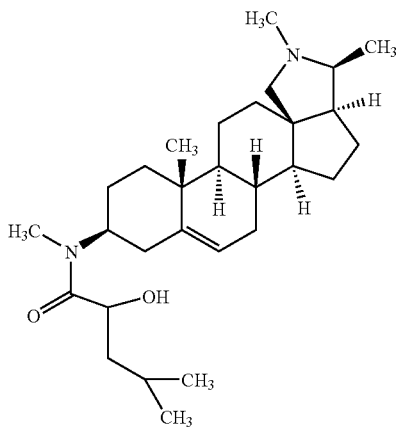

2-Hydroxy-4-methyl-pentanoic acid methyl-(2,3, 11a-trimethyl-2,3,3a,4,5,5a,5b,6,8,9,10,11,11a,11b, 12,13-hexadecahydro-1H-2-aza-pentaleno[1,6a-a] phenanthren-9-yl)-amide The title compound was prepared according to the procedures described in Example 92, except substituting compound 95 for compound 91. MS: (M+H)$^+$=457

Example 97

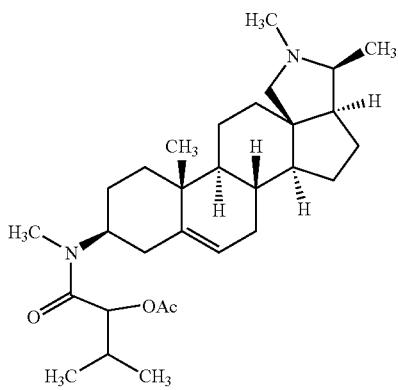

Acetic acid 2-methyl-1-[-methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-propyl ester The title compound was prepared according to the procedures described in Example 91, except substituting 2-hydroxy-3-methylbutyric acid for L-3-phenyllactic acid. $^1$H NMR (CDCl$_3$): δ 0.95-2.75 (m, 34 H) 2.12 (s, 3 H) 2.86 (s, 3 H) 3.00 (s, 3 H) 3.71 (m, 1 H) 4.39 (m, 1 H) 4.97 (m, 1 H) 5.08 (m, 1 H) 5.36 (m, 1 H)
MS: (M+H)$^+$=485

Example 98

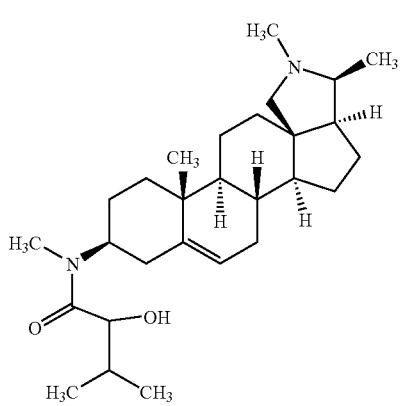

2-Hydroxy-3, N-dimethyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 92, except substituting compound 97 for compound 91. MS: (M+H)$^+$=443

Example 99

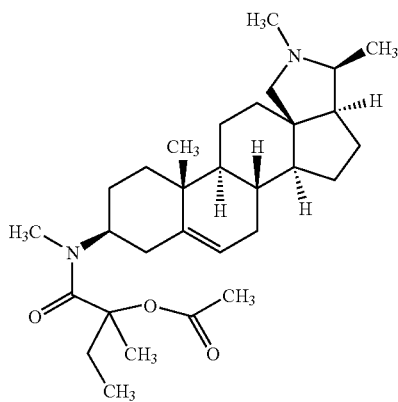

Acetic acid 1-methyl-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-propyl ester The title compound was prepared according to the procedures described in Example 91, except substituting 2-hydroxy-2-methylbutyric acid for L-3-phenyllactic acid. MS: (M+H)$^+$=485

Example 100

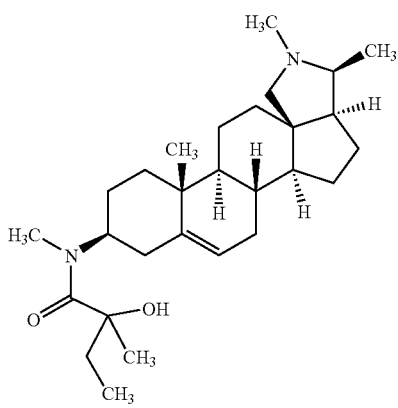

2-Hydroxy-2, N-dimethyl-N-(2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl)-butyramide The title compound was prepared according to the procedures described in Example 92, except substituting compound 99 for compound 91. $^1$H NMR (CDCl$_3$): δ 0.96 (m, 3 H) 1.05-2.60 (m, 33 H) 2.84 (s, 3 H) 2.87 (s, 3 H) 2.98 (m, 1 H) 3.50 (m, 1 H) 4.42 (m, 1 H) 5.37 (m, 1 H)

MS: (M+H)$^+$=443

Example 101

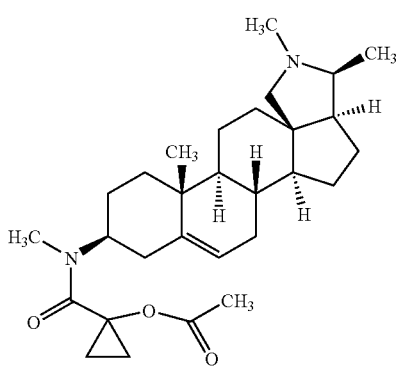

Acetic acid 1-[methyl-(2,3,11a-trimethyl-2,3,3a,4,5, 5a,5b,6,8,9,10,11,11a,11b,12,13-hexadecahydro-1H-2-aza-pentaleno[1,6a-a]phenanthren-9-yl)-carbamoyl]-cyclopropyl ester The title compound was prepared according to the procedures described in Example 91, except substituting 1-hydroxy-1-cyclopropanecarboxylic acid for L-3-phenyllactic acid. MS: (M+H)$^+$=469

Example 102

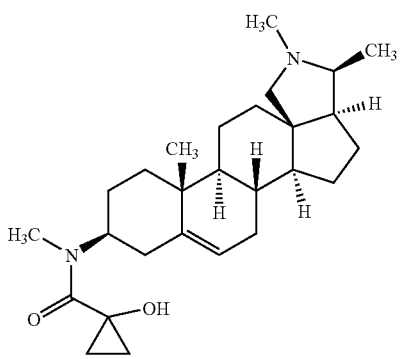

1-Hydroxy-cyclopropanecarboxylic acid methyl-(2, 3,11a-trimethyl-2,3,3a,4,5,5a,5b,6,8,9,10,11,11a,11b, 12,13-hexadecahydro-1H-2-aza-pentaleno[1,6a-a] phenanthren-9-yl)-amide The title compound was prepared according to the procedures described in Example 92, except substituting compound 101 for compound 91. $^1$H NMR (CDCl$_3$): δ 0.78-2.60 (m, 31 H) 2.87 (s, 3 H) 2.91 (s, 3 H) 3.01 (m, 1 H) 3.72 (m, 1 H) 4.21 (m, 1 H) 4.35 (m, 1 H) 5.38 (m, 1 H)

MS: (M+H)$^+$=427

Example 103

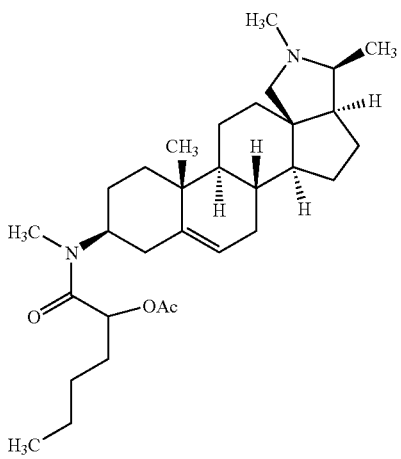

Acetic acid 1-[methyl-(2,3,11a-trimethyl-2,3,3a,4,5, 5a,5b,6,8,9,10,11,11a,11b,12,13-hexadecahydro-1H-2-aza-pentaleno[1,6a-a]phenanthren-9-yl)-carbamoyl]-pentyl ester The title compound was prepared according to the procedures described in Example 91, except substituting 2-hydroxycaproic acid for L-3phenyllactic acid. $^1$H NMR (CDCl$_3$): δ 0.91-2.60 (m, 37 H) 2.12 (s, 3 H) 2.86 (s, 3 H) 2.95 (s, 3 H) 3.58 (m, 1 H) 4.35 (m, 1 H) 5.24 (m, 1 H) 5.36 (m, 1 H)

MS: (M+H)$^+$=499

Example 104

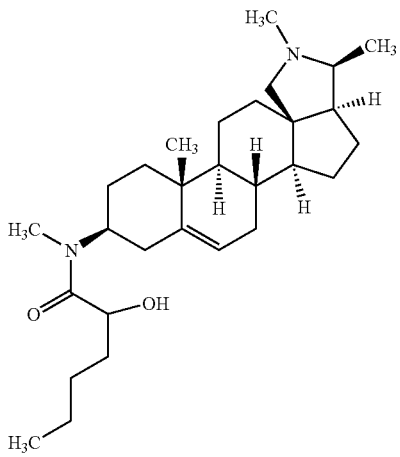

2-Hydroxy-hexanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 92, except substituting compound 103 for compound 91. $^1$H NMR (CDCl$_3$): δ 0.88-2.60 (m, 37 H) 2.85 (s, 3 H) 2.90 (s, 3 H) 2.99 (m, 1 H) 3.35 (m, 1 H) 3.83 (m, 1 H) 4.33 (m, 1 H) 5.38 (m, 1 H)
MS: (M+H)$^+$=457

Example 105

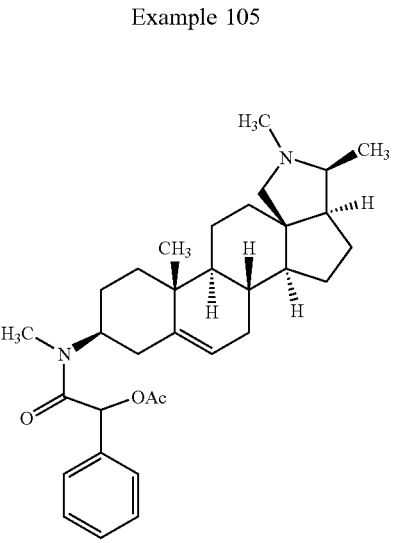

Acetic acid [methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-phenyl-methyl ester The title compound was prepared according to the procedures described in Example 91, except substituting DL-mandelic acid for L-3-phenyllactic acid. MS: (M+H)$^+$=519

Example 106

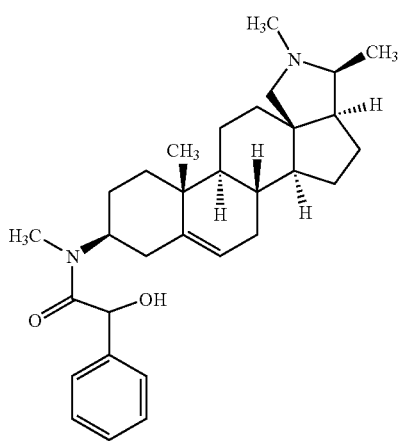

2-Hydroxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 92, except substituting compound 105 for compound 91. MS: (M+H)$^+$=477

Example 107

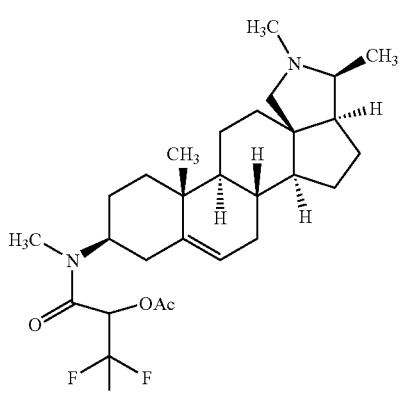

Acetic acid 2,2,2-trifluoro-1-[methyl-(2,3,1a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-ethyl ester The title compound was prepared according to the procedures described in Example 91, except substituting 3,3,3-trifluoro-2-hydroxypropanoic acid for L-3-phenyllactic acid. MS: (M+H)$^+$=511, (M+NH$^4$)$^+$=528

Example 108

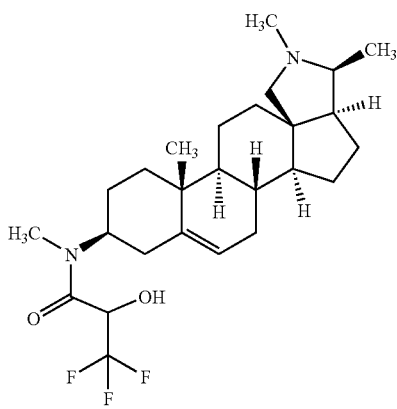

3,3,3-Trifluoro-2-hydroxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to the procedures described in Example 92, except substituting compound 107 for compound 91. $^1$H NMR (CDCl$_3$): δ 0.97 (s, 3 H) 1.05-2.60 (m, 26H) 2.95 (s, 3 H) 2.99 (s, 3 H) 3.42 (m, 1 H) 4.43 (m, 1 H) 4.76 (m, 1 H) 5.40 (m, 1 H)
MS: (M+H)$^+$=469, (M+NH$_4$)$^+$=486

Example 109

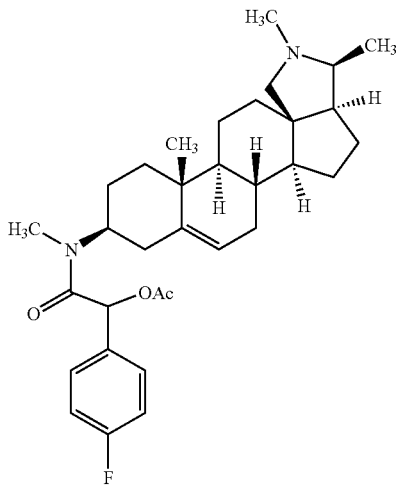

Acetic acid (4-fluoro-phenyl)-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-methyl ester The title compound was prepared according to the procedures described in Example 91, except substituting 4-fluoromandelic acid for L-3-phenyllactic acid. $^1$H NMR (CDCl$_3$): δ 0.92 (m, 3 H) 1.00-2.60 (m, 23 H) 2.16 (s, 3 H) 2.79 (s, 3 H) 2.85 (s, 3 H) 3.00 (m, 1 H) 3.52 (m, 1 H) 4.32 (m, 1 H) 4.90 (m, 1 H) 5.38 (m, 1 H) 6.18 (m, 1 H) 7.08 (m, 2 H) 7.43 (m, 2 H)
MS: (M+H)$^+$=537

Example 110

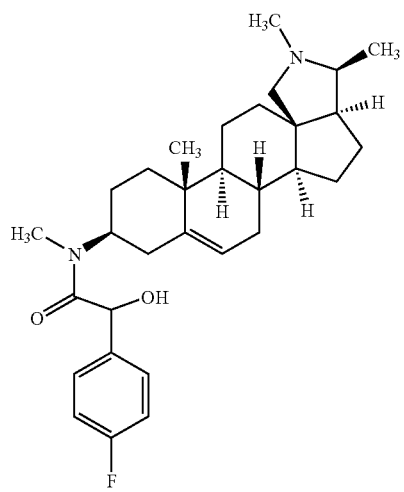

2-(4-Fluoro-phenyl)-2-hydroxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 92, except substituting compound 109 for compound 91. $^1$H NMR (CDCl$_3$): δ 0.86 (s, 3 H) 1.00-2.50 (m, 25 H) 2.62 (s, 3 H) 2.91 (s, 3 H) 3.30 (m, 1 H) 4.82 (m, 1 H) 4.97 (m, 1 H) 5.15 (m, 1 H) 5.38 (m, 1 H) 7.04 (m, 2 H) 7.28 (m, 2 H)
MS: (M+H)$^+$=495

Example 111

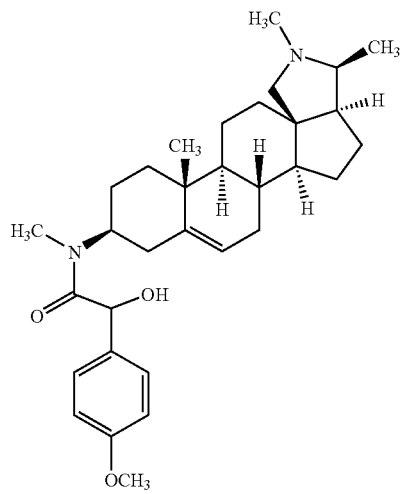

Acetic acid (4-methoxy-phenyl)-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-methyl ester The title compound was prepared according to the procedures described in Example 91, except substituting 4-methoxymandelic acid for L-3-phenyllactic acid. $^1$H NMR (CDCl$_3$): δ 0.89 (d, J=9.83 Hz, 3 H) 1.00-2.60 (m, 24 H) 2.15 (s, 3 H) 2.76 (s, 3 H) 2.85 (s, 3 H) 2.96 (m, 1 H) 3.55 (m, 1 H) 3.82 (s, 3 H) 4.39 (m, 1 H) 5.40 (m, 1 H) 6.14 (m, 1 H) 6.90 (m, 2 H) 7.36 (m, 2 H)
MS: (M+H)$^+$=549

Example 112

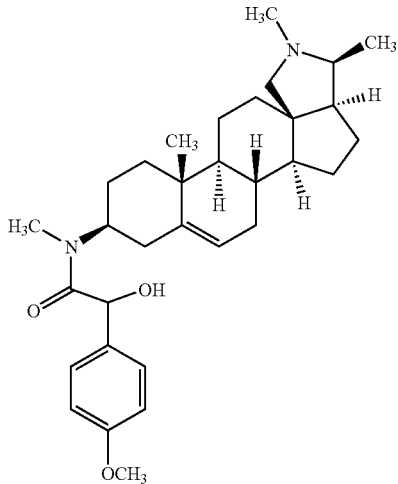

2-Hydroxy-2-(4-methoxy-phenyl)-N-methyl-N-(2,3,11a-trimethyl-2,3,3a,4,5,5a,5b,6,8,9,10,11,11a,11b,12,13-hexadecahydrol-1H-2-aza-pentaleno[1,6a-a]phenanthren-9-yl)-acetamide The title compound was prepared according to the procedures described in Example 92, except substituting compound 111 for compound 91. $^1$H NMR (CDCl$_3$): δ 0.85 (s, 3 H) 0.92 (s, 3 H) 1.04-2.60 (m, 21 H) 2.62 (s, 3 H) 2.90 (s, 3 H) 2.97 (m, 1 H) 3.42 (m, 1 H) 3.81 (s, 3 H) 4.77 (m, 1 H) 4.92 (m, 1 H) 5.13 (m, 1 H) 5.38 (m, 1 H) 6.88 (m, 2 H) 7.23 (m, 2 H)
MS: (M+H)$^+$=507

Example 113

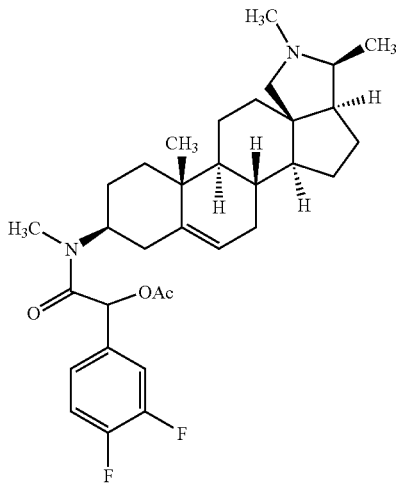

Acetic acid (3,4-difluoro-phenyl)-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-methyl ester The title compound was prepared according to the procedures described in Example 91, except substituting 3,3-difluoromandelic acid for L-3-phenyllactic acid. $^1$H NMR (CDCl$_3$): δ 0.91 (d, J=6.10 Hz, 3 H) 1.00-2.60 (m, 28 H) 2.16 (s, 3 H) 2.85 (m, 3 H) 2.98 (m, 1 H) 4.34 (m, 1 H) 5.38 (m, 1 H) 6.14 (m, 1 H) 7.18 (m, 2 H) 7.34 (m, 1 H)
MS: (M+H)$^+$=555

Example 114

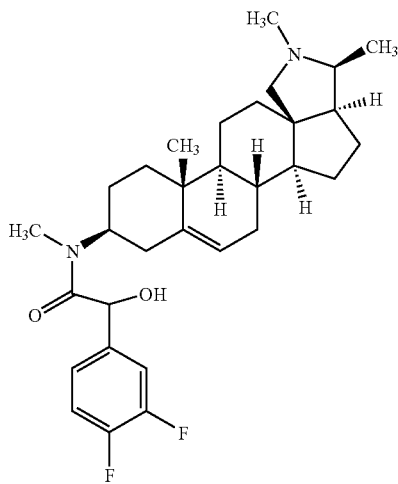

2-(3,4-Difluoro-phenyl)-2-hydroxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 92, except substituting compound 113 for compound 91. $^1$H NMR (CDCl$_3$): δ 0.87 (s, 3 H) 0.93 (s, 3 H) 1.05-2.55 (m, 20 H) 2.65 (s, 3 H) 2.91 (s, 3 H) 2.98 (m, 1 H) 3.33 (m, 1 H) 4.38 (m, 1 H) 4.82 (m, 1 H) 4.98 (m, 1 H) 5.13 (m, 1 H) 5.39 (m, 1 H) 7.14 (m, 3 H)
MS: (M+H)$^+$=513

Example 115

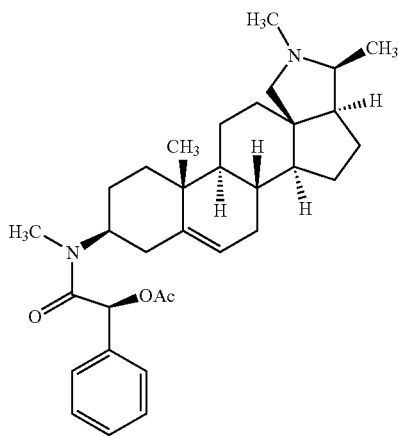

Acetic acid [methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-phenyl-methyl ester The title compound was prepared according to the procedures described in Example 91, except substituting (S)-(+)-mandelic acid for L-3phenyllactic acid. ¹H NMR (CDCl₃): δ 0.88-2.50 (m, 29 H) 2.78 (s, 3 H) 2.85 (s,3 H) 2.95 (t,J=9.05 Hz, 2 H) 3.56 (m, 1 H) 4.37 (m, 1 H) 5.38 (m, 1 H) 6.20 (m, 1 H) 7.41 (m, 5 H)
MS: (M+H)⁺=519

Acetic acid [methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-phenyl-methyl ester The title compound was prepared according to the procedures described in Example 91, except substituting (R)-(−)-mandelic acid for L-3-phenyllactic acid. ¹H NMR (CDCl₃): δ 0.88 (d, J=11.19 Hz, 3 H) 1.00-2.60 (m, 24H) 2.17 (s, 3 H) 2.78 (s, 3 H) 2.85 (s, 3 H) 3.26 (m, 1 H) 3.62 (m, 1 H) 4.37 (m, 1 H) 5.37 (m, 1 H) 6.16 (d,J=4.07 Hz, 1 H) 7.41 (m, 5 H)
MS: (M+H)⁺=519

Example 116

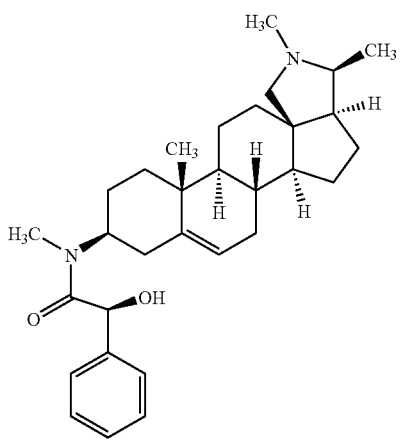

2-Hydroxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 92, except substituting compound 115 for compound 91. ¹H NMR (CDCl₃): δ 0.85 (s, 3 H) 1.03 (d, J=6.44 Hz, 3 H) 1.05-2.50 (m, 19 H) 2.62 (s, 3 H) 2.90 (s, 3 H) 2.95 (m, 2 H) 3.42 (m, 1 H) 4.41 (m, 1 H) 4.75 (m, 1 H) 4.96 (m, 1 H) 5.18 (m, 1) 5.40 (m, 1 H) 7.32 (m, 5 H)
MS: (M+H)⁺=477

Example 118

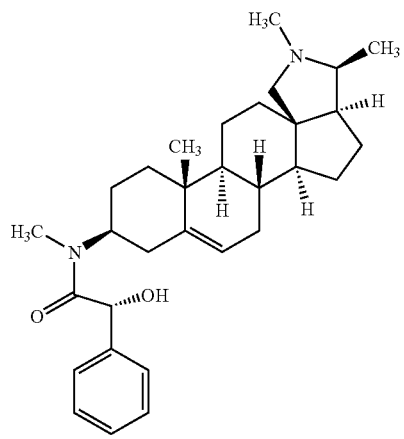

2-Hydroxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 92, except substituting compound 117 for compound 91. ¹H NMR (CDCl₃): δ 0.85 (s, 3 H) 1.03 (d, J=6.24 Hz, 3 H) 1.10-2.50 (m, 16H) 2.19 (s, 3 H) 2.62 (s, 3 H) 2.90 (s, 3 H) 2.95 (m, 2 H) 3.42 (m, 1 H) 4.41 (m, 1 H) 4.74 (m, 1 H) 4.98 (m,1 H) 5.19 (m, 1 H) 5.39 (m, 1 H) 7.32 (m, 5 H)
MS: (M+H)⁺=477

Example 117

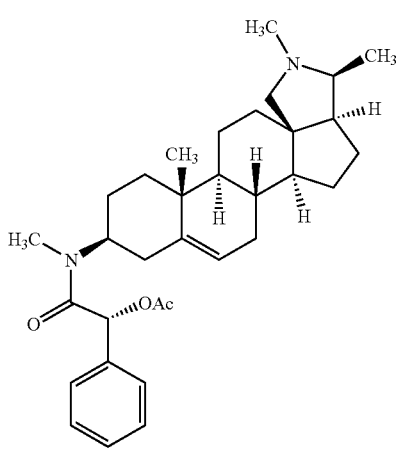

Example 119

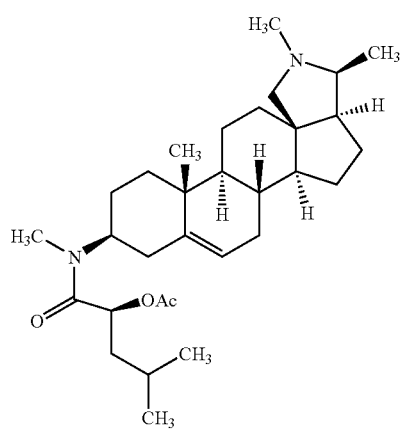

Acetic acid 3-methyl-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-butyl ester The title compound was prepared according to the procedures described in Example 91, except substituting (S)-(−)-2-hydroxyisocaproic acid for L-3-phenyllactic acid. ¹H NMR (CDCl₃): δ 0.90-2.60 (m, 33 H) 2.11 (s, 3 H) 2.41 (m, 3 H) 2.85 (s, 3 H) 2.93 (s, 3 H) 2.94 (m, 1 H) 3.53 (m, 1 H) 4.34 (m, 1 H) 5.33 (m, 2 H)
MS: (M+H)⁺=499

Acetic acid 3-methyl-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-butyl ester The title compound was prepared according to the procedures described in Example 91, except substituting (R)-(+)-2-hydroxyisocaproic acid for L-3-phenyllactic acid. ¹H NMR (CDCl₃): δ 0.92-2.65 (m, 33 H) 2.11 (s, 3 H) 2.42 (m, 3 H) 2.85 (s, 3 H) 2.94 (s, 3 H) 3.02 (m, 1 H) 3.60 (m, 1 H) 4.34 (m, 1 H) 5.31 (m, 2 H)
MS: (M+H)⁺=499

Example 120

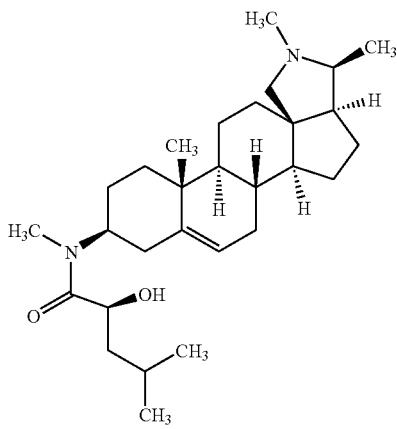

Example 122

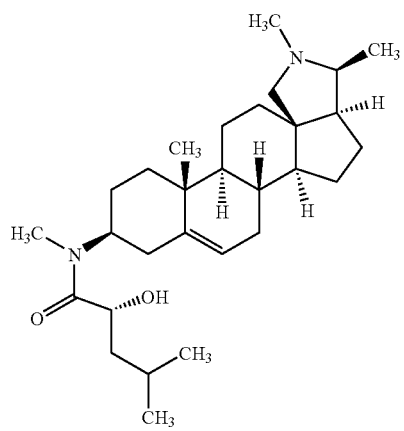

2-Hydroxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 92, except substituting compound 119 for compound 91. ¹H NMR (CDCl₃): δ 0.92-2.60 (m, 38 H) 2.84 (s, 3 H) 2.90 (s, 3 H) 2.95 (m, 1 H) 3.75 (m, 1 H) 4.34 (m, 1 H) 5.38 (m, 1 H)
MS: (M+H)⁺=457

2-Hydroxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to the procedures described in Example 92, except substituting compound 121 for compound 91. ¹H NMR (CDCl₃): δ 0.94-2.60 (m, 38 H) 2.84 (s, 3 H) 2.89 (s, 3 H) 2.95 (m, 1 H) 3.75 (m, 1 H) 4.34 (m, 1 H) 5.40 (m, 1 H)
MS: (M+H)⁺=457

Example 121

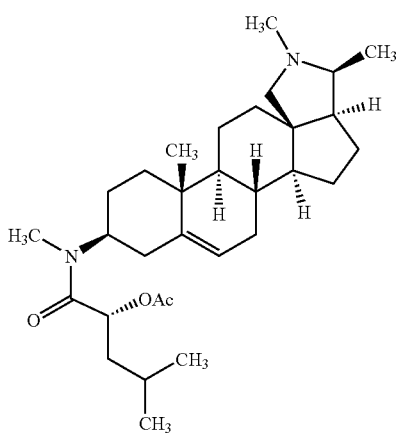

Example 123

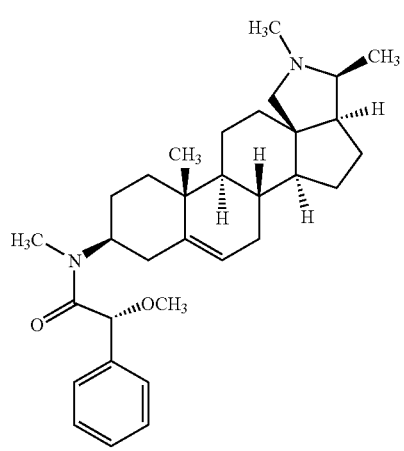

2-Methoxy-N-methyl-2-phenyl-N-2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide A mixture of compound 7B (30 mg, 0.088 mmol), R-(−)-α-methoxyphenylacetic acid (22 mg, 0.132 mmol), 1-[3-(dimethylamino)propyl]-3-ethylcarbodiimide hydrochloride (34 mg, 0.177 mmol), 1-hydroxybenzotriazole (24 mg, 0.177 mmol) and dichloromethane (1 mL) was stirred at room temperature overnight. The solvent was evaporated under reduced pressure and the residue was dissolved in minimum amount of dichloromethane and purified on silica gel column which was eluted with 0.3% ammonium hydroxide and 3% methanol in dichloromethane to give the desired product (40 mg, 93% yield).

$^1$H NMR (CDCl$_3$): δ 0.86 (s, 3 H) 0.91 (s, 3 H) 1.06-2.50 (m, 20 H) 2.74 (s, 3 H) 2.84 (s, 3 H) 3.04 (m, 1 H) 3.45 (s, 3 H) 3.78 (m, 1 H) 4.41 (m, 1 H) 5.02 (d, J=13.22 Hz, 2 H) 5.37 (m, 1 H) 7.36 (m, 5 H) MS: (M+H)$^+$=491

Example 124

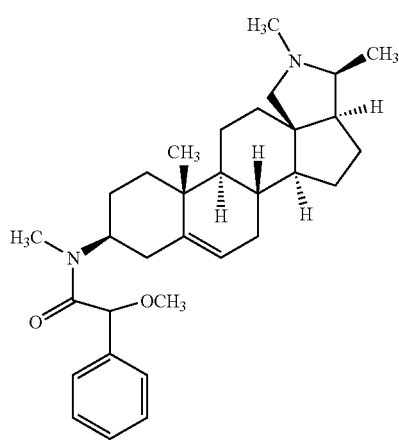

2-Methoxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 123, except substituting 2-methoxyphenylacetic acid for R-(−)-α-methoxyphenylacetic acid. $^1$H NMR (CDCl$_3$): δ 0.86 (s, 3 H) 0.91 (s, 3H) 1.00-2.40 (m, 20 H) 2.74 (s, 3 H) 2.84 (s, 3H) 2.96 (m, 1 H) 3.74 (m, 3H) 3.78 (m, 1H) 4.40 (m, 1H) 5.02 (d, J=11.87 Hz, 2 H) 5.37 (m, 1 H) 7.36 (m, 5 H); MS: (M+H)$^+$=491.

Example 125

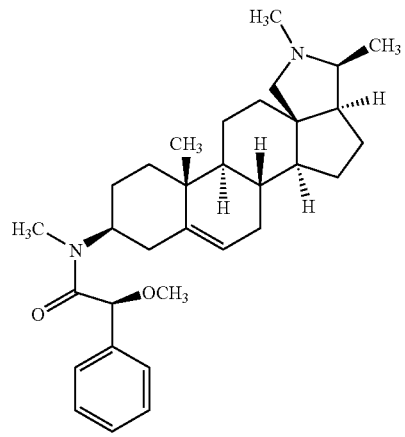

2-Methoxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide The title compound was prepared according to the procedures described in Example 123, except substituting (S)-(+)-α-methoxyphenylacetic acid for R-(−)-α-methoxyphenylacetic acid. $^1$H NMR (CDCl$_3$): δ 0.86 (s, 3 H) 0.91 (s, 3 H) 1.06-2.50 (m, 20 H) 2.74 (s, 3 H) 2.84 (s, 3 H) 3.01 (m, 1 H) 3.46 (s, 3 H) 3.76 (m, 1 H) 4.39 (m, 1 H) 5.02 (d, J=11.87 Hz, 2 H) 5.37 (m, 1 H) 7.36 (m, 5 H); MS: (M+H)$^+$=491.

Example 126

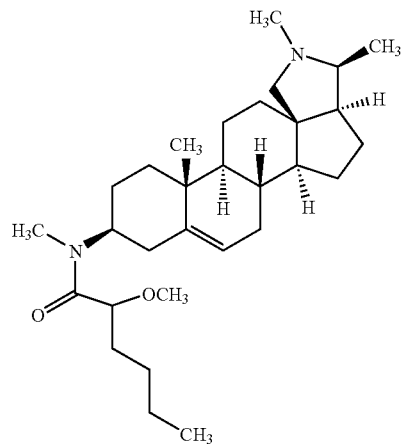

2-Methoxy-hexanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide 2-Hydroxy caproic acid (152 mg, 1.15 mmol) was dissolved in 3 mL anhydrous THF. Sodium hydride (95%, 61 mg, 2.41 mmol) was added and the mixture was stirred at room temperature for 40 min. Iodomethane (0.7 mL) was added and the mixture was stirred at room temperature overnight. It was quenched with water, stirred for 4 hours to hydrolyze the methyl ester, and then adjusted to pH 4 with 10% citric acid. The mixture was extracted with 5% methanol in dichloromethane, organic layer dried over sodium sulfate, filtered, and the filtrate was concentrated to give the crude 2-methoxy caproic acid which was used in next step without further purification.

A mixture of compound 7B (30 mg, 0.088 mmol), 2-methoxy caproic acid (20 mg, 0.137 mmol), 1-[3-(dimethylamino)propyl]-3-ethylcarbodimide hydrochloride (34 mg, 0.177 mmol), 1-hydroxybenzotriazole (24 mg, 0.177 mmol) and dichloromethane (1 mL) was stirred at room temperature overnight. The solvent was evaporated under reduced pressure and the residue was dissolved in minimum amount of dichloromethane and purified on silica gel column, which was eluted with 0.3% ammonium hydroxide and 3% methanol in dichloromethane to give the desired product (38 mg, 92% yield).

$^1$H NMR (CDCl$_3$): δ 0.88-2.75 (m, 37 H) 2.87 (s, 3 H) 2.98 (s, 3 H) 3.31 (s, 3H) 3.99 (m, 2 H) 4.40 (m, 1 H) 5.37 (m, 1 H) MS: (M+H)$^+$=471

Example 127

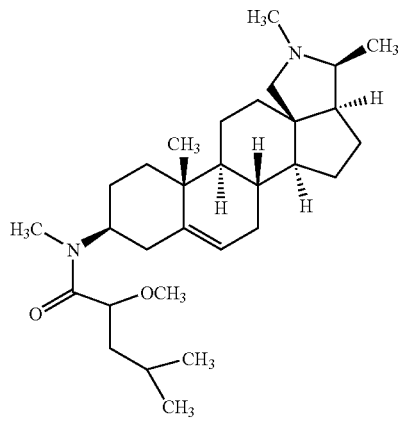

2-Methoxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide The title compound was prepared according to procedures described in Example 126, except substituting 2-hydroxy-isocaproic acid for 2-hydroxy caproic acid. $^1$H NMR (CDCl$_3$): δ 0.91-2.60 (m, 37 H) 2.86 (s, 3 H) 2.97 (s, 3 H) 3.32 (d, J=5.43 Hz, 3 H) 3.91 (m, 1 H) 4.06 (dd, J=9.32, 4.24 Hz, 1 H) 4.40 (m, 1 H) 5.37 (m, 1 H); MS: (M+H)$^+$=4,71.

Example 128

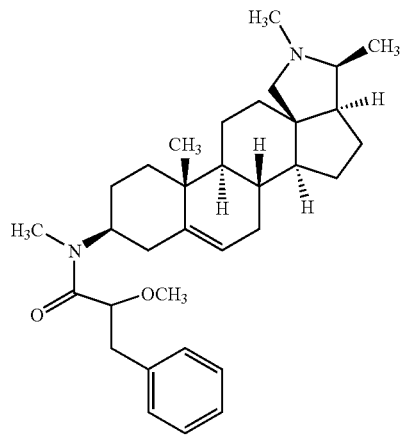

2-Methoxy-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide The title compound was prepared according to procedures described in Example 126, except substituting L-3-phenyl-lactic acid for 2-hydroxy caproic acid. $^1$H NMR (CDCl$_3$): δ 0.93 (m,3 H) 1.04 (d, J=6.24 Hz, 3 H) 1.10-2.60 (m, 18 H) 2.72 (s, 3 H) 2.83 (s, 3 H) 3.02 (m, 6 H) 3.31 (d, J=3.43 Hz, 3 H) 3.61 (m,1 H) 4.29 (m, 1 H) 4.40 (m,1 H) 5.35 (m, 1 H) 7.24 (m, 5 H); MS: (M+H)$^+$=505.

Example 129

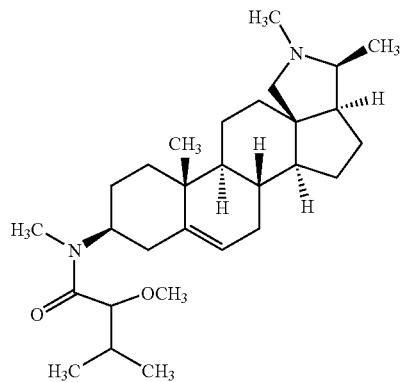

2-Methoxy-3, N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide The title compound was prepared according to procedures described in Example 126, except substituting 2-hydroxy-3methylbutyric acid for 2-hydroxy caproic acid. $^1$H NMR (CDCl$_3$): δ 0.89-2.65 (m, 35 H) 2.88 (s, 3 H) 3.00 (s, 3 H) 3.32 (s, 3 H) 3.64 (m, 1 H) 4.01 (m, 1 H) 4.42 (m, 1 H) 5.36 (m, 1 H); MS: (M+H)$^+$=457.

Example 130

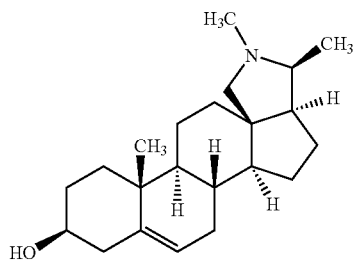

130A. 2,3,11a-Trimethyl-2,3,3a,4,5,5a,5b,6,8,9,10,11,11a,11b,12,13-hexadecahydro-1H-2-aza-pentaleno[1,6a-a]phenanthren-9-ol The title compound was prepared according to the procedure of Hora and Cerny; Collect. Czech. Chem. Commun., 26, 1961, 2217 and Labler et al.; and Collect. Czech. Chem. Commun., 28, 1963, 2015. $^1$H NMR (CDCl$_3$): δ 0.95 (s, 3 H) 1.00-1.50 (m, 12 H) 1.50-2.00 (m, 10 H) 2.07 (m, 1 H) 2.26 (m, 5 H) 2.45 (m, 1 H) 3.05 (m, 1 H) 3.52 (m, 1 H) 5.34 (m, 1 H); MS: (M+H)$^+$=330.

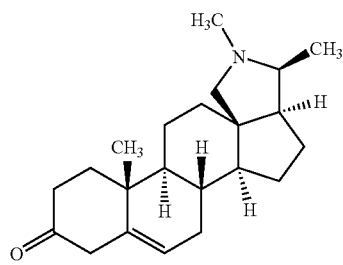

130B. 2,3,11a-Trimethyl-1,2,3,3a,4,5,5a,5b,6,8,10,11,11a,11b,12,13-hexadecahydro-2-aza-pentaleno[1,6a-a]phenanthren-9-one A mixture of Compound 130A (200 mg, 0.607 mmol) Dess-Martin periodinane (386 mg, 0.91 mmol) and dichloromethane (10 mL) was stirred at room temperature for 4.5 hours. The reaction was quenched with 10% sodium thiosulfate and extracted with dichloromethane. Organic layer was dried over sodium sulfate, filtered, and the filtrate was concentrated under reduced pressure to give the crude product, which was purified on silica gel column eluted with 0.3% ammonium hydroxide and 3% methanol in dichloromethane to give the desired product (156 mg, 83% yield).

$^1$H NMR (CDCl$_3$): δ 1.13 (s, 3H) 1.20-2.80 (m, 23 H) 2.73 (s, 3 H) 3.26 (m, 2 H) 3.88 (m, 1 H) 5.35 (m, 1 H) MS: (M+H)$^+$=328

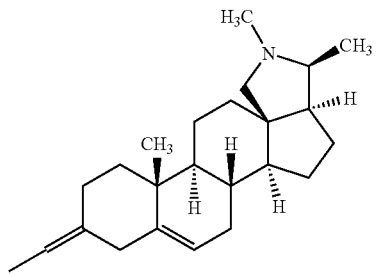

130C. 9-Ethylidene-2,3,11a-trimethyl-2,3,3a,4,5,5a,5b,6,8,9,10,11,11a,11b,12,13-hexadecahydro-1H-2-aza-pentaleno[1,6a-a]phenanthrene Potassium t-butoxide (1.0 M in THF, 0.3 mL, 0.30 mmol) was added dropwise to a stirred solution of ethyl triphenylphosphonium bromide (156 mg, 0.42 mmol) in 2 mL anhydrous toluene. A bright orange suspension resulted and was stirred at room temperature for 5 hours. Compound 130B (25 mg, 0.076 mmol) in 1 mL THF was added to the above suspension and stirred overnight. The reaction was quenched with saturated ammonium chloride and extracted with dichloromethane to give the crude product, which was purified on silica gel column eluted with 0.3% ammonium hydroxide and 3% methanol in dichloromethane to give the desired product (12 mg, 46% yield).

$^1$H NMR (CDCl$_3$): δ 0.80-2.60 (m, 34 H) 2.98 (m, 1 H) 5.23 (m, 1 H) 5.71 (m, 1 H) MS: (M+H)$^+$=340

Example 131

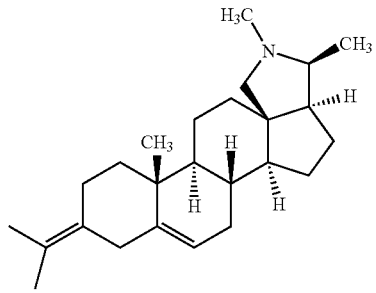

9-Isopropylidene-2,3,11a-trimethyl-2,3,3a,4,5,5a,5b,6,8,9,10,11,11a,11b,12,13-hexadecahydro-1H-2-aza-pentaleno[1,6a-a]phenanthrene The title compound was prepared according to procedures described in Example 130C, except substituting isopropyltriphenylphosphonium iodide for ethyl triphenylphosphonium bromide; MS: (M+H)$^+$=354.

Reference Example 132

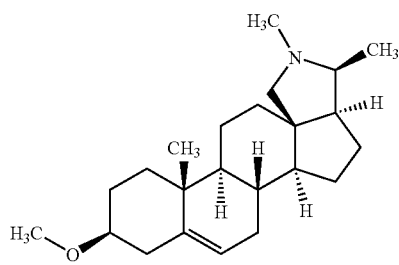

9-Methoxy-2,3,11a-trimethyl-2,3,3a,4,5,5a,5b,6,8,9,
10,11,11a,11b,12,13-hexadecahydro-1H-2-aza-pen-
taleno[1,6a-a]phenanthrene Compound 130A (30 mg, 0.091 mmol) was dissolved in 1.5 mL anhydrous DMF. Sodium hydride (60% dispersion in mineral oil, 6 mg, 0.137 mmol) was added and the mixture was stirred at room temperature for 1 hour before iodomethane (39 mg, 0.274 mmol) was added. The reaction mixture and stirred overnight, quenched with water and extracted with dichloromethane to give the crude product, which was purified on silica gel column eluted with 0.3% ammonium hydroxide and 5% methanol in dichloromethane to give the desired product (12 mg, 38% yield).

$^1$H NMR (CDCl$_3$): δ 0.95 (s, 3 H) 1.01-2.25 (m,263 H) 2.38 (m, 2 H) 3.05 (m, 2 H) 3.36 (s, 3 H) 5.37 (m, 1 H) MS: (M+H)$^+$=344

Example 133

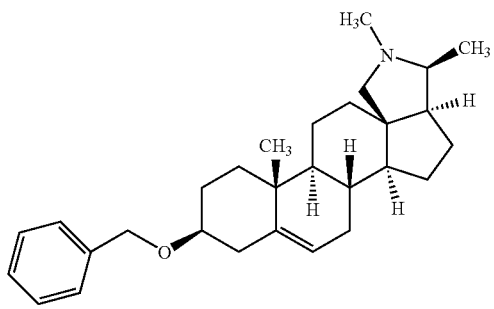

9-Benzyloxy-2,3,11a-trimethyl-2,3,3a,4,5,5a,5b,6,8,
9,10,11,11a,11b,12,13-hexadecahydro-1H-2-aza-
pentaleno[1,6a-a]phenanthrene The title compound was prepared according to procedures described in Reference Example 132, except substituting benzyl bromide for iodomethane. $^1$H NMR (CDCl$_3$): δ ppm 0.96 (s, 3 H) 1.04 (d, 3 H) 1.06-2.00 (m,18 H) 2.08 (m, 1 H) 2.20 (s. 3 H) 2.36 (m, 3 H) 2.99 (m, 1 H) 3.28 (m, 1 H) 4.55 (s, 2 H) 5.36 (m, 1 H) 7.25 (m, 2 H) 7.34 (m, 3 H); MS: (M+H)$^+$=420.

Example 134

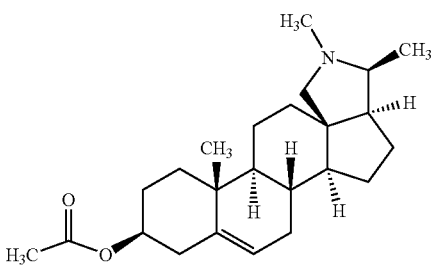

Acetic acid 2,3,11a-trimethyl-2,3,3a,4,5,5a,5b,6,8,9,
10,11,11a,11b,12,13-hexadecahydro-1H-2-aza-pen-
taleno[1,6a-a]phenanthren-9-yl ester Compound 130A (15 mg, 0.045 mmol) was dissolved in 1 mL anhydrous dichloromethane. Triethylamine (32 µL, 0.228 mmol) was added followed by acetyl chloride (6.5 µL, 0.09 mmol). The mixture was stirred at room temperature overnight. The crude product was purified on silica gel column eluted with 0.3% ammonium hydroxide and 3% methanol in dichloromethane to give the desired product (23 mg, 68% yield).

$^1$H NMR (CDCl$_3$): δ 0.96 (s, 3 H) 1.03-1.90 (m, 23 H) 2.04 (s, 3 H) 2.20-2.35 (m, 5 H) 2.98 (m, 1 H) 4.59 (m, 1 H) 5.39 m, 1 H) MS: (M+H)$^+$=372

Example 135

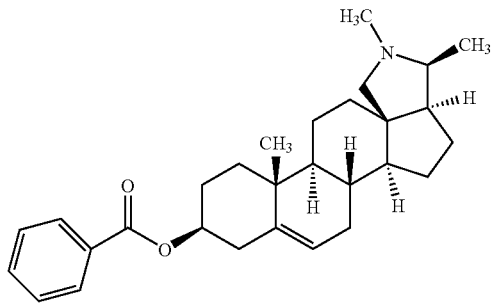

Benzoic acid 2,3,11a-trimethyl-2,3,3a,4,5,5a,5b,6,8,
9,10,11,11a,11b,12,13-hexadecahydro-1H-2-aza-
pentaleno[1,6a-a]phenanthren-9-yl ester The title compound was prepared according to procedures described in Example 134, except substituting benzoyl chloride for acetyl chloride. MS: (M+H)$^+$=434.

Example 136

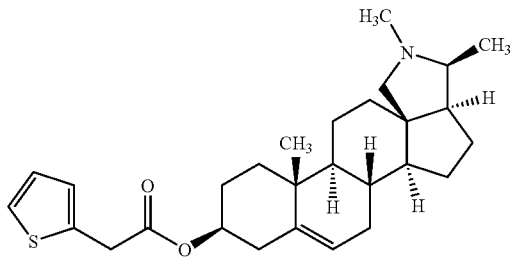

Thiophen-2-yl-acetic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 134, except substituting 2-thiopheneacetyl chloride for acetyl chloride. $^1$H NMR (CDCl$_3$): δ 0.90 (s, 3 H) 0.96 (d, J=3.73 Hz, 3 H) 1.00-2.40 (m, 27 H) 3.00 (m, 1 H) 4.66 (m, 1 H) 5.37 (m, 1 H) 6.94 (m, 2 H) 7.21 (m, 1 H); MS: (M+H)$^+$=454.

Example 137

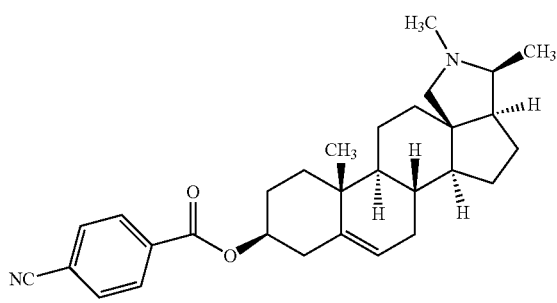

4-Cyano-benzoic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 134, except substituting 4-cyanobenzoyl chloride for acetyl chloride. $^1$H NMR (CDCl$_3$): δ 1.01 (s, 3 H) 1.04-2.30 (m, 25 H) 2.47 (d, 3 H) 3.00 (m, 1 H) 4.87 (m, 1 H) 5.44 (m, 1 H) 7.74 (m, 2 H) 8.14 (m, 2 H); MS: (M+H)$^+$=459.

Example 138

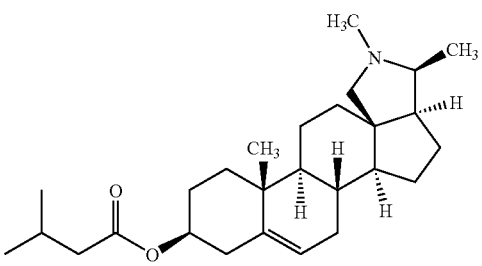

3-Methyl-butyric acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 134, except substituting isovaleryl chloride for acetyl chloride. $^1$H NMR (CDCl$_3$): δ 0.95 (d, 9 H) 1.00-2.35 (m, 31 H) 3.00 (m, 1 H) 4.62 (m, 1 H) 5.39 (m, 1 H); MS: (M+H)$^+$=414.

Example 139

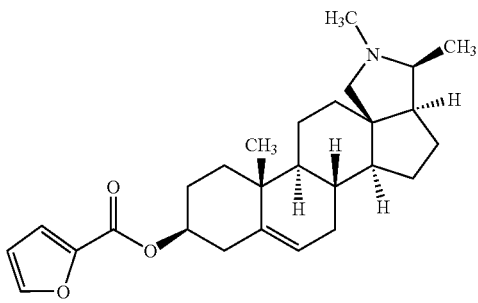

Furan-2-carboxylic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 134, except substituting 2-furoyl chloride for acetyl chloride. $^1$H NMR (CDCl$_3$): δ 1.00 (s, 3 H) 1.05-2.35 (m, 25 H) 2.45 (d, J=7.46 Hz, 3 H) 3.00 (m, 1 H) 4.84 (m, 1 H) 5.42 (m, 1 H) 6.50 (dd, J=3.39, 1.70 Hz, 1 H) 7.17 (d, J=4.41 Hz, 1 H) 7.57 (s, 1 H); MS: (M+H)$^+$32 424.

Example 140

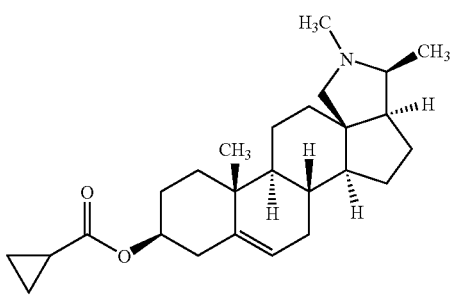

Cyclopropanecarboxylic acid 2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 134, except substituting cyclopropanecarbonyl chloride for acetyl chloride. $^1$H NMR (CDCl$_3$): δ 0.82-2.38 (m, 36 H) 3.01 (m, 1 H) 4.61 (m, 1 H) 5.38 (m, 1 H); MS: (M+H)$^+$398.

Example 141

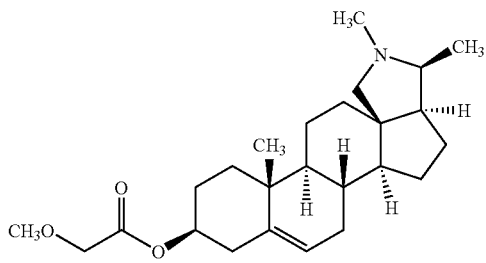

Methoxy-acetic acid 2,3,11a-trimethyl-2,3,3a,4,5,5a, 5b,6,8,9,10,11,11a,11b,12,13-hexadecahydro-1H-2-aza-pentaleno[1,6a-a]phenanthren-9-yl ester The title compound was prepared according to procedures described in Example 134, except substituting methoxy-acetyl chloride for acetyl chloride. $^1$H NMR (CDCl$_3$): δ 0.96 (s, 3 H) 1.00-2.30 (m, 25 H) 2.35 (d, J=7.46 Hz, 3 H) 3.01 (m, 1 H) 3.45 (s, 3 H) 4.01 (s, 2 H) 4.71 (m, 1 H) 5.40 (m, 1 H); MS: (M+H)$^+$=402.

Example 142

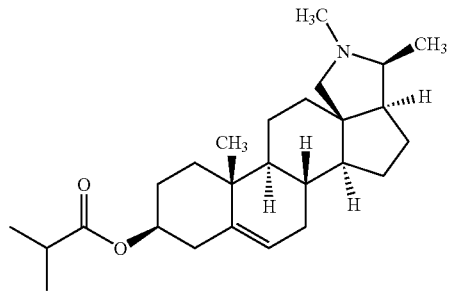

Isobutyric acid 2,3,11a-trimethyl-2,3,3a,4,5,5a,5b,6, 8,9,10,11,11a,11b,12,13-hexadecahydro-1H-2-aza-pentaleno[1,6a-a]phenanthren-9-yl ester The title compound was prepared according to procedures described in Example 134, except substituting isobutyryl chloride for acetyl chloride. $^1$H NMR (CDCl$_3$): δ 0.97 (s, 3 H) 1.15 (d, J=7.12 Hz, 6 H) 1.00-2.30 (m, 26 H) 2.32 (s, 3 H) 3.01 (m, 1 H) 4.63 (m, 1 H) 5.37 (m, 1 H); MS: (M+H)$^+$=400.

Example 143

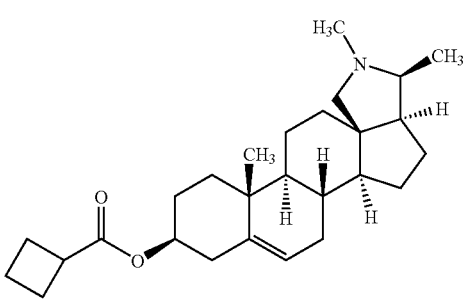

Cyclobutanecarboxylic acid 2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 134, except substituting cyclobutanecarbonyl chloride for acetyl chloride. $^1$H NMR (CDCl$_3$): δ 0.96 (s, 3 H) 1.00-2.35 (m, 35 H) 3.10 (m, 1 H) 4.61 (m, 1 H) 5.38 (m, 1 H); MS: (M+H)$^+$=412.

Example 144

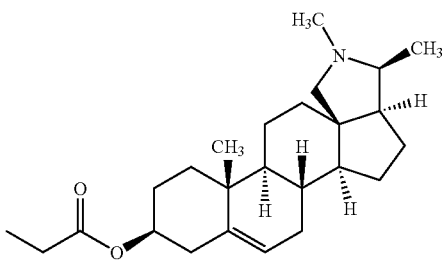

Propionic acid 2,3,11a-trimethyl-2,3,3a,4,5,5a,5b,6, 8,9,10,11,11a,11b,12,13-hexadecahydro-1H-2-aza-pentaleno[1,6a-a]phenanthren-9-yl ester The title compound was prepared according to procedures described in Example 134, except substituting propionyl chloride for acetyl chloride. $^1$H NMR (CDCl$_3$): δ 0.96 (s, 3 H) 1.08-2.38 (m, 33 H) 3.59 (m, 1 H) 4.61 (m, 1 H) 5.38 (m, 1 H); MS: (M+H)$^+$=386.

Example 145

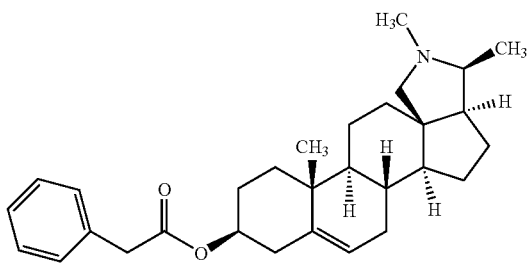

Phenyl-acetic acid 2,3,11a-trimethyl-2,3,3a,4,5,5a,
5b,6,8,9,10,11,11a,11b,12,13-hexadecahydro-1H-2-
aza-pentaleno[1,6a-a]phenanthren-9-yl ester The title compound was prepared according to procedures described in Example 134, except substituting phenylacetyl chloride for acetyl chloride. MS: $(M+H)^+=448$.

Example 146

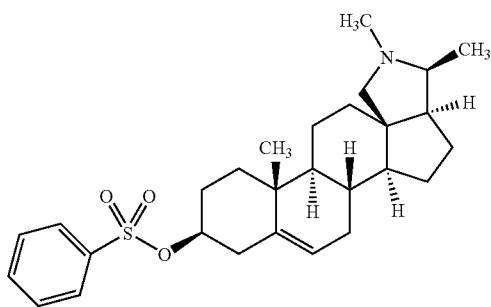

Benzenesulfonic acid 2,3,1a-trimethyl-2,3,3a,4,5,5a,
5b,6,8,9,10,11,11a,11b,12,13-hexadecahydro-1H-2-
aza-pentaleno[1,6a-a]phenanthren-9-yl ester The title compound was prepared according to procedures described in Example 134, except substituting benzenesulfonyl chloride for acetyl chloride. $^1$H NMR (CDCl$_3$): δ 0.92 (m, 3 H) 1.05-2.50 (m, 28 H) 2.94 (m, 1 H) 4.37 (m, 1 H) 5.31 (m, 1 H) 7.54 (m, 2 H) 7.63 (m, 1 H) 7.92 (m, 2 H); MS: $(M+H)^+=470$.

Example 147

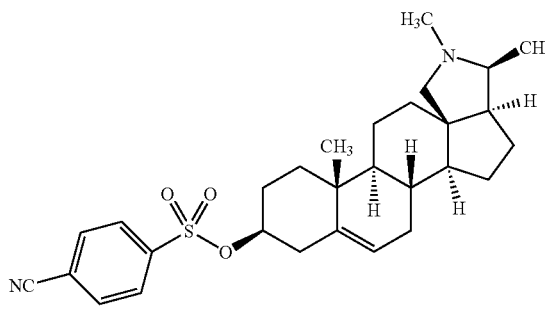

4-Cyano-benzenesulfonic acid 2,3,11a-trimethyl-2,
3,3a,4,5,5a,5b,6,8,9,10,11,11a,11b,12,13-hexa-
decahydro-1H-2-aza-pentaleno[1,6a-a]phenanthren-
9-yl ester The title compound was prepared according to procedures described in Example 134, except substituting 4-cyanobenzenesulfonyl chloride for acetyl chloride. $^1$H NMR (CDCl$_3$): δ 0.92 (m, 3 H) 1.05-2.50 (m, 28 H) 2.94 (m, 1 H) 4.37 (m, 1 H) 5.38 (m, 1 H) 7.85 (m, 2 H) 8.02 (m, 2 H); MS: $(M+H)^+=495$.

Example 148

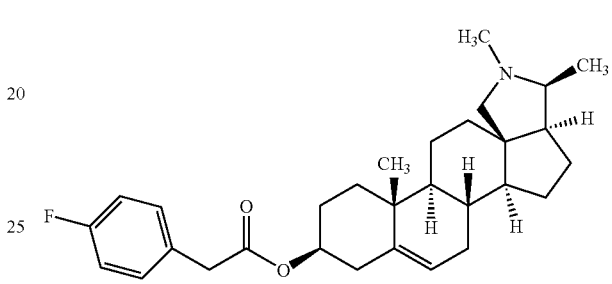

(4-Fluoro-phenyl)-acetic acid 2,3,11a-trimethyl-2,3,
3a,4,5,5a,5b,6,8,9,10,11,11a,11b,12,13-hexadecahy-
dro-1H-2-aza-pentaleno[1,6a-a]phenanthren-9-yl
ester A mixture of compound 130A (20 mg, 0.06 mmol), 4-fluorophenylacetic acid (14 mg, 0.09 mmol), 1,3-dicyclohexylcarbodiimide (25 mg, 0.12 mmol), 4(dimethylamino) pyridine (2 mg, 0.016 mmol) and THF (1 mL) was stirred at room temperature overnight. The crude reaction mixture was loaded directly onto silica gel column and eluted with 0.2% ammonium hydroxide and 2% methanol in dichloromethane to give the pure desired product (25 mg, 87% yield).

$^1$H NMR (CDCl$_3$): δ 0.96 (s, 3H) 1.08-2.38 (m, 27 H) 3.01 (s, 2H) 3.45 (m, 1H) 4.00 (m, 1H),4.60 (m, 1H) 5.37 (m,1H) 7.01 (m,2H) 7.23 (m, 2H) MS: $(M+H)^+=466$

Example 149

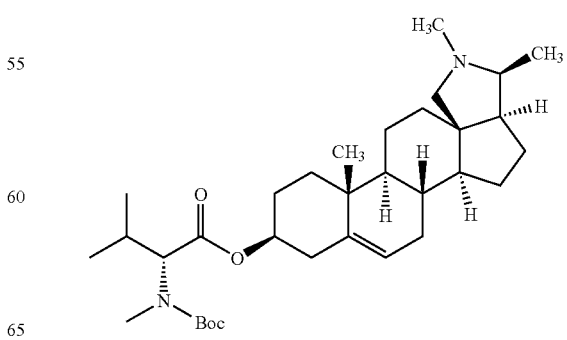

2-(tert-Butoxycarbonyl-methyl-amino)-3-methyl-butyric acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting Boc-N-methyl-D-valine for 4-fluorophenylacetic acid. MS: (M+H)$^+$=543.

Example 150

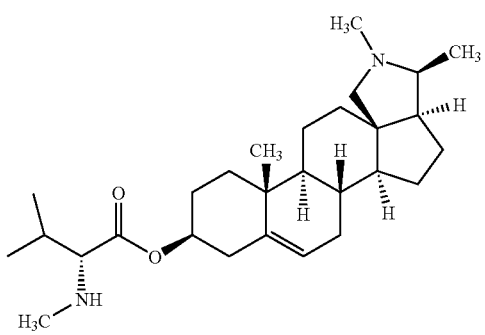

3-Methyl-2-methylamino-butyric acid-2,3,11a-trimethyl-2,3,3a,4,5,5a,5b,6,8,9,10,11,11a,11b,12,13-hexadecahydro-1 H-2-aza-pentaleno[1,6, a-a]phenanthren-9-yl ester Compound 149 (10 mg, 0.018 mmol) was stirred with 1:1 mixture of TFA and dichloromethane (1 mL) for 2 h. Solvent was evaporated under reduced pressure, and the residue was triturated with ethyl acetate twice and dried on high vacuum to give the desired product.
MS: (M+H)$^+$=443

Example 151

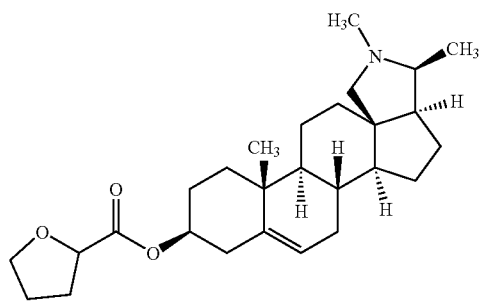

Tetrahydro-furan-2-carboxylic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting tetrahydro2-furoic acid for 4-fluorophenylacetic acid. $^1$H NMR (CDCl$_3$):

δ 0.96 (s, 3 H) 1.00-2.60 (m, 30 H) 3.01 (s, 3 H) 3.95 (m, 2 H) 4.42 (m, 1 H) 4.67 (m, 1 H) 5.38 (m, 1 H); MS: (M+H)$^+$=427.

Example 152

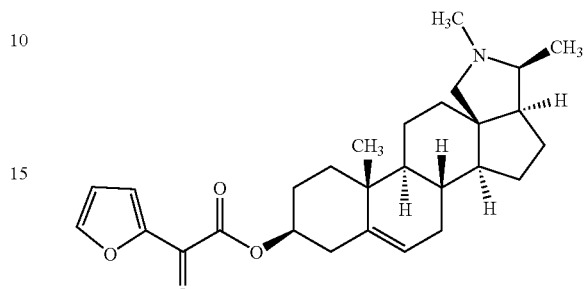

Furan-2-yl-oxo-acetic acid 2,3,11a-trimethyl-2,3,3a,4,5,5a,5b,6,8,9,10,11,11a,11b,12,13-hexadecahydro-1-H-2-aza-pentaleno[1,6a-a]phenanthren-9-yl ester The title compound was prepared according to procedures described in Example 148, except substituting 2-oxo-2-furanylacetic acid for 4-fluorophenylacetic acid. $^1$H NMR (CDCl$_3$): δ 1.00 (s, 3 H) 1.05-2.60 (m, 26 H) 3.02 (s, 3 H) 4.87 (m, 1 H) 5.43 (m, 1 H) 6.62 (dd, J=3.73, 1.70 Hz, 1 H) 7.69 (d, J=3.05 Hz, 1 H) 7.75 (s, 1 H); MS: (M+H)$^+$=452.

Example 153

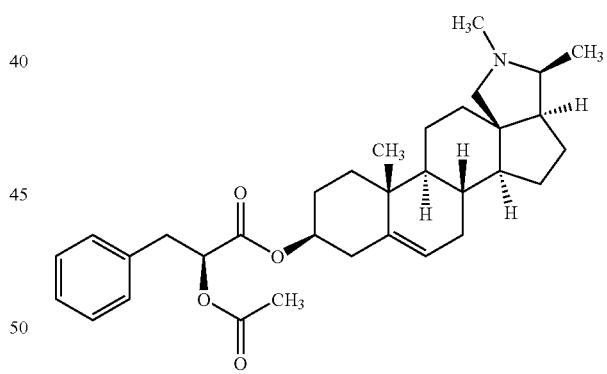

2-Acetoxy-3-phenyl-propionic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting L-2-acetoxy-3-phenylpropionic acid for 4-fluorophenylacetic acid and the corresponding carboxylic acid was prepared according to the procedure used in Example 91. $^1$H NMR (CDCl$_3$): δ 0.96 (s, 3 H) 1.08-2.40 (m, 29 H) 2.09 (s, 3 H) 3.11 (m, 2 H) 4.62 (m, 1 H) 5.15 (dd, J=8.14, 5.09 Hz, 1 H) 5.36 (m, 1 H) 7.29 (m, 5 H); MS: (M+H)$^+$=520, (M+NH$_4$)$^+$=537.

Example 154

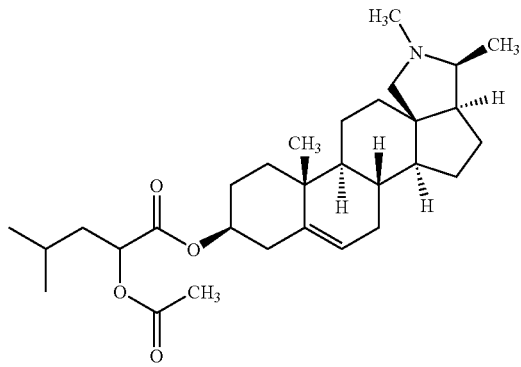

2-Acetoxy-4-methyl-pentanoic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 2-acetoxy-isocaproic acid for 4-fluorophenylacetic acid and the corresponding carboxylic acid was prepared according to the procedure used in Example 91. $^1$H NMR (CDCl$_3$): δ 0.95 (m, 9 H) 1.00-2.00 (m, 28 H) 2.13 (s, 3 H) 2.33 (m, 3 H) 2.78 (m, 1 H) 4.64 (m, 1 H) 4.96 (m, 1 H) 5.38 (m, 1 H); MS: (M+H)$^+$=486.

Example 155

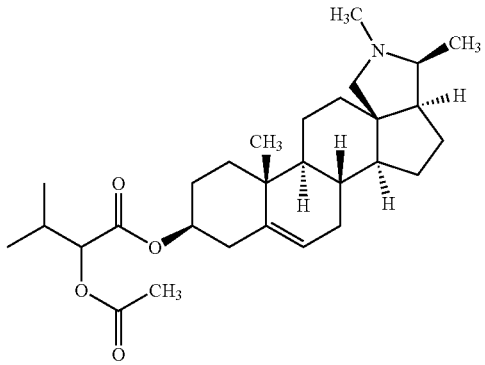

2-Acetoxy-3-methyl-butyric acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 2-acetoxy-3-methylbutyric acid for 4-fluorophenylacetic acid and the corresponding carboxylic acid was prepared according to the procedure used in Example 91. $^1$H NMR (CDCl$_3$): δ 0.99 (m, 12 H) 1.10-2.05 (m, 22 H) 2.14 (s, 3 H) 2.26 (m, 5 H) 4.68 (m, 1 H) 4.78 (d, J=4.75 Hz, 1 H) 5.39 (m, 1 H); MS: (M+H)$^+$=472.

Example 156

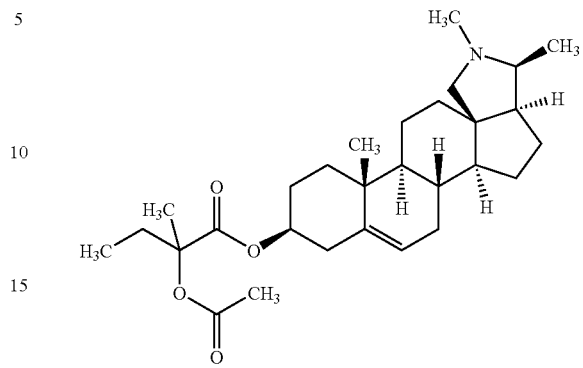

2-Acetoxy-2-methyl-butyric acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 2-hydroxy-2-methylbutyric acid for 4-fluorophenylacetic acid and the corresponding carboxylic acid was prepared according to the procedure used in Example 91. $^1$H NMR (CDCl$_3$): δ 0.92 (m, 9 H) 1.10-1.95 (m, 26 H) 2.03 (d, 3 H) 2.31 (m, 3 H) 2.52 (m, 2 H) 4.62 (m, 1 H) 5.38 (m, 1 H); MS: (M+H)$^+$=472.

Example 157

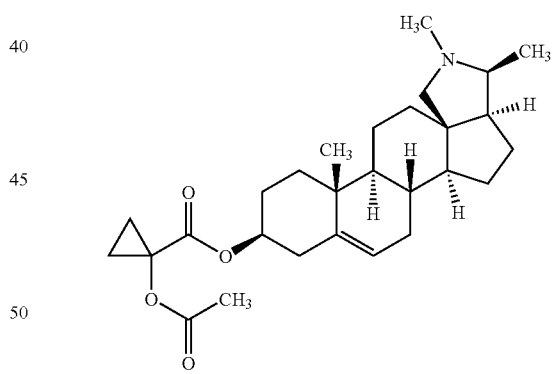

1-Acetoxy-cyclopropanecarboxylic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 1-acetoxy-1cyclopropanecarboxylic acid for 4-fluorophenylacetic acid and the corresponding carboxylic acid was prepared according to the procedure used in Example 91. $^1$H NMR (CDCl$_3$): δ 0.93 (s, 3 H) 1.15-1.90 (m, 27 H) 2.10 (s, 3 H) 2.15-2.90 (m, 6 H) 4.61 (m, 1 H) 5.37 (m, 1 H); MS: (M+H)$^+$=456.

Example 158

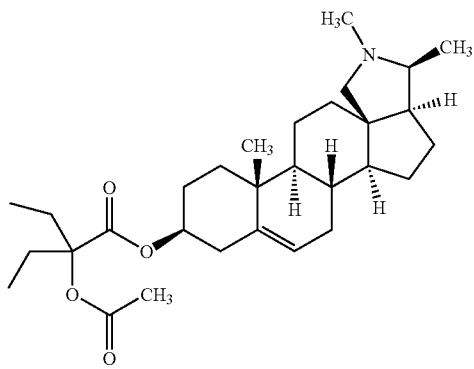

2-Acetoxy-2-ethyl-butyric acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 2-ethyl-2-acetoxybutyric acid for 4-fluorophenylacetic acid and the corresponding carboxylic acid was prepared according to the procedure used in Example 91. $^1$H NMR (CDCl$_3$): δ 0.85 (t, J=7.46 Hz, 6 H) 0.96 (s, 3 H) 1.00-2.00 (m, 27 H) 2.07 (s, 3 H) 2.10-2.35 (m, 6 H) 4.65 (m, 1 H) 5.38 (m, 1 H); MS: (M+H)$^+$=486.

Example 159

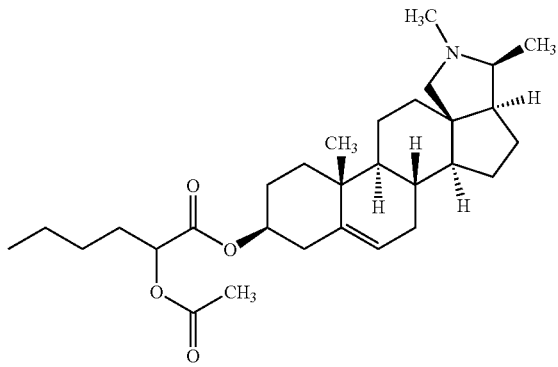

2-Acetoxy-hexanoic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 2-acetoxycaproic acid for 4-fluorophenylacetic acid and the corresponding carboxylic acid was prepared according to the procedure used in Example 91. $^1$H NMR (CDCl$_3$): δ 0.93 (m, 9 H) 1.00-2.00 (m, 26 H) 2.13 (s, 3 H) 2.34 (m, 6 H) 4.66 (m, 1 H) 4.93 (t, J=6.44 Hz, 1 H) 5.39 (m, 1 H); MS: (M+H)$^+$=503.

Example 160

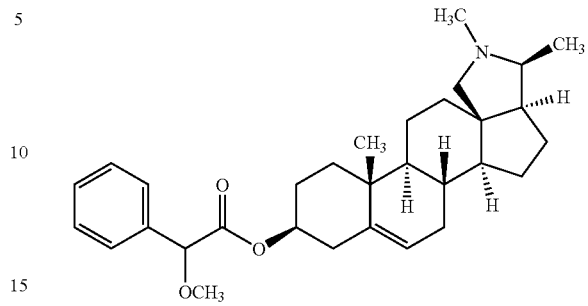

Methoxy-phenyl-acetic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 148, except substituting 2-methoxyphenylacetic acid for 4-fluorophenylacetic acid. $^1$H NMR (CDCl$_3$): δ 0.93 (s, 3 H) 1.00-2.30 (m, 27 H) 2.33 (d, J=7.80 Hz, 3 H) 3.41 (s, 3 H) 4.68 (m, 1 H) 5.35 (m, 1 H) 7.36 (m, 3 H) 7.44 (m, 2 H); MS: (M+H)$^+$=478, (M+NH$_4$)$^+$=495.

Example 161

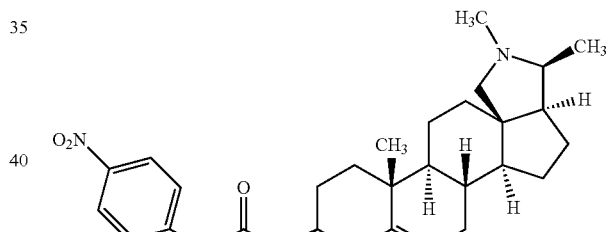

Carbonic acid 4-nitro-phenyl ester 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester Compound 130A (250 mg, 0.76 mmol) was dissolved in 10 mL dichloromethane and cooled to 0° C. 4-Nitrophenylchloroformate (170 mg, 0.84 mmol) was added followed by N-methylmorpholine (125 μL, 1.14 mmol). The mixture was stirred overnight while warmed up slowly to room temperature. TLC indicated that the reaction was not completed. 4-Nitrophenylchloroformate (309 mg, 1.52 mmol) and N-methylmorpholine (250 μL, 2.28 mmol) were added and stirred at room temperature for 3 hours. Reaction was complete. It was loaded on silica gel column and eluted with 0.5% ammonium hydroxide and 5% methanol in dichloromethane to give the paranitrophenolcarbonate (PNP-carbonate, 260 mg, 69% yield).

$^1$H NMR (CDCl$_3$): δ 0.98 (s, 3 H) 1.05-2.60 (m, 26 H) 2.79 (m, 2 H) 3.69 (m, 1 H) 4.60 (m, 1 H) 5.45 (m, 1 H) 7.39 (m, 2 H) 8.28 (m, 2 H) MS: (M+H)$^+$=495

Example 162

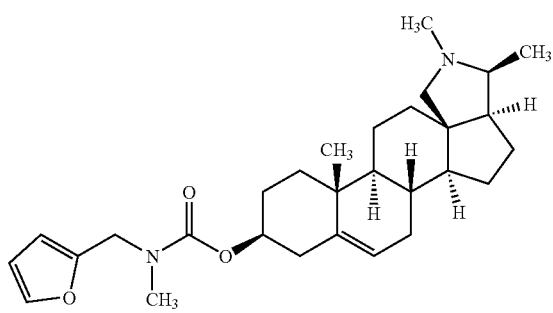

Furan-2-ylmethyl-methyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester Compound 161 (25 mg, 0.051 mmol), N-methylfurylamine (7 µL, 0.061 mmol), dichloromethane (0.5 mL) and THF (1 mL) were mixed and stirred at room temperature overnight. The crude reaction mixture was purified on silica gel column, which was eluted with 0.3% ammonium hydroxide and 3% methanol in dichloromethane to give the desired product (21 mg, 87% yield).
MS: $(M+H)^+$=467

Example 163

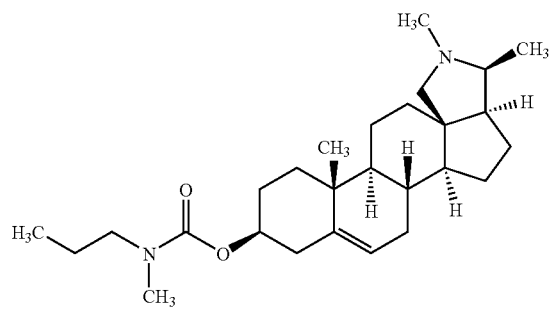

Methyl-propyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting methylpropylamine for N-methylfurylamine. MS: $(M+H)^+$=429.

Example 164

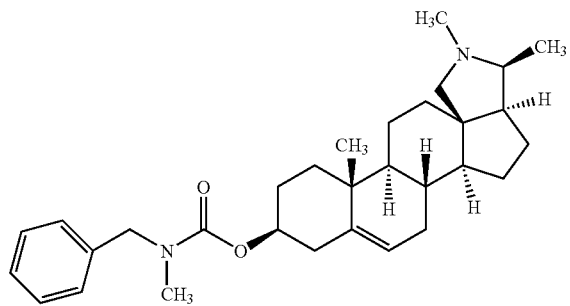

Benzyl-methyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting N-benzylmethylamine for N-methylfurylamine. $^1$H NMR (CDCl$_3$): δ 0.96 (s, 3 H) 1.04-2.42 (m, 27H) 2.87 (m, 4 H) 2.95 (m, 1 H) 4.46 (s, 2 H) 4.57 (m, 1 H) 5.40 (m, 1 H) 7.29 (m, 5 H); MS: $(M+H)^+$=477, $(M+NH_4)^+$494.

Example 165

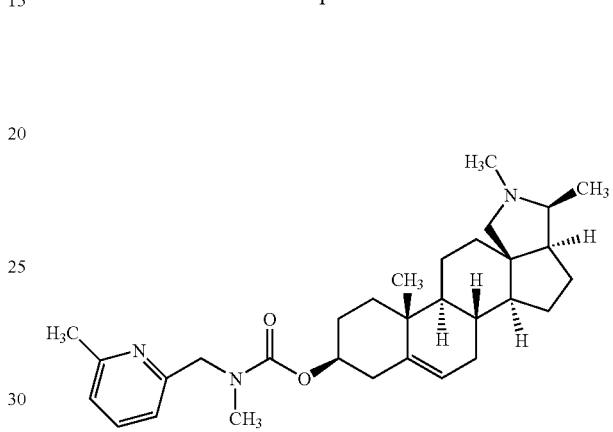

Methyl-(6-methyl-pyridin-2-ylmethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting 6-methyl-2-picolymethylamine for N-methylfurylamine. $^1$H NMR (CDCl$_3$): δ 0.91 (s, 3 H) 0.98 (s, 3 H) 1.15-2.45 (m, 26 H) 2.54 (s, 3 H) 2.97 (m, 4 H) 4.56 (m, 2 H) 5.38 (m, 1 H) 7.03 (m, 2 H) 7.55 (m, 1 H); MS: $(M+H)^+$=492.

Example 166

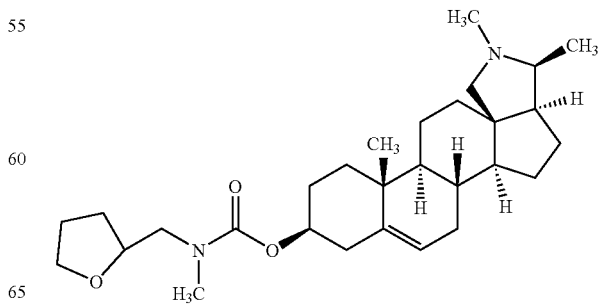

Methyl-(tetrahydro-furan-2-ylmethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting N-methyltetrahydrofurfurylamine for N-methylfurylamine. $^1$H NMR (CDCl$_3$): δ 0.96 (s, 3 H) 1.03-2.40 (m, 33 H) 2.97 (s, 3 H) 3.10-3.60 (m, 2 H) 3.79 (m, 2 H) 4.05 (m, 1 H) 4.51 (m, 1 H) 5.38 (m, 1 H); MS: (M+H)$^+$=471.

Example 167

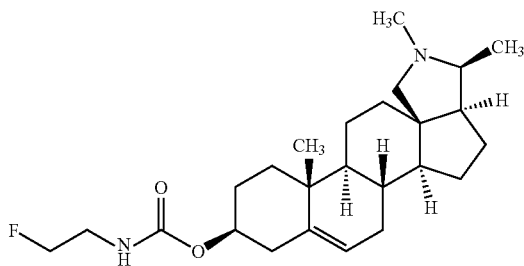

(2-Fluoro-ethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting 2-fluoroethylaminehydrochloride for N-methylfurylamine. $^1$H NMR (CDCl$_3$): δ 0.96 (s, 3 H) 1.00-1.95 (m, 38 H) 2.05-2.40 (m, 8 H) 3.43 (m, 1 H) 3.53 (m, 1 H) 4.41 (t, J=4.75 Hz, 2 H) 4.50 (m, 1 H) 4.57 (t, J=4.75 Hz, 2 H) 4.93 (m, 1 H) 5.39 (m, 1 H); MS: (M+H)$^+$=419, (M+NH$_4$)$^+$=436.

Example 168

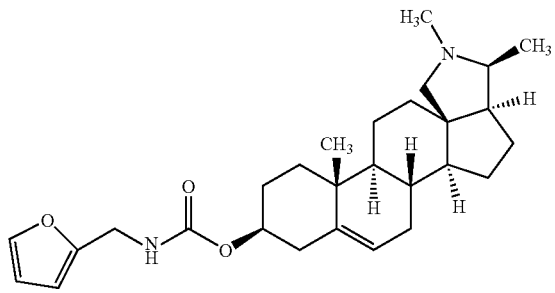

Furan-2-ylmethyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting furfurylamine for N-methylfurylamine. $^1$H NMR (CDCl$_3$): δ 0.95 (s, 3 H) 1.00-2.40 (m, 28 H) 3.02 (m, 1 H) 4.34 (d, J=5.43 Hz, 2 H) 4.52 (m, 1H) 4.90 (m, 1 H) 5.39 (m, 1 H) 6.22 (d, J=2.71 Hz, 1 H) 6.31 (dd, J=3.22, 1.86 Hz, 1 H) 7.35 (s, 1 H); MS: (M+H)$^+$=453.

Example 169

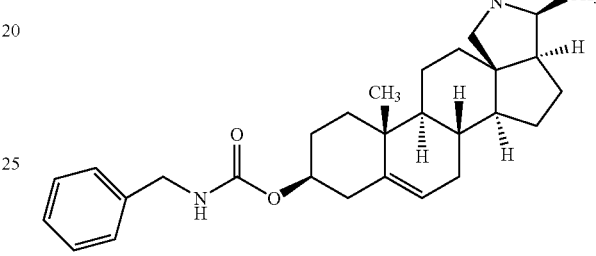

(2-Cyano-ethyl)-(tetrahydro-furan-2-ylmethyl)-carbamic acid 2,3,11a-trimethyl-2,3,3a,4,5,5a,5b,6,8,9,10, 11,11a,11b,12,13-hexadecahydro-1H-2-aza-pentaleno[1,6a-a]phenanthren-9-yl ester The title compound was prepared according to procedures described in Example 162, except substituting 3-[(tetrahydrofuran-2-ylmethyl)amino]propane nitrile for N-methylfurylamine. $^1$H NMR (CDCl$_3$): ε 0.95 (s, 3 H) 1.00-2.40 (m, 34 H) 2.71 (m, 2 H) 3.60 (m, 2 H) 3.73 (m, 2 H) 3.85 (m, 1 H) 4.01 (m, 1 H) 4.54 (m, 1 H) 5.38 (m, 1 H); MS: (M+H)$^+$=510.

Example 170

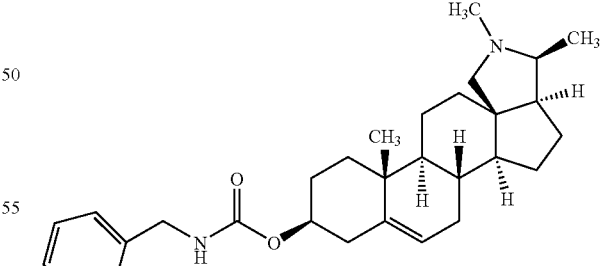

Benzyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting benzylamine for N-methylfurylamine. MS: (M+H)$^+$=451.

Example 171

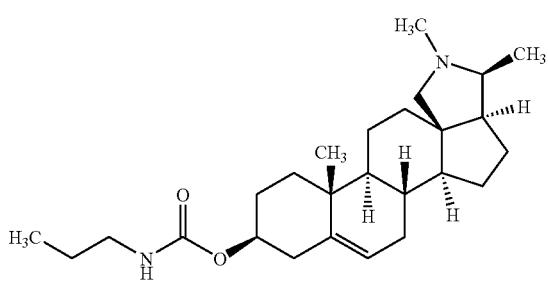

Propyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester The title compound was prepared according to procedures described in Example 162, except substituting propylamine for N-methylfurylamine. MS: (M+H)$^+$=403.

Reference Example 172

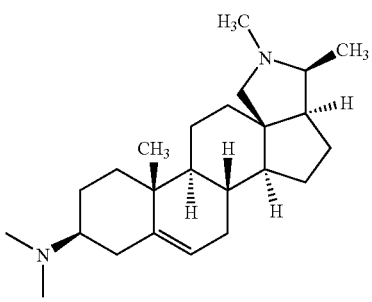

172A. Dimethyl-(2,3,11a-trimethyoctadecahydro-2-aza-pentaleno[1,6a-a]phenanthren-9-yl)-amine Conessine (50 mg, 0.14 mmol) was dissolved in 3 mL ethyl acetate and 10% Pd/C (20 mg) was added under inert atmosphere. The reaction mixture was hydrogenated under a hydrogen balloon for 24 hours. Reaction was not complete by TLC. The reaction mixture was filtered through diatomaceous earth, washed with ethyl acetate, and the filtrate was concentrated to give the crude product which was purified by silica gel column eluted with 0.3% ammonium hydroxide and 3% methanol in dichloromethane to give the desired product (15 mg, 30% yield).

$^1$H NMR (CDCl$_3$): δ 0.74 (s, 3 H) 0.95-2.00 (m, 29 H) 2.32 (s, 3 H) 2.43 (s, 6 H) 3.12 (m, 1 H) MS: (M+H)$^+$=359

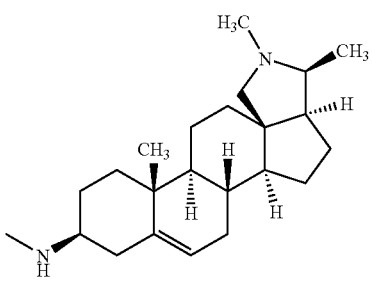

172B. Methyl-2,3,11a-trimethyl-octadecahydro-2-aza-pentaleno[1,6a-a]phenanthren-9-yl)-amine The title compound was prepared using the procedures described in Example 7A and 7B, except substituting Compound 172A for connessine. $^1$H NMR (CDCl$_3$): δ 0.75 (s, 3 H) 0.90-2.00 (m, 25 H) 2.29 (m, 3 H) 2.51 (s, 3 H) 2.62 (m, 1 H) 2.93 (s, 3 H) 3.09 (m, 1 H) 4.13 (m, 1 H); (M+H)$^+$=345.

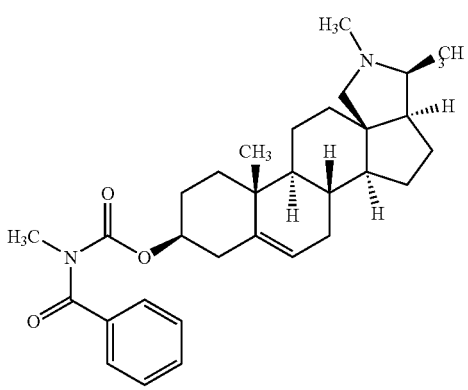

172C. N-Methyl-N-(2,3,11a-trimethyoctadecahydro-2-aza-pentaleno[1,6a-a]phenanthren-9-yl)-benzamide The title compound was prepared according to procedures described in Example 7C, except substituting Compound 172B for Compound 7B and benzoyl chloride for acetyl chloride. $^1$H NMR (CDCl$_3$): δ 0.75 (s, 3 H) 0.85-2.00 (m, 26 H) 2.21 (m, 3 H) 2.80 (s, 3 H) 2.98 (s, 3 H) 3.46 (m, 1 H) 7.39 (m, 5 H); (M+H)$^+$=449.

Example 173

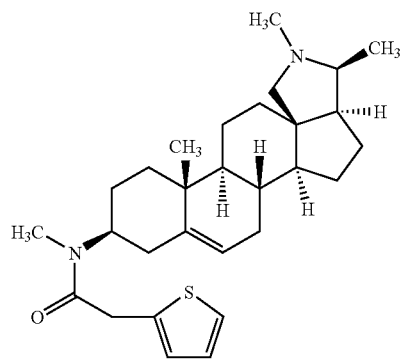

N-Methyl-2-thiophen-2-yl-N-(2,3,11a-trimethyl-octadecahydro-2-aza-pentaleno[1,6a-a]phenanthren-9-yl)-acetamide The title compound was prepared according to procedures described in Example 7C, except substituting Compound 172B for Compound 7B and 2-thiopheneacetyl chloride for acetyl chloride. $^1$H NMR (CDCl$_3$): δ 0.74 (s, 3 H) 0.95-2.40 (m, 27 H) 2.83 (s, 3 H) 2.88 (s, 3 H) 3.01 (m, 1 H) 3.69 (m, 1 H) 3.90 (d, J=11.53 Hz, 2 H) 4.49 (m, 1 H) 6.92 (m, 2 H) 7.19 (m, 1 H); (M+H)$^+$=469.

Example 174

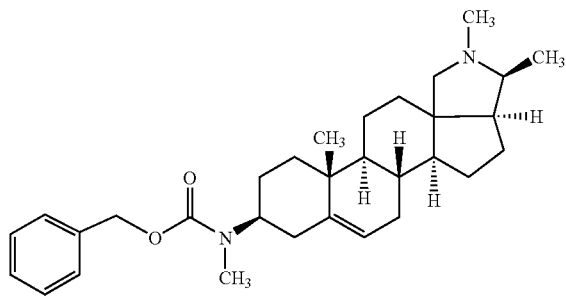

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid benzyl ester Compound 7B (20 mg, 0.058 mmol) and triethylamine (9.1 µL, 0.064 mmol) were dissolved in dichloromethane (1 mL). Benzyl chloroformate was added to it. The mixture was stirred at room temperature for 2 hours. The crude reaction mixture was purified on silica gel column using 0.5% ammonium hydroxide and 5% methanol in dichloromethane to give the desired product (18.4 mg, 66.2% yield).

$^1$H NMR (CDCl$_3$): δ ppm 0.94 (s, 3 H) 0.98-1.90 (m, 21 H) 2.02 (m, 2 H) 2.21 (s, 3 H) 2.43 (m, 2 H) 2.84 (s, 3 H) 2.98 (m, 1 H) 3.89 (m, 1 H) 5.14 (s, 2 H) 5.35 (d, J=5.09 Hz, 1 H) 7.32 (m, 5 H); MS: (M+H)$^+$=477.

Example 175

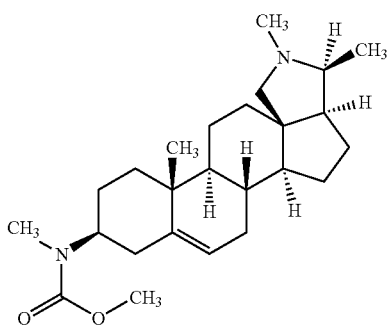

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9yl)-carbamic acid methyl ester The title compound was prepared according to procedures described in Example 174, except substituting methyl chloroformate for benzyl chloroformate. MS: (M+H)$^+$=401.

Example 176

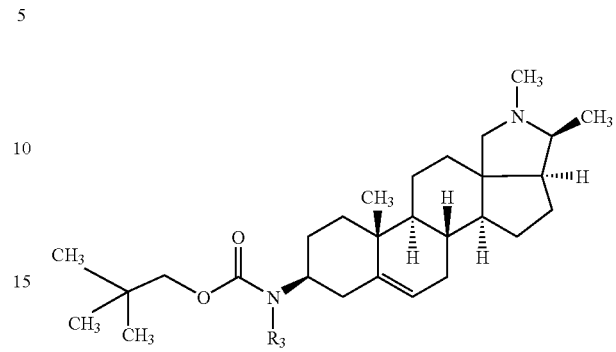

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 2,2-dimethyl-propyl ester The title compound was prepared according to procedures described in Example 174, except substituting neopentyl chloroformate for benzyl chloroformate. $^1$H NMR (CDCl$_3$): δ 0.95 (s, 3H) 0.96 (s, 9 H) 0.98-1.70 (m, 17 H) 1.78 (td, 2 H) 1.90 (m, 2 H) 2.05 (td, 2 H) 2.26 (s, 3 H) 2.43 (td, 2 H) 2.83 (s, 3 H) 3.04 (m, 1 H) 3.77 (s, 2 H) 3.92 (m, 1 H) 5.35 (d, J=5.09 Hz, 1 H); MS: (M+H)$^+$=457.

Example 177

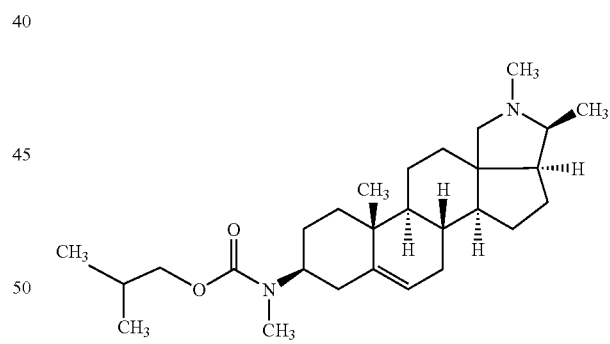

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid isobutyl ester The title compound was prepared according to procedures described in Example 174, except substituting isobutyl chloroformate for benzyl chloroformate. $^1$H NMR (CDCl$_3$): δ 0.94 (d, J=6.78 Hz, 6 H) 0.95 (s, 3H) 1.01-2.10 (m, 24 H) 2.24 (s, 3 H) 2.42 (m, 2 H) 2.82 (s, 3 H) 3.01 (m, 1 H) 3.86 (d, J=6.44 Hz, 2 H) 3.94 (m, 1 H) 5.35 (d, J=5.10 Hz, 1 H); MS: (M+H)$^+$=443.

Example 178

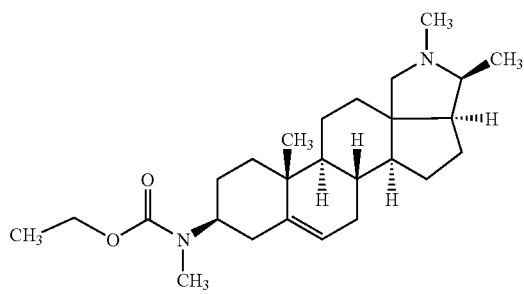

Methyl-(2,3,11a-trimethyl-2,3,3a,4,5,5a,5b,6,8,9,10,1,11a,11b,12,13-hexadecahydro-1H-2-aza-pentaleno[1,6a-a]phenanthren-9-yl)-carbamic acid ethyl ester The title compound was prepared according to procedures described in Example 174, except substituting ethyl chloroformate for benzyl chloroformate. $^1$H NMR (CDCl$_3$): δ 0.95 (s, 3 H) 1.26 (t, J=7.12 Hz, 3 H) 0.97-1.91 (m, 21 H) 2.02 (m, 2 H) 2.19 (s, 3 H) 2.41 (td, 2 H) 2.81 (s, 3 H) 3.00 (m, 1 H) 3.86 (m, 1 H) 4.13 (q, J=7.12 Hz, 2 H) 5.36 (d, J=5.09 Hz, 1 H); MS: (M+H)$^+$=415.

Example 179

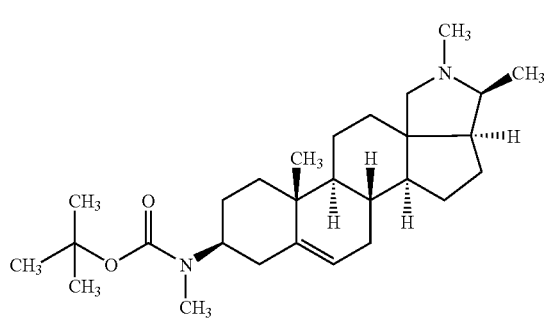

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid tert-butyl ester The title compound was prepared according to procedures described in Example 174, except substituting tertbutyl chloroformate for benzyl chloroformate. $^1$H NMR (CDCl$_3$): δ 0.94 (s, 3 H) 1.04 (d, J=6.10 Hz, 3 H) 1.46 (s, 9 H) 1.54 (s, 3 H) 1.10-1.89 (m, 15 H) 2.02 (m, 2 H) 2.21 (s, 3 H) 2.36 (m, 2 H) 2.76 (s, 3 H) 2.99 (d,J=10.51 Hz, 1 H) 3.83 (m, 1 H) 5.35 (d, J=5.42 Hz, 1 H); MS: (M+H)$^+$=443.

Example 180

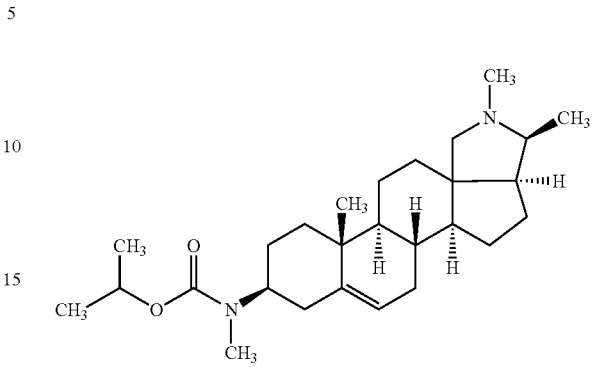

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid isopropyl ester The title compound was prepared according to procedures described in Example 174, except substituting isopropyl chloroformate for benzyl chloroformate. $^1$H NMR (CDCl$_3$): δ 0.95 (s, 3 H) 1.24 (d, J=6.44 Hz, 6 H) 1.79 (m, 23 H) 2.22 (s, 3 H) 2.41 (m, 2 H) 2.80 (s, 3 H) 2.99 (m, 1 H) 3.88 (m, 1 H) 4.92 (m, 1 H) 5.35 (d, J=3.00 Hz, 1 H); MS: (M+H)$^+$=429.

Example 181

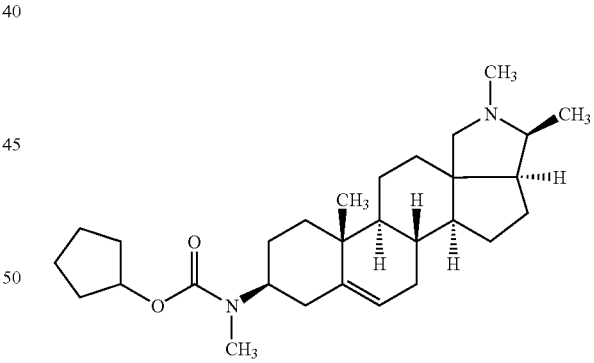

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid cyclopentyl ester The title compound was prepared according to procedures described in Example 174, except substituting cyclopentyl chloroformate for benzyl, chloroformate. $^1$H NMR (CDCl$_3$): δ 0.94 (s, 3 H) 1.54 (m, 29 H) 2.00 (m, 2 H) 2.22 (s, 3 H) 2.41 (m, 2 H) 2.79 (s, 3 H) 3.00 (m, 1 H) 3.81 (m, 1 H) 5.11 (m, 1 H) 5.35 (d, J=5.42 Hz, 1 H); MS: (M+H)$^+$=455.

Example 182

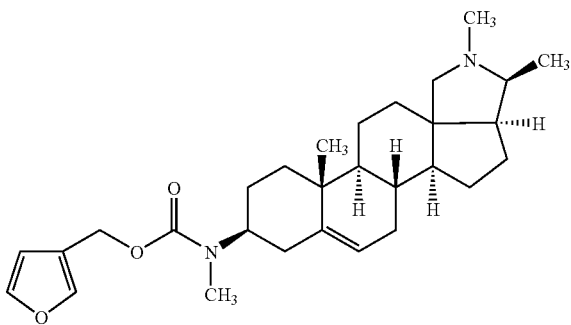

Methyl-(2,3,11a-trimethyl-2,3,3a,4,5,5a,5b,6,8,9,10,
11,11a,11b,12,13-hexadecahydro-1H-2-aza-pentaleno[1,6a-a]phenanthren-9-yl)-carbamic acid furan-3-ylmethyl ester Compound 7B (10 mg, 0.029 mmol), carbonic acid furan-3-ylmethyl ester 4-nitro-phenyl ester (2.4 mg, 0.032 mmol) and triethylamine (12.0 µL, 0.087 mmol) were dissolved in THF (1 mL) and stirred at room temperature overnight. The crude reaction mixture was purified on silica gel column using 0.5% ammonium hydroxide and 5% methanol in dichloromethane to give the desired product (10.1 mg, 74.2% yield).

$^1$H NMR (CDCl$_3$): δ 0.94 (s, 3 H) 1.04-2.04 (m, 23 H) 2.24 (s, 3 H) 2.42 (m, 2 H) 2.81 (s, 3 H) 3.03 (m, 1 H) 3.85 (m, 1 H) 4.99 (s, 2 H) 5.35 (d, J=5.09 Hz, 6.43 s, 1 H) 7.39 (t, J=1.70 Hz, 1 H) 7.46 (s, 1 H); MS: (M+H)$^+$=467.

Example 183

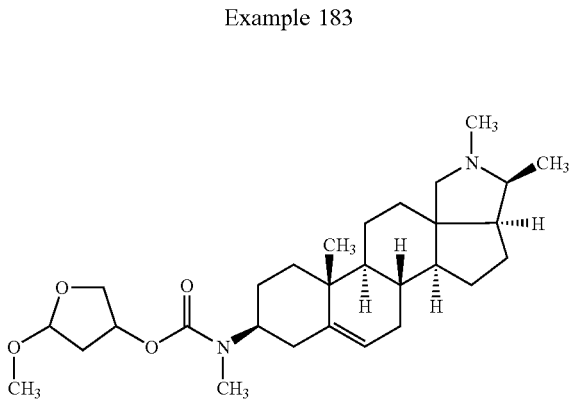

Methyl-(2,3,1a-trimethyl-2,3,3a,4,5,5a,5b,6,8,9,10,
11,11a,11b,12,13-hexadecahydro-1H-2-aza-pentaleno[1,6a-a]phenanthren-9-yl)-carbamic acid 5-methoxy-tetrahydro-furan-3-yl ester The title compound was prepared according to procedures described in Example 182, except substituting carbonic acid 5methoxy-tetrahydro-furan-3-yl ester 4-nitro-phenyl ester for carbonic acid furan-3-ylmethyl ester 4-nitro-phenyl ester. $^1$H NMR (CDCl$_3$): δ 0.95 (m, 3 H) 0.99-2.04 (m, 25 H) 2.22 (s, 3 H) 2.40 (t,J=11.53 Hz, 2 H) 2.78 (s, 3 H) 2.98 (d, J=2.71 Hz, 1 H) 3.35 (s, 3 H) 3.69 (m, 1 H) 3.93 (d, J=10.17 Hz, 1 H) 4.03 (dd, J10.50,4.50 Hz, 1 H) 5.17 (dd, J=4.92, 2.88 Hz, 1 H) 5.28 (m, 1 H) 5.35 (d, J=5.00 Hz, 1 H); MS: (M+H)$^+$=487.

Example 184

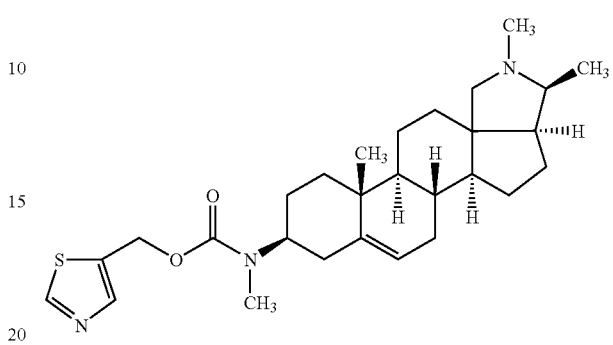

Methyl-(2,3,11a-trimethyl-2,3,3a,4,5,5a,5b,6,8,9,10,
11,11a,11b,12,13-hexadecahydro-1H-2-aza-pentaleno[1,6a-a]phenanthren-9-yl)-carbamic acid thiazol-5-ylmethyl ester The title compound was prepared according to procedures described in Example 182, except substituting carbonic acid 4-nitro-phenyl ester thiazol-5-ylmethyl ester for carbonic acid furan-3-ylmethyl ester 4-nitro-phenyl ester. $^1$H NMR (CDCl$_3$): δ 0.94 (s, 3 H) 1.05-2.11 (m, 23 H) 2.22 (s, 3 H) 2.40 (m, 2 H) 2.82 (d, 3 H) 2.99 (m, 1 H) 3.38 (m, 1 H) 5.33 (s, 2 H) 5.35 (m, 1 H) 7.87 (s, 1 H) 8.80 (s, 1 H); MS: (M+H)$^+$=484.

Example 185

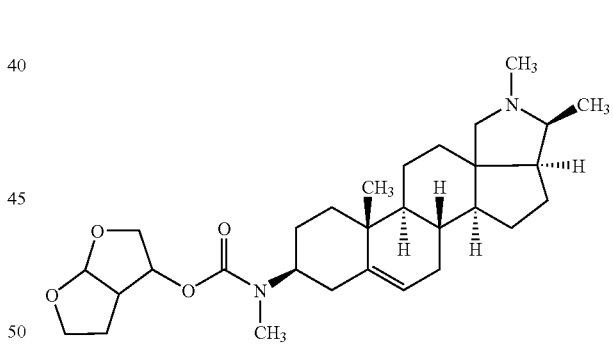

Methyl-(2,3,11a-trimethyl-2,3,3a,4,5,5a,5b,6,8,9,10,
11,11a,11b,12,13-hexadecahydro-1H-2-aza-pentaleno[1,6a-a]phenanthren-9-yl)-carbamic acid hexahydro-furo[2,3-b]furan-3-yl ester The title compound was prepared according to procedures described in Example 182, except substituting carbonic acid hexahydro-furo[2,3-b]furan-3-yl ester 4-nitro-phenyl ester for carbonic acid furan-3-ylmethyl ester 4-nitro-phenyl ester. $^1$H NMR (CDCl$_3$): δ 0.95 (s, 3 H) 0.99-2.04 (m, 25 H) 2.21 (s, 3 H) 2.43 (m, 2 H) 2.83 (d, 3H) 2.99 (d, J=9.83 Hz, 1 H) 3.05 (m, 1 H) 3.73 (m, 1 H) 3.81 (dd, J=9.49, 6.44 Hz, 1 H) 3.90 (m, 1 H) 3.98 (m, 1 H) 4.08 (m, 1 H) 5.19 (d, J=7.80 Hz, 1 H) 5.37 (d,J=4.75 Hz, 1 H) 5.73 (d, J=5.43 Hz, 1 H); MS: (M+H)$^+$=499.

Example 186

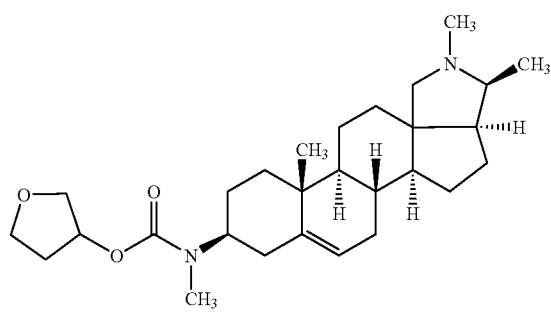

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid tetrahydro-furan-3-yl ester The title compound was prepared according to procedures described in Example 182, except substituting carbonic acid 4-nitro-phenyl ester tetrahydro-furan-3-yl ester for carbonic acid furan-3-ylmethyl ester 4-nitro-phenyl ester. $^1$H NMR (CDCl$_3$): δ 0.96 (m, 3 H) 1.01-2.22 (m, 28 H) 2.41 (m, 2 H) 2.80 (s, 3 H) 2.99 (m, 1 H) 3.70 (m, 1 H) 3.87 (m, 4 H) 5.27 (m, 1 H) 5.36 (d, J=4.75 Hz, 1 H); MS: (M+H)$^+$=457.

Example 187

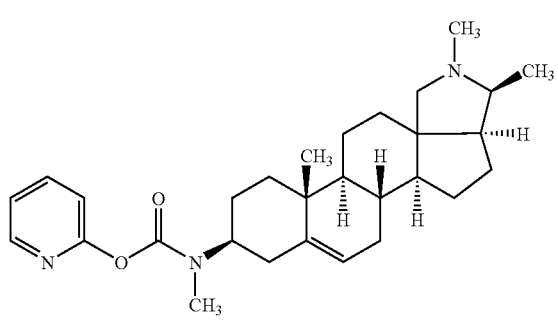

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid pyridin-2-yl ester The title compound was prepared according to procedures described in Example 182, except substituting carbonic acid dipyridin-2-yl ester for carbonic acid furan-3-ylmethyl ester 4-nitro-phenyl ester. $^1$H NMR (CDCl$_3$): δ 0.97 (s, 3 H) 1.02-2.34 (m, 26 H) 2.53 (m, 2 H) 2.95 (s, 3 H) 3.03 (m, 1 H) 4.02 (m, 1 H) 5.39 (s, 1 H) 7.11 (m, 1) 7.17 (dd, J=7.12, 5.42 Hz, 1 H) 7.75 (m, 1 H) 8.38 (dd, J=5.09, 1.70 Hz, 1 H); MS: (M+H)$^+$=464.

Example 188

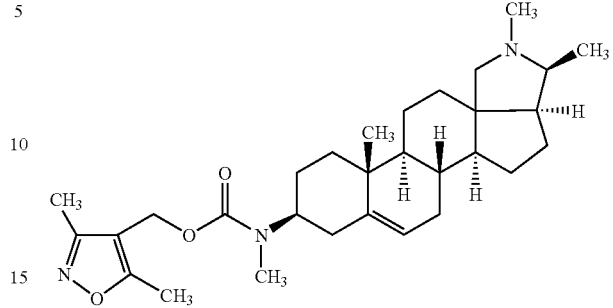

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 3,5-dimethyisoxazol-4-ylmethyl ester The title compound was prepared according to procedures described in Example 182, except substituting carbonic acid 3,5-dimethyl-isoxazol-4-ylmethyl ester 4-nitro-phenyl ester for carbonic acid furan-3-ylmethyl ester 4-nitro-phenyl ester. $^1$H NMR (CDCl$_3$): δ 0.93 (s, 3 H) 1.00-2.13 (m, 23 H) 2.21 (s, 3H) 2.28 (s, 3 H) 2.37 (s, 3 H) 2.77 (s, 3 H) 2.99 (m, 1 H) 3.81 (m, 1 H) 4.89 (s, 2 H) 5.35 (m, 1 H); MS: (M+H)$^+$=496.

Example 189

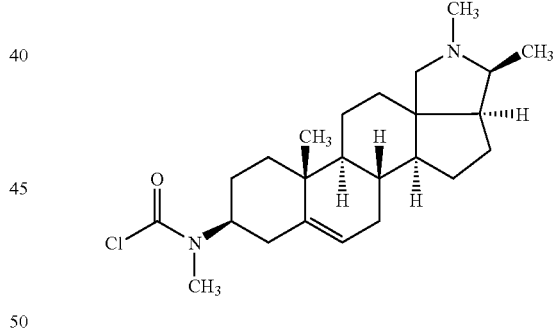

189A. Methyl-(2,3,11a-trimethyl-2,3,3a,4,5,5a,5b,6,8,9,10,11,11a,11b,12,13-hexadecahydro-1H-2-azapentaleno[1,6a-a]phenanthren-9-yl)-carbamic acid chloride Compound 7B (125 mg, 0.36 mmol) was dissolved in dichloromethane (5 mL) and cooled to 0° C. Triethylamine (150 µL, 1.1 mmol) and phosgene (20% in toluene, 0.23 mL, 0.44 mmol) were added to it. The mixture was stirred at 0° C. for 3 hours. The reaction mixture was quenched with water, extracted with dichloromethane. The combined extracts were dried over Na$_2$SO$_4$, filtered and concentrated to give crude desired product (144.6 mg, 97.8%), which was used in next step without further purification.

MS: (M+H)$^+$=477.

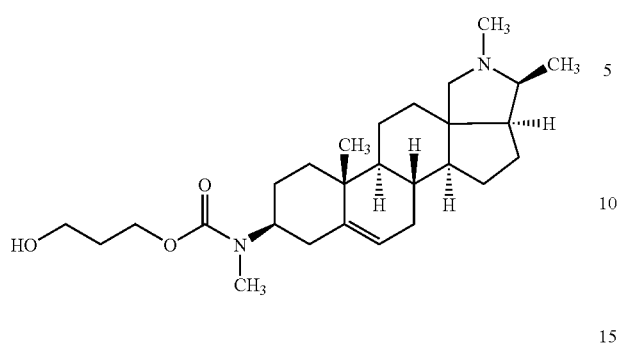

189B. Methyl-(2,3,11a-trimethyl-2,3,3a,4,5,5a,5b,6,8,9,10,11,11a,11b,12,13-hexadecahydro-1H-2-azapentaleno[1,6a-a]phenanthren-9-yl)-carbamic acid 3-hydroxy-propyl ester Compound 189A (30 mg, 0.074 mmol) and 1,3-propanediol (54μL, 0.061 mmol), were dissolved in pyridine (1 mL). The mixture was stirred at room temperature for 5 days. Stripped of pyridine, the crude reaction mixture was purified on silica gel column using 0.5% ammonium hydroxide and 5% methanol in dichloromethane to give the desired product (7.3 mg, 22.8% yield).

$^1$H NMR (CDCl$_3$): δ 0.96 (m, 3 H) 1.04-2.11 (m, 25 H) 2.22 (s, 3 H) 2.42 (m, 2 H) 2.56 (br s, 1 H) 2.81 (m, 3 H) 3.00 (m, 1 H) 3.65 (m, 2 H) 3.87 (m, 1 H) 4.28 (t, J=5.76 Hz, 2 H) 5.36 (m, 1 H); MS: (M+H)$^+$=445.

Example 190

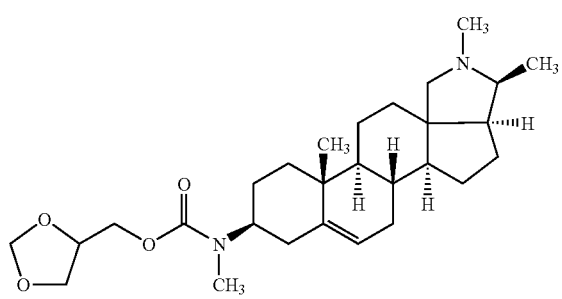

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid [1,3]dioxolan-4-ylmethyl ester The title compound was prepared according to procedures described in Example 189B, except substituting glycerol formal for 1,3-propanediol. MS: (M+H)$^+$=473.

Example 191

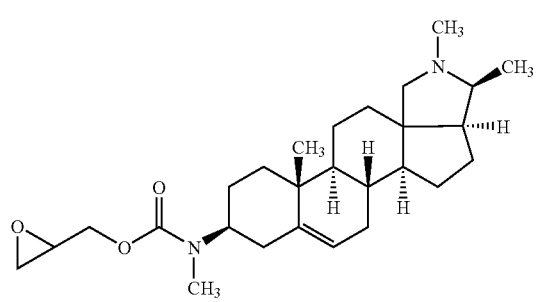

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid oxiranylmethyl ester The title compound was prepared according to procedures described in Example 189B, except substituting glycidol for 1,3propanediol. $^1$H NMR (CDCl$_3$): δ 0.95 (m, 3 H) 1.13-2.25 (m, 26 H) 2.43 (m, 2 H) 2.64 (dd,J=4.92, 2.54 Hz, 1 H) 2.84 (m, 3 H) 3.03 (m, 1 H) 3.24 (m, 1 H) 3.68 (m, 1 H) 3.90 (m, 2 H) 4.45 (d,J=9.0 Hz, 1 H) 5.36 (d, J=5.09 Hz, 1 H); MS: (M+H)$^+$=443.

Example 192

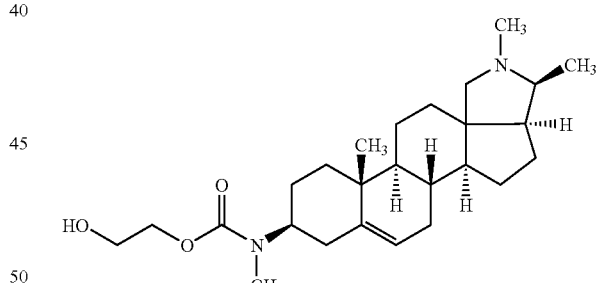

Methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 2-hydroxy-ethyl ester The title compound was prepared according to procedures described in Example 189B, except substituting ethlene glycol for 1,3-propanediol. $^1$H NMR (CDCl$_3$): δ 0.95 (s, 3 H) 1.03-2.12 (m, 23 H) 2.21 (s, 3 H) 2.41 (m, 2 H) 2.73 (br s, 1 H) 2.84 (s, 3 H) 2.97 (m, 1 H) 3.83 (d, J=4.75 Hz, 2 H) 3.94 (m, 1 H) 4.26 (m, 2 H) 5.36 (d, J=6.00 Hz, 1 H); MS: (M+H)$^+$=431.

Example 193

Determination of Biological Activity

To determine the effectiveness of representative compounds of this invention as histamine-3 receptor ligands ($H_3$ receptor ligands), the following tests were conducted according to methods previously described (European Journal of Pharmacology, 188:219-227 (1990); Journal of Pharmacology and Experimental Therapeutics, 275:598-604 (1995); Journal of Pharmacology and Experimental Therapeutics, 276:1009-1015 (1996); and Biochemical Pharmacology, 22:3099-3108 (1973)).

Briefly, male Sprague-Dawley rat brain cortices were homogenized (1 g tissue/10 mL buffer) in 50 mM Tris-HCl/5 mM EDTA containing protease inhibitor cocktail (Calbiochem) using a polytron set at 20,500 rpm. Homogenates were centrifuged for 20 minutes at 40,000×g. The supernatant was decanted, and pellets were weighed. The pellet was resuspended by polytron homogenization in 40 mL 50 mM TrisHCl/5 mM EDTA with protease inhibitors and centrifuged for 20 minutes at 40,000×g. The membrane pellet was resuspended in 6.25 volumes (per gram wet weight of pellet) of 50 mM Tris-HCl/5 mM EDTA with protease inhibitors and aliquots flash frozen in liquid $N_2$ and stored at −70° C. until used in assays. Rat cortical membranes (12 mg wet weight/tube) were incubated with ($^3H$)—N-α-methylhistamine (~0.6 nM) with or without $H_3$ receptor antagonists in a total incubation volume of 0.5 mL of 50 mM TrisHCl/5 mM EDTA (pH 7.7). Test compounds were dissolved in DMSO to provide a 20 mM solution, serially diluted and then added to the incubation mixtures prior to initiating the incubation assay by addition of the membranes. Thioperamide (3 µM) was used to determine nonspecific binding. Binding incubations were conducted for 30 minutes at 25° C. and terminated by addition of 2 mL of ice cold 50 mM TrisHCl (pH 7.7) and filtration through 0.3% polyethylenimine-soaked Unifilter plates (Packard). These filters were washed 4 additional times with 2 mL of ice-cold 50 mM Tris-HCl and dried for 1 hour. Radioactivity was determined using liquid scintillation counting techniques. Results were analyzed by Hill transformation and $K_i$ values were determined using the Cheng-Prusoff equation.

Representative compounds of the invention bound to histamine3 receptors with binding affinities from about 810 nM to about 0.12 nM. Preferred compounds of the invention bound to histamine-3 receptors with binding affinities from about 100 nM to about 0.12 nM. More preferred compounds of the invention bound to histamine-3 receptors with binding affinities from about 20 nM to about 0.12 nM.

Compounds of the invention are histamine3 receptor ligands that modulate function of the histamine-3 receptor by altering the activity of the receptor. These compounds may be inverse agonists that inhibit the basal activity of the receptor or they may be antagonists that completely block the action of receptorectivating agonists. These compounds may also be partial agonists that partially block or partially activate the histamine-3 receptor or they may be agonists that activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound of the formula:

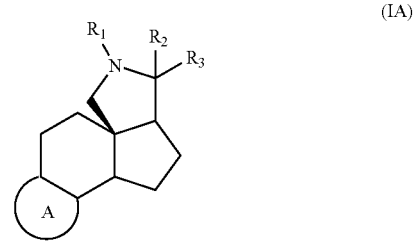

(IA)

or a pharmaceutically acceptable salt thereof, wherein
$R_1$ is selected from the group consisting of hydrogen, acetyl, alkyl, fluoroalkyl, and cycloalkyl;
$R_2$ and $R_3$ are each independently selected from the group consisting of hydrogen and alkyl, or $R_2$ and $R_3$ taken together form a 3- to 6-membered ring;
Ring A of the formula:

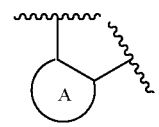

is selected from the following:

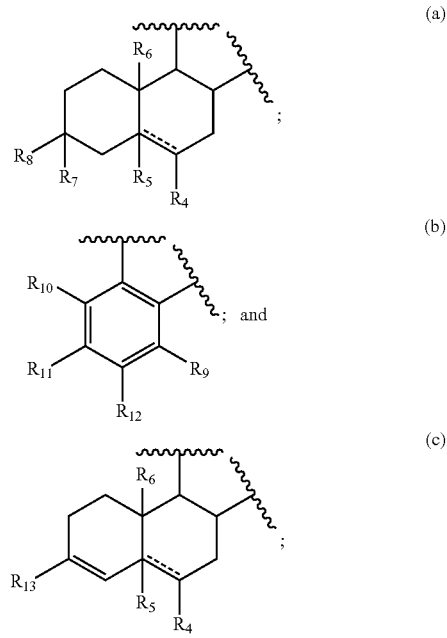

wherein:
the dotted line represents an optional bond;
$R_4$ and $R_5$ are each independently selected from the group consisting of hydrogen and fluorine, provided that $R_5$ is present only when the bond represented by the dotted line is absent;

$R_6$ is selected from the group consisting of hydrogen, alkyl, and fluorine;

one of $R_7$ and $R_8$ is hydrogen; and the other of $R_7$ and $R_8$ is selected from the group consisting of:
a) $NR_{18}R_{19}$;
b) $OR_{20}$, $SR_{20}$, $O(C=O)N(R_{20})(R_{21})$, and
c) $NR_{22}(C=O)R_{25}$, $NR_{22}(C=O)NR_{26}R_{27}$, $NR_{22}(C=O)CH(NR_{28}R_{29})R_{30}$, $N(R_{22})(C=O)OR_{20}$, or $NR_{22}(C=O)C(OR_{23})R_{30}R_{30b}$; and
d) $NR_{22}SO_2R_{31}$ or $NR_{22}SO_2N(R_{22})(R_{23})$;

or $R_7$ and $R_8$ taken together with the carbon atom to which each is attached forms a group of the formula $—C=C(R_a)(R_b)$, wherein $R_a$ and $R_b$ are each independently selected from the group consisting of hydrogen, alkyl, and cycloalkyl;

$R_9$ and $R_{10}$ are each independently selected from the group consisting of hydrogen, halogen, alkyl, and cyano;

$R_{11}$ and $R_{12}$ are each independently selected from the group consisting of hydrogen, heteroaryl, heterocycle, aryl, arylalkyl, aryloxy, arylcarbonyl, arylcarbonyloxy, arylalkoxy, alkylsulfonyl, arylsulfonyl, and trifluoromethylsulfonyl; or one of $R_{10}$ and $R_{11}$ or $R_{11}$ and $R_{12}$ taken together with the atoms to which each is attached form a 5 to 6-membered aromatic or heteroaromatic ring;

$R_{13}$ is selected from the group consisting of alkyl, cycloalkyl, aryl, and heteroaryl;

$R_{18}$ is hydrogen or $C_1$-$C_6$ alkyl and $R_{19}$ is selected from the group consisting of aryl and heteroaryl, or $R_{18}$ and $R_{19}$ at each occurrence is taken together form a 3 to 8-membered heterocycle;

$R_{20}$ and $R_{21}$ at each occurrence are each independently selected from the group consisting of hydrogen, alkyl, cycloalkyl, alkoxyalkyl, cyanoalkyl, hydroxyalkyl, haloalkyl, aryl, aryloxy, arylalkyl, arylsulfonyl, heteroaryl, heteroarylalkyl, heteroarylcarbonyl, heterocycle, and heterocyclealkyl, provided that when $R_7$ or $R_8$ is $OR_{20}$, $R_{20}$ is not hydrogen or methyl;

$R_{22}$ at each occurrence is selected from the group consisting of hydrogen and alkyl;

$R_{23}$ at each occurrence is selected from the group consisting of hydrogen, alkyl, and alkylcarbonyl;

$R_{25}$ at each occurrence is independently selected from the group consisting of $C_2$-$C_6$ alkyl, alkoxyalkyl, hydroxyalkyl, a phenyl ring substituted with 1, 2 or 3 substituents selected from the group consisting of halogen, cyano, alkyl, and alkoxy, naphthyl, arylalkyl, cycloalkyl, cycloalkylalkyl, cyanoalkyl, haloalkyl, heteroaryl, heteroarylalkyl, heteroarylcarbonyl, heterocycle, and heterayclealkyl;

$R_{26}$ and $R_{27}$ are each independently selected from the group consisting of alkyl, cycloalkyl, aryl, heteroaryl, and heterocycle, provided that $R_{26}$ and $R_{27}$ are not both alkyl, or $R_{26}$ and $R_{27}$ taken together with the nitrogen atom to which each is attached forms an aromatic or non-aromatic 5 to 6-membered ring, wherein 0, 1, or 2 carbon atoms in the ring is substituted with a heteroatom selected from O, S, or $NR_{23}$;

$R_{28}$ and $R_{29}$ at each occurrence are each independently selected from the group consisting of hydrogen, alkyl, alkylcarbonyl, alkoxycarbonyl, cycloalkyl, aryl, heteroaryl, and heterocycle, or $R_{28}$ and $R_{29}$ taken together with the nitrogen atom to which each is attached forms an aromatic or non-aromatic 5- to 6-membered ring, wherein 0, 1, or 2 carbon atoms in the ring is substituted with a heteroatom selected from O, S, or $NR_{23}$ $R_{30}$ at each occurrence is independently selected from the group consisting of hydrogen, alkyl, alkoxyalkyl, hydroxyalkyl, aryl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{30b}$ is selected from the group consisting of hydrogen and alkyl, or when $R_{30}$ is alkyl and $R_{30b}$ is alkyl, the alkyl groups can be bonded together to form a $C_3$-$C_4$ cycloalkyl group; and $R_{31}$ is selected from the group consisting of alkyl, cycloalkyl, aryl, heterocycle, and heteroaryl.

2. A compound of the formula:

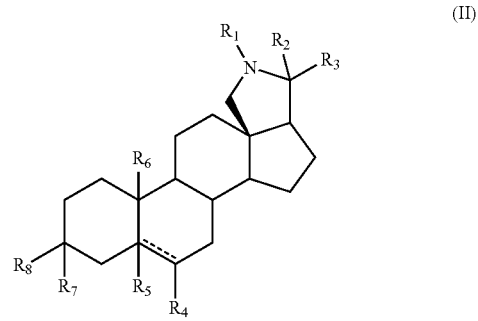

(II)

wherein:
the dotted line represents an optional bond;
$R_1$ is selected from the group consisting of hydrogen, acetyl, alkyl, fluoroalkyl, and cycloalkyl;
$R_2$ and $R_3$ are each independently selected from the group consisting of hydrogen and alkyl, or $R_2$ and $R_3$ taken together form a 3- to 6-membered ring;
$R_4$ and $R_5$ are each independently selected from the group consisting of hydrogen and fluorine, provided that $R_5$ is present only when the bond represented by the dotted line is absent;
$R_6$ is selected from the group consisting of hydrogen, alkyl, and fluorine;
one of $R_7$ and $R_8$ is hydrogen; and the other of $R_7$ and $R_8$ is selected from the group consisting of:
a) $NR_{18}R_{19}$;
b) $OR_{20}$, $SR_{20}$, or $O(C=O)N(R_{20})(R_{21})$, and
c) $NR_{22}(C=O)R_{25}$, $NR_{22}(C=O)NR_{26}R_{27}$, $NR_{22}(C=O)CH(NR_{28}R_{29})R_{30}$, $N(R_{22})(C=O)OR_{20}$, or $NR_{22}(C=O)C(OR_{23})R_{30}R_{30b}$; and
d) $NR_{22}SO_2R_{31}$ or $NR_{22}SO_2N(R_{22})(R_{23})$;

or $R_7$ and $R_8$ taken together with the carbon atom to which each is attached forms a group of the formula $—C=C(R_a)(R_b)$, wherein $R_a$ and $R_b$ are each independently selected from the group consisting of hydrogen, alkyl, and cycloalkyl;

$R_{18}$ is hydrogen or $C_1$-$C_6$ alkyl and $R_{19}$ is selected from the group consisting of aryl and heteroaryl, or $R_{18}$ and $R_{19}$ at each occurrence is taken together form a 3 to 5-membered heterocycle;

$R_{20}$ and $R_{21}$ at each occurrence are each independently selected from the group consisting of hydrogen, alkyl, cycloalkyl, alkoxyalkyl, cyanoalkyl, hydroxyalkyl, haloalkyl, aryl, aryloxy, arylalkyl, arylsulfonyl, heteroaryl, heteroarylalkyl, heteroarylcarbonyl, heterocycle, and heterocyclealkyl, provided that when $R_7$ or $R_8$ is $OR_{20}$, $R_{20}$ is not hydrogen or methyl;

$R_{22}$ at each occurrence is selected from the group consisting of hydrogen and alkyl;

$R_{23}$ at each occurrence is selected from the group consisting of hydrogen, alkyl, and alkylcarbonyl;

$R_{25}$ at each occurrence is independently selected from the group consisting of $C_2$-$C_6$ alkyl, alkoxyalkyl, hydroxyalkyl, a phenyl ring substituted with 1, 2 or 3 substituents selected from the group consisting of halogen, cyano, alkyl, and alkoxy, naphthyl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{26}$ and $R_{27}$ are each independently selected from the group consisting of alkyl, cycloalkyl, aryl, heteroaryl, and heterocycle, provided that $R_{26}$ and $R_{27}$ are not both alkyl, or $R_{26}$ and $R_{27}$ taken together with the nitrogen atom to which each is attached forms an aromatic or non-aromatic 5 to 6-membered ring, wherein 0, 1, or 2 carbon atoms in the ring is substituted with a heteroatom selected from O, S, or $NR_{23}$;

$R_{28}$ and $R_{29}$ at each occurrence are each independently selected from the group consisting of hydrogen, alkyl, alkylcarbonyl, alkoxycarbonyl, cycloalkyl, aryl, heteroaryl, and heterocycle, or $R_{28}$ and $R_{29}$ taken together with the nitrogen atom to which each is attached forms an aromatic or nonaromatic 5- to 6-membered ring, wherein 0, 1, or 2 carbon atoms in the ring is substituted with a heteroatom selected from O, S, or $NR_{23}$ $R_{30}$ at each occurrence is independently selected from the group consisting of hydrogen, alkyl, alkoxyalkyl, hydroxyalkyl, aryl, arylalkyl, cycloalkyl, cycloalkylalkyl, cyanoalkyl, haloalkyl, heteroaryl, heteroarylalkyl, heteroarylcarbonyl, heterocycle, and heterocyclealkyl;

$R_{30b}$ is selected from the group consisting of hydrogen and alkyl, or when $R_{30}$ is alkyl and $R_{30b}$ is alkyl, the alkyl groups can be bonded together to form a $C_3$-$C_4$ cycloalkyl group; and $R_{31}$ is selected from the group consisting of alkyl, cycloalkyl, aryl, heterocycle, and heteroaryl.

3. The compound of claim 2, wherein one of $R_7$ and $R_8$ is hydrogen; and the other of $R_7$ and $R_8$ is selected from the group consisting of $NR_{22}$(C=O)$R_{25}$, $NR_{22}$(C=O)CH($NR_{28}R_{29}$)$R_{30}$, and $NR_{22}$(C=O)C(O$R_{23}$)$R_{30}R_{30b}$.

4. The compound of claim 3, wherein $R_7$ or $R_8$ is $NR_{22}$(C=O)CH($NR_{28}R_{29}$)$R_{30}$, wherein $R_{22}$ is alkyl, $R_{28}$ and $R_{29}$ are each hydrogen, and $R_{30}$ is selected from the group consisting of alkyl and aryl.

5. The compound of claim 4, wherein $R_{22}$ is methyl.

6. The compound of claim 1, selected from the group consisting of: trifluoro-methanesulfonic acid 8-methyl-5,6,6a,7,8,9,10,11-octahydro-4bH-benzo[4,5]indeno[1,7a-c]pyrrol-2-yl ester;
1-[3-(8-methyl-5,6,6a,7,8,9,10,11-octahydro-4bH-benzo[4,5]indeno[1,7a-c]pyrrol-2-yl)-phenyl]-ethanone;
1-[3-(8-methyl-5,6,6a,7,8,9,10,11-octahydro-4bH-benzo[4,5]indeno[1,7a-c]pyrrol-2-yl)-phenyl]-ethanone oxime;
1-[3-(8-methyl-5,6,6a,7,8,9,10,11-octahydro-4bH-benzo[4,5]indeno[1,7a-c]pyrrol-2-yl)-phenyl]-ethanone;
benzoic acid 8-acetyl-5,6,6a,7,8,9,10,11-octahydro-4bH-benzo[4,5]indeno[1,7a-c]pyrrol-2-yl ester;
1-(2-benzyloxy-5,6,6a ,7,10,11-hexahydro-4bH-benzo[4,5]indeno[1,7a-c]pyrrol-8-yl)-ethanone;
2,2,N-trimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;
furan-2-carboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;
4-fluoro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
thiophene-2-carboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;
isoxazole-5-carboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;
N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-isonicotinamide;
3-chloro-4-fluoro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
2-(4-methoxy-phenyl)-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;
2,3,4-trifluoro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
4-cyano-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
N-methyl-2-thiophen-2-yl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;
3-chloro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
3-methoxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
4-methoxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
4,N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
4-chloro-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
3-cyano-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
4-bromo-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-benzamide;
3,N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide;
cyclopropanecarboxylic acid methyl-(2,3,11a-trimethyl-2,3,3a,4,5,5a,5b,6,8,9,10,1,11a,11b,12,13-hexadecahydro-1H-2-aza-pentaleno[1,6a-a]phenanthren-9-yl)-amide;
2-methoxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;
N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

2-isopropyl-4-methyl-thiazole-5-carboxylic acid methyl-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-amide;

2-sec-butyl-4-methyl-thiazole-5-carboxylic acid methyl-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-amide;

2-methyl-5-phenyl-furan-3-carboxylic acid methyl-(2,3,11a-trimethyl-2,3,3a,4,5,5a,5b,6,8,9,10,11,11a,11b,12,13-hexadecahydro-1H-2-aza-pentaleno[1,6-a-a]phenanthren-9-yl)-amide;

N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

N-methyl-2-thiophen-3-yl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

N-methyl4-thiophen-2-yl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-butyramide;

2-(3-fluoro-phenyl)N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

N-methyl-2-oxo-2-thiophen-2-yl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

2-indol-1-yl-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

2-benzo[b]thiophen-3-yl-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

N-methyl-2-(3-methyl-benzo[b]thiophen-2-yl)-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

2-furan-2-yl-N-methyl-2-oxo-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

N-methyl-3-thiophen-2-yl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-propionamide;

3-furan-2-yl-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-propionamide;

2-(3-chloro-phenyl)-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

2-(4-chloro-phenyl)-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

2-(2-fluoro-phenyl)-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

2-(4-fluoro-phenyl)-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

N-methyl-2-o-tolyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-acetamide;

ethanesulfonic acid methyl-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-amide;

N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-benzenesulfonamide;

4-cyano-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-benzenesulfonamide;

thiophene-2-sulfonic acid methyl-(2,3,11a-trimethyl-2,3,3a,4,5,5a,5b,6,8,9,10,11,11a,11b,12,13-hexadecahydro-1H-2-aza-pentaleno[1,6-a]phenanthren-9yl)-amide;

4-fluoro-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-benzenesulfonamide;

1,1-dimethyl-3-methyl-3-(2,3,11a-trimethyl-2,3,3a,4,5,5a,5b,6,8,9,10,11,11a,11b,12,13-hexadecahydro-1H-2-aza-pentaleno[1,6-a][phenanthren-9-yl)-sulfamide;

pyrrolidine-1-carboxylic acid methyl)-2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-amide;

1,1-diisopropyl-3-methyl-3-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-urea;

morpholine-4-carboxylic acid methyl-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-amide;

1,1,3-trimethyl-3-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-urea;

methyl{2-methyl-1-[methyl-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-carbamoyl]-propyl}-carbamic acid tert-butyl ester;

3,N-dimethyl-2-methylamino-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-butyramide;

2-(acetyl-methyl-amino)-3, N-dimethyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-butyramide;

2-amino-N-methyl-3-phenyl-N-(2,3,3a,11a-tetramethyl-2,3,3a,4,5,5a,5b,6,8,9,10,11,11a,11b,12,13-hexadecahydro-1H-2-aza-pentaleno[1,6-a]phenanthren-9-yl)-propionamide;

2-amino-N-methyl-3-thiazol-4-yl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-propionamide;

2-amino-N-methyl-N-(2,3,11a-trimethyl-2,3,3a,4,5,5a,5b,6,8,9,10,11,11a,11b,12,13-hexadecahydro-1H-2-aza-pentaleno[1,6-a]phenanthren-9-yl)-propionamide;

2-amino-N-methyl-N-(2,3,11a-trimethyl-2,3,3a,4,5,5a, 5b,6,8,9,10,11,11a,11b,12,13-hexadecahydro-1H-2-aza-pentaleno[1,6a-a]phenanthren-9-yl)-butyramide;

2-amino-3-cyano-N-methyl-N-(2,3,11a-trimethyl-2,3,3a, 4,5,5a,5b,6,8,9,10,11,11a,11b,12,13-hexadecahydro-1H-2-aza-pentaleno[1,6a-a]phenanthren-9-yl)-propionamide;

2-amino-N-methyl-3-thiophen-2-yl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

4-methyl-2-methylamino-pentanoic acid methyl-(2,3, 11a-trimethyl-2,3,3a,4,5,5a,5b,6,8,9,10,11,11a,11b,12, 13-hexadecahydro-1H-2-aza-pentaleno[1,6a-a] phenanthren-9yl)-amide;

2-amino-3-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9yl)-amide;

2-amino-3, N-dimethyl-N-(2,3,11a-trimethyl-2,3,3a,4,5, 5a,5b,6,8,9,10,11,11a,11b,12,13-hexadecahydro-1H-2-aza-pentaleno[1,6a-a]phenanthren-9yl)-butyramide;

2-amino-3-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-amino-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-acetylamino-N-methyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-butyramide;

2-acetylamino-3-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-acetylamino-N-methyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-propionamide;

2-acetylamino-N-methyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-propionamide;

2-acetylamino-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

2-acetylamino-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-acetylamino-3, N-dimethyl-N-(2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl)-butyramide;

2-acetylamino-3, N-dimethyl-N-(2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl)-butyramide;

2-acetylamino-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

2-acetylamino-N-methyl-3-thiophen-2-yl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

2-acetylamino-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

4-[methyl-(2,3,11a-trimethyl-2,3,3a,4,5,5a,5b,6,8,9,10, 11,11a,11b, 12,13-hexadecahydro-1H-2-aza-pentaleno[1,6a-a]phenanthren-9-yl)-amino]-benzonitrile;

3-[methyl-(2,3,11a-trimethyl-2,3,3a,4,5,5a,5b,6,8,9,10, 11,11a,11b, 12,13-hexadecahydro-1H-2-aza-pentaleno[1,6a-a]phenanthren-9-yl)-amino]-benzonitrile;

methyl-thiazol-2-yl-(2,3,11a-trimethyl-2,3,3a,4,5,5a,5b, 6,8,9,10,11,11a,11b,12,13-hexadecahydro-1H-2-aza-pentaleno[1,6a-a]phenanthren-9-yl)-amine;

1-{3-[methyl-(2,3,11a-trimethyl-2,3,3a,4,5,5a,5b,6,8,9, 10,11,11a,11b,12,13-hexadecahydro-1H-2-aza-pentaleno[1,6a-a]phenanthren-9-yl)-amino]-phenyl}-ethanone;

1-{4-[methyl-(2,3,11a-trimethyl-2,3,3a,4,5,5a,5b,6,8,9, 10,11,11a,1b,12,13-hexadecahydro-1H-2-aza-pentaleno[1,6a-a]phenanthren-9-yl)-amino]-phenyl}-ethanone;

acetic acid 1-[methyl-(2,3,11a-trimethyl-2,3,3a,4,5,5a,5b, 6,8,9,10,11,11a,11b,12,13-hexadecahydro-1H-2-aza-pentaleno[1,6a-a]phenanthren-9-yl)-carbamoyl]-2-phenyl-ethyl ester;

2-hydroxy-N-methyl-3-phenyl-N-(2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl)-propionamide;

acetic acid 1-[methyl-(2,3,11a-trimethyl-2,3,3a,4,5,5a,5b, 6,8,9,10,11,11a,11b,12,13-hexadecahydro-1H-2-aza-pentaleno[1,6a-a]phenanthren-9yl)-carbamoyl]-2-phenyl-ethyl ester;

2-hydroxy-N-methyl-3-phenyl-N-(2,3,11a-trimethyl-2,3, 3a,4,5,5a,5b,6,8,9,10,11,11a,11b,12,13-hexadecahydro-1H-2-aza-pentaleno[1,6a-a]phenanthren-9-yl)-propionamide;

acetic acid 3-methyl-1-[methyl-(2,3,11a-trimethyl-2,3,3a, 4,5,5a,5b,6,8,9,10,11,11a,11b,12,13-hexadecahydro-1H-2-aza-pentaleno[1,6a-a]phenanthren-9-yl)-carbamoyl]-butyl ester;

2-hydroxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

acetic acid 2-methyl-1-[methyl-(2,3,11a-trimethyl-2,3,3a, 4,5,5a,5b,6,8,9,10,11,11a,11b,12,13-hexadecahydro-1H-2-aza-pentaleno[1,6a-a]phenanthren-9-yl)-carbamoyl]-propyl ester;

2-hydroxy-3, N-dimethyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-butyramide;

acetic acid 1-methyl-1-[methyl-(2,3,11a-trimethyl-2,3,3a, 4,5,5a,5b,6,8,9,10,11,11a,11b,12,13-hexadecahydro-1H-2-aza-pentaleno[1,6a-a]phenanthren-9-yl)-carbamoyl]-propyl ester;

2-hydroxy-2, N-dimethyl-N-(2,3,11a-trimethyl-2,3,3a,4, 5,5a,5b,6,8,9,10,11,11a,11b,12,13-hexadecahydro-1H-2-aza-pentaleno[1,6a-a]phenanthren-9-yl)-butyramide;

acetic acid 1-[methyl-(2,3,11a-trimethyl-2,3,3a,4,5,5a,5b, 6,8,9,10,11,11a,11b,12,13-hexadecahydro-1H-2-aza-pentaleno[1,6a-a]phenanthren-9-yl)-carbamoyl]-cyclopropyl ester;

1-hydroxy-cyclopropanecarboxylic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

acetic acid 1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-pentyl ester;

2-hydroxy-hexanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

acetic acid [methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-phenyl-methyl ester;

2-hydroxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9yl)-acetamide;

acetic acid 2,2,2-trifluoro-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-ethyl ester;

3,3,3-trifluoro-2-hydroxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

acetic acid (4-fluoro-phenyl)-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-methyl ester;

2-(4-fluoro-phenyl)-2-hydroxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

acetic acid (4-methoxy-phenyl)-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-methyl ester;

2-hydroxy-2-(4-methoxy-phenyl)-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

acetic acid (3,4-difluoro-phenyl)-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-methyl ester;

2-(3,4-difluoro-phenyl)-2-hydroxy-N-methyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

acetic acid [methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-phenyl-methyl ester;

2-hydroxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

acetic acid [methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-phenyl-methyl ester;

2-hydroxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

acetic acid 3-methyl-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamoyl]-butyl ester;

2-hydroxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

acetic acid 3-methyl-1-[methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9yl)-carbamoyl]-butyl ester;

2-hydroxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-methoxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

2-methoxy-N-methyl-2-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-acetamide;

2-methoxy-N-methyl-2-phenyl-N-(2,3,11a-trimethyl-2,3,3a,4,5,5a,5b,6,8,9,10, 11,11a,11b,12,13-hexadecahydro-1H-2-aza-pentaleno[1,6a-a]phenanthren-9-yl)-acetamide;

2-methoxy-hexanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-methoxy-4-methyl-pentanoic acid methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-amide;

2-methoxy-N-methyl-3-phenyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-propionamide;

2-methoxy-3, N-dimethyl-N-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-butyramide;

9-ethylidene-2,3,11a-trimethyl-2,3,3a,4,5,5a,5b,6,8,9,10,11,11a,11b, 12,13-hexadecahydro-1H-2-aza-pentaleno[1,6a-a]phenanthrene;

9-isopropylidene-2,3,11a-trimethyl-2,3,3a,4,5,5a,5b,6,8,9,10,11,11a 11b,12,13-hexadecahydro-1H-2-aza-pentaleno[1,6a-a]phenanthrene;

9-benzyloxy-2,3,11a-trimethyl-2,3,3a,4,5,5a,5b,6,8,9,10,11,11a,11b, 12,13-hexadecahydro-1H-2-aza-pentaleno[1,6a-a]phenanthrene;

benzenesulfonic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;

4-cyano-benzenesulfonic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;

furan-2-ylmethyl-methyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;

methyl-propyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
benzyl-methyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
methyl-(6-methyl-pyridin-2-ylmethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
methyl-(tetrahydro-furan-2-ylmethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
(2-fluoro-ethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
furan-2-ylmethyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
(2-cyano-ethyl)-(tetrahydro-furan-2-ylmethyl)-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
benzyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
propyl-carbamic acid 2,3,11a-trimethyl-2,3,3a,4,5,5a,5b,6,8,9,10,11,11a,11b,12,13-hexadecahydro-1H-2-aza-pentaleno[1,6a-a]phenanthren-9-yl ester;
N-methyl-2-thiophen-2-yl-N-(2,3,11a-trimethyl-octadecahydro-2-aza-pentaleno[1,6a-a]phenanthren-9-yl)-acetamide;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid benzyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid methyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 2,2-dimethyl-propyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid isobutyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid ethyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid tert-butyl ester;
methyl-(2,3,11a-trimethyl-2,3,3a,4,5,5a,5b,6,8,9,10,11,11a,1b,12,13-hexadecahydro-1H-2-aza-pentaleno[1,6a-a]phenanthren-9-yl)-carbamic acid isopropyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid cyclopentyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid furan-3-ylmethyl ester
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 5-methoxy-tetrahydro-furan-3-yl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid thiazol-5-ylmethyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid hexahydro-furo[2,3-b]furan-3-yl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid tetrahydro-furan-3-yl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid pyridin-2-yl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 3,5-dimethyl-isoxazol-4-ylmethyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 3-hydroxy-propyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid[1,3]dioxolan-4-ylmethyl ester;
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid oxiranylmethyl ester; and
methyl-(2,3,11a-trimethyl-2,3,3a,4,5,5a,5b,6,8,9,10,11,11a,11b,12,13-hexadecahydro-1H-2-aza-pentaleno[1,6a-a]phenanthren-9-yl)-carbamic acid 2-hydroxy-ethyl ester.

* * * * *

UNITED STATES PATENT AND TRADEMARK OFFICE
CERTIFICATE OF CORRECTION

PATENT NO. : 7,345,034 B2
APPLICATION NO. : 11/096382
DATED : March 18, 2008
INVENTOR(S) : Zhao et al.

Page 1 of 4

It is certified that error appears in the above-identified patent and that said Letters Patent is hereby corrected as shown below:

Specification:

Column 13-14 (Scheme 1) Line No. 1 – Below " 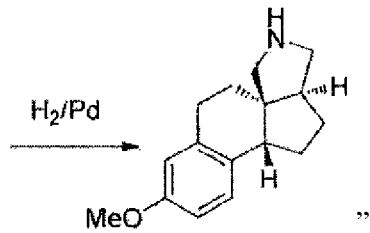 "

Delete "1A-b" and insert -- 1A-a --

Column 94 Line No. 45-67 – Delete " 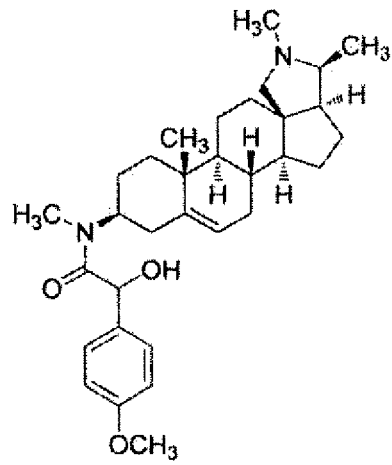 "

Signed and Sealed this
Eleventh Day of September, 2012

David J. Kappos
*Director of the United States Patent and Trademark Office*

Specification:
Insert -- 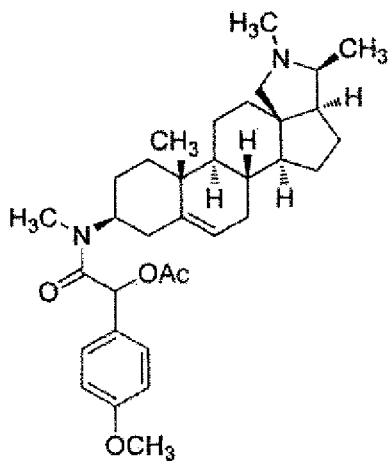 --
Column 114 Line No. 50-65 – Delete " 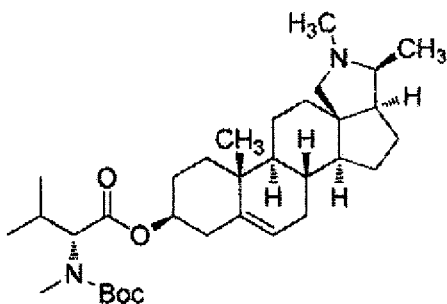 "
Insert -- 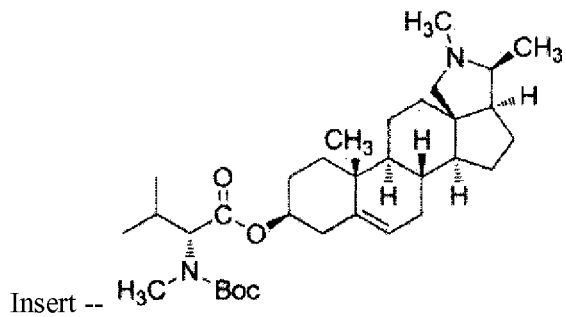 --
Column 124 Line No. 15-30 – Delete " 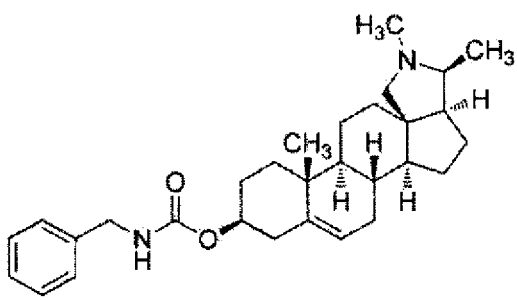 "

CERTIFICATE OF CORRECTION (continued)
U.S. Pat. No. 7,345,034 B2

Specification:

Insert -- 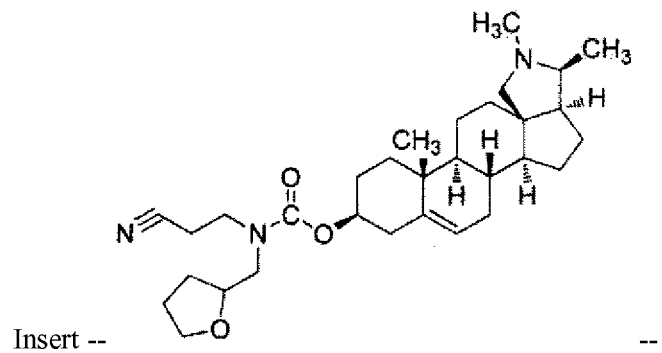 --

Column 126 Line No. 10-25 – Delete " 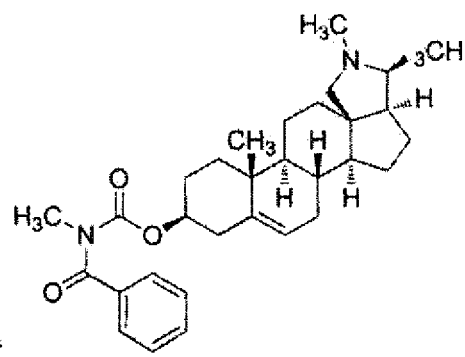 "

Insert -- 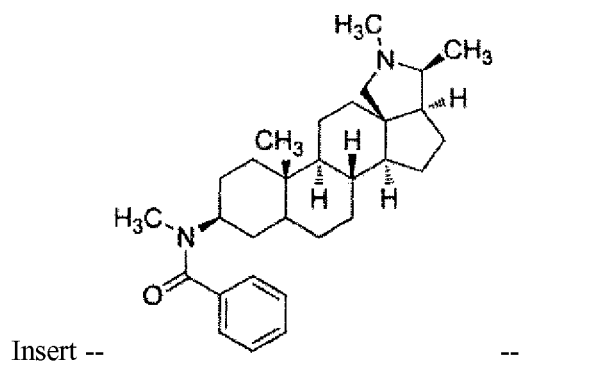 --

Column 128 Line No. 5-20 – Delete " 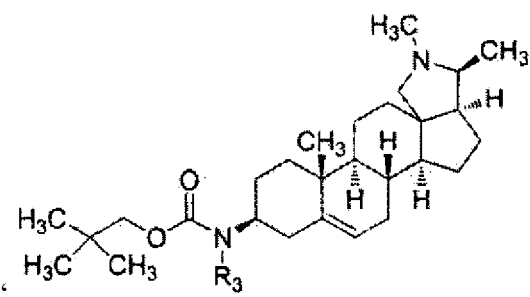 "

CERTIFICATE OF CORRECTION (continued)
U.S. Pat. No. 7,345,034 B2

Specification:

Insert -- 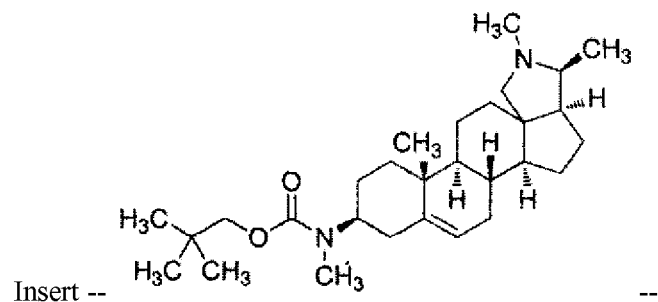 --